(12) United States Patent
Ustav

(10) Patent No.: US 6,479,279 B2
(45) Date of Patent: *Nov. 12, 2002

(54) EPISOMAL VECTORS AND USES THEREOF

(75) Inventor: Mart Ustav, Tartu (EE)

(73) Assignee: Estonian Biocentre, Tartu (EE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,068

(22) PCT Filed: Dec. 27, 1996

(86) PCT No.: PCT/EE96/00004
§ 371 (c)(1),
(2), (4) Date: Sep. 28, 1998

(87) PCT Pub. No.: WO97/24451
PCT Pub. Date: Jul. 10, 1997

(65) Prior Publication Data
US 2002/0086419 A1 Jul. 4, 2002

Related U.S. Application Data

(63) Continuation-in-part of application No. 08/581,269, filed on Dec. 29, 1995, now abandoned.

(51) Int. Cl.[7] .......................... C12N 15/86; C12N 15/63
(52) U.S. Cl. ................... 435/320.1; 435/455; 435/456; 435/457; 536/23.1; 536/23.72; 536/24.1
(58) Field of Search ................................ 435/325, 366, 435/320.1, 455, 456, 457; 536/23.1, 23.72, 24.1

(56) References Cited

FOREIGN PATENT DOCUMENTS

WO   WO 94/12629   9/1994

OTHER PUBLICATIONS

Rodriguez et al. Vectors: A Survey of Molecular Cloning Vectors and Their Uses. Boston: Butterworths, p. 477–478, 1988.*
Bonne–Andrea, C. et al., *J. Virol.*, 69: 3201–3205 (1995).
Chiang, C. M. et al., *Proc. Natl. Acad. Sci. USA*, 89: 5799–5803 (1992).
DePamphilis, M. D., *Annu. Rev. Biochem.*, 62: 29–63 (1993).
Dowhanick et al., *J. Virol.*, 69 (12):7791–7799(1995).
Dvoretzky, I. et al., *Virology*, 103: 369–375 (1980).
Giri and Yaniv, *EMBO*, 70(9):2823–2829 (1988).
Joh et al., *Gene* 161:227–230 (1995).
Krysan, P. J. et al., *Mol. Cell. Biol.*, 9: 1026–1033 (1989).
Kuo, S. R. et al., *J. Biol. Chem.*, 269: 24058–24065 (1994).
Law, M. F. et al., *Proc. Natl. Acad. Sci. USA*, 78:2727–2731 (1981).
Müller, F. et al., *J. Biol. Chem.*, 269: 17086–17094 (1994).
Nallaseth, F.S. and M. DePamphilis, *J. Virol.*, 68: 3051–3064 (1994).
Nordström, K., *Cell*, 63: 1121–1124 (1990).
Ohe, et al, *Gene*, 6:325–333 (1995).
Stillman, B., *J. Biol. Chem.*, 269: 7047–7050 (1994).
Tsurimoto, T. et al., *Nature*, 346: 534–539 (1990).
Ustav, M. and M. Stenlund, *EMBO J.*,10: 449–457 (1991).
Ustav, M. et al., *EMBO J.*, 10: 4321–4329 (1991).
Ustav, M et al., *Proc. Natl. Acad. Sci. USA*, 90: 898–902 (1993).
Weinberg, David H. et al., *Proc. Natl. Acad. Sci. USA*, 87:8692–8696 (1990).
Yang, L. et al., *Nature*, 353:628–632 (1991).

* cited by examiner

*Primary Examiner*—David Guzo
(74) *Attorney, Agent, or Firm*—Kathleen Madden Williams (Palmer & Dodge, LLP)

(57) ABSTRACT

The invention relates to a recombinant vector for stable persistence of exogenous DNA in a eukaryotic cell, and the uses of the recombinant vector for long-term stable production of gene product in the host cell, the vector including the minichromosomal maintenance element of papillomavirus.

26 Claims, 37 Drawing Sheets

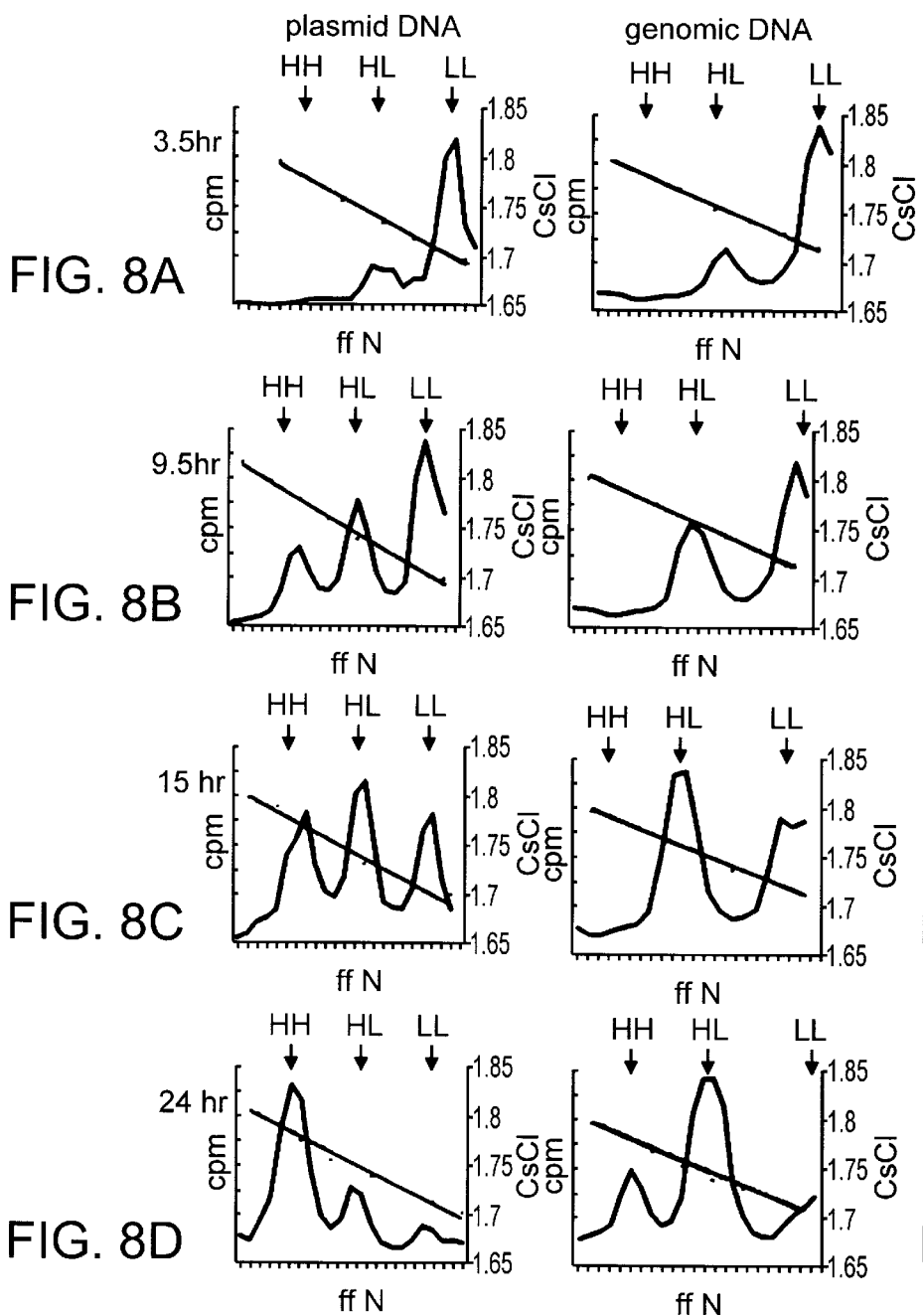

| FIG. 20A | FIG. 20B | FIG. 20C | FIG. 20D | FIG. 20E | FIG. 20F |

FIG. 20

```
      2600           2610           2620           2630           2640
        |              |              |              |              |
GTG AAG AGG ATG GAG ACA GCA TGC GAA CGT TTA CAT GTA GCG CAA
Val Lys Arg MET Glu Thr Ala Cys Glu Arg Leu His Val Ala Gln 2650           2660           2670           2680
        |              |              |              |
GAA ACA CAA ATG CAG TTG ATT GAG AAA AGT AGT GAT AAG TTG CAA
Glu Thr Gln MET Gln Leu Ile Glu Lys Ser Ser Asp Lys Leu Gln
 13

2690           2700           2710   2720           2730
        |              |              |     **             |
GAT CAT ATA CTG TAC TGG ACT GCT GTT AGA ACT GAG AAC ACA CTG
Asp His Ile Leu Tyr Trp Thr Ala Val Arg Thr Glu Asn Thr Leu
 28
```

FIG. 20A

```
        2740                2750                2760                2770
         |                   |                   |                   |
CTT TAT GCT GCA AGG AAA AAA GGG GTG ACT GTC CTA GGA CAC TGC
Leu Tyr Ala Ala Arg Lys Lys Gly Val Thr Val Leu Gly His Cys
 43

2780                2790                2800                2810                2820
         |                   |                   |                   |                   |
AGA GTA CCA CAC TCT GTA GTT TGT CAA GAG AGA GCC AAG CAG GCC
Arg Val Pro His Ser Val Val Cys Gln Glu Arg Ala Lys Gln Ala
 58

2830                2840                2850                2860
         *                   |                   |                   |
ATT GAA ATG CAG TTG TCT TTG CAG GAG TTA AGC AAA ACT GAG TTT
Ile Glu MET Gln Leu Ser Leu Gln Glu Leu Ser Lys Thr Glu Phe
 73

2870                2880                2890                2900                2910
         |                   |                   |                   |                   |
GGG GAT GAA CCA TGG TCT TTG GAC ACA AGC TGG GAC CGA TAT
Gly Asp Glu Pro Trp Ser Leu Asp Thr Ser Trp Asp Arg Tyr
 88

2920                2930                2940                2950
         |                   |                   |                   |
ATG TCA GAA CCT AAA CGG TGC TTT AAG AAA GGC GCC AGG GTG GTA
MET Ser Glu Pro Lys Arg Cys Phe Lys Lys Gly Ala Arg Val Val
103
```

FIG. 20B

```
       2960         2970         2980         2990         3000
        |            |            |            |            |
       GAG GTG GAG TTT GAT GGA AAT GCA AGC AAT ACA AAC TGG TAC ACT
       Glu Val Glu Phe Asp Gly Asn Ala Ser Asn Thr Asn Trp Tyr Thr
       118

3010         3020         3030         3040
        |            |            |            |
       GTC TAC AGC AAT TTG TAC ATG CGC ACA GAG GAC GGC TGG CAG CTT
       Val Tyr Ser Asn Leu Tyr MET Arg Thr Glu Asp Gly Trp Gln Leu
       133

3050         3060         3070         3080         3090
        |            |            |            |            |
       GCG AAG GCT GGG GCT GAC GGA ACT GGG CTC TAC TGC ACC ATG
       Ala Lys Ala Gly Ala Asp Gly Thr Gly Leu Tyr Tyr Cys Thr MET
       148

3100         3110         3120         3130
        |            |            |     *      |
       GCC GGT GCT GGA CGC ATT TAC TAT TCT CGC TTT GGT GAC GAG GCA
       Ala Gly Ala Gly Arg Ile Tyr Tyr Ser Arg Phe Gly Asp Glu Ala
       163

3140         3150         3160         3170         3180
        |            |            |            |            |
       GCC AGA TTT AGT ACA ACA GGG CAT TAC TCT GTA AGA GAT CAG GAC
       Ala Arg Phe Ser Thr Thr Gly His Tyr Ser Val Arg Asp Gln Asp
       178
```

FIG. 20C

```
      3190              3200              3210              3220
       |                 |                 |                 |
AGA   GTG  TAT  GCT  GGT  GTC  TCA  TCC  ACC  TCT  TCT  GAT  TTT  AGA  GAT
Arg   Val  Tyr  Ala  Gly  Val  Ser  Ser  Thr  Ser  Ser  Asp  Phe  Arg  Asp
193

3230              3240              3250              3260              3270
       |                 |                 |                 |                 |
CGC   CCA  GAC  GGA  GTC  TGG  GTC  GCA  TCC  GAA  GGA  CCT  GAA  GGA  GAC
Arg   Pro  Asp  Gly  Val  Trp  Val  Ala  Ser  Glu  Gly  Pro  Glu  Gly  Asp
208

3280              3290              3300              3310
       |                 |                 |                 |
CCT   GCA  GGA  AAA  GAA  GCC  GAG  CCA  GCC  CAG  CCT  GTC  TCT  TCT  TTG
Pro   Ala  Gly  Lys  Glu  Ala  Glu  Pro  Ala  Gln  Pro  Val  Ser  Ser  Leu
223

3320              3330              3340              3350              3360
       |                 |                 |                 |                 |
CTC   GGC  TCC  CCC  GCC  TGC  GGT  CCC  ATC  AGA  GCA  GGC  CTC  GGT  TGG
Leu   Gly  Ser  Pro  Ala  Cys  Gly  Pro  Ile  Arg  Ala  Gly  Leu  Gly  Trp
238

3370              3380              3390              3400
       |                 |                 |                 |
GTA   CGG  GAC  GGT  CCT  CGC  TCG  CAC  CCC  TAC  AAT  TTT  CCT  GCA  GGC
Val   Arg  Asp  Gly  Pro  Arg  Ser  His  Pro  Tyr  Asn  Phe  Pro  Ala  Gly
253
```

FIG. 20D

```
3410                    3420                    3430                    3440                    3450
  |                       |                       |                       |                       |
TCG GGG GGC TCT ATT CTC CGC TCT TCC TCC ACC CCC GTG CAG GGC
Ser Gly Gly Ser Ile Leu Arg Ser Ser Ser Thr Pro Val Gln Gly
268

3460                    3470                    3480                    3490
                  |                       |                       |                       |
ACG GTA CCG GTG GAC TTG GCA TCA AGG CAG GAA GAG GAG CAG
Thr Val Pro Val Asp Leu Ala Ser Arg Gln Glu Glu Glu Gln
283

3500                    3510                    3520                    3530                    3540
  |                       |                       |                       |                       |
TCG CCC GAC TCC ACA GAG GAA CCA GTG ACT CTC CCA AGG CGC
Ser Pro Asp Ser Thr Glu Glu Pro Val Thr Leu Pro Arg Arg
298

3550                    3560                    3570                    3580
                  |                       |                       |                       |
ACC ACC AAT GAT GGA TTC CAC CTG TTA AAG GCA GGA GGG TCA TGC
Thr Thr Asn Asp Gly Phe His Leu Leu Lys Ala Gly Gly Ser Cys
313

3590                    3600                    3610                    3620                    3630
  |                       |                       |                       |                       |
TTT GCT CTA ATT TCA GGA ACT GCT AAC CAG GTA AAG TGC TAT CGC
Phe Ala Leu Ile Ser Gly Thr Ala Asn Gln Val Lys Cys Tyr Arg
328
```

FIG. 20E

```
                                    3640                       3650                        3660                        3670
                                      |                          |                           |                           |
                                    TTT CGG GTG AAA AAG AAC CAT AGA CAT CGC TAC GAG AAC TGC ACC
                                    Phe Arg Val Lys Lys Asn His Arg His Arg Tyr Glu Asn Cys Thr
                                    343

3680                       3690                       3700                       3710                       3720
              |                          |                          |                          |                          |
            ACC ACC TGG TTC ACA GTT GCT GAC AAC GGT GCT GAA AGA CAA GGA
            Thr Thr Trp Phe Thr Val Ala Asp Asn Gly Ala Glu Arg Gln Gly
            358

3730                       3740                       3750                       3760
                                      |                          |                          |                          |
                                    CAA GCA CAA ATA CTG ATC CTG ATC ACC TTT GGA TCG CCA AGT CAA AGG CAA
                                    Gln Ala Gln Ile Leu Ile Leu Ile Thr Phe Gly Ser Pro Ser Gln Arg Gln
                                    373

3770                       3780                       3790                       3800                       3810
              |                          |                          |                          |                          |
            GAC TTT CTG AAA CAT GTA CCA CTA CCT CCT GGA ATG AAC ATT TCC
            Asp Phe Leu Lys His Val Pro Leu Pro Pro Gly MET Asn Ile Ser
            388

3820                       3830                       3840                       3850
                                      |                          |                          |                          |
                                    GGC TTT ACA GCC AGC TTG GAC TTC TGA TCA CTG CCT TTT
                                    Gly Phe Thr Ala Ser Leu Asp Phe  *  Ser Leu Pro Pro Phe
                                    403
```

FIG. 20F

```
7441 TTTTCACAC ATAGCGGGAC CGAACACGTT ATAAGTATCG ATTAGGTCTA TTTTTGTCTC
7501 TCTGTCGGAA CCAGAACTGG TAAAAGTTTC CATTGCGTCT GGGCTTGTCT ATCATTGCGT
7561 CTCTATGGTT TTGGAGGAT TAGACGGGGC CACCAGTAAT GGTGCATAGC GGATGTCTGT
7621 ACCGCCATCG GTGCACCGAT ATAGGTTTGG GGCTCCCCAA GGGACTGCTG GGATGACAGC
7681 TTCATATTAT ATTGAATGGG CGCATAAATCA GCTTAATTGG TGAGGACAAG CTACAAGTTG
7741 TAACCTGATC TCCACAAAGT ACGTTGCCGG TCGGGGTCAA ACCGTCTTCG GTGCTCGAAA
7801 CCGCCTTAAA CTACAGACAG GTCCCAGCCA AGTAGGCGGA TCAAAACCTC AAAAAGGCGG
7861 GAGCCAATCA AAATGCAGCA TTATATTTTA AGCTCACCGA AACCGGTAAG TAAAGACTAT
7921 GTATTTTTC CCAGTGAATA ATTGTT //
   1 GTTAACAATA ATCACACCAT CACCGTTTTT TCAAGCGGGA AAAAATAGCC AGCTAACTAT
  61 AAAAAGCTGC TGACAGACCC CGTTTTCAC ATGGACCTGA AACCTTTTGC AAGAACCAAT
 121 CCATTCTCAG GGTTGGATTG TCTGTGGTGC AGAGAGCCTC TTACAGAAGT
```

FIG. 21

EPISOMAL VECTORS AND USES THEREOF

This application is a 371 of PCT/EE96/00004, filed Dec. 27, 1996, which is a C-I-P of U.S. application Ser. No. 08/581,269, filed Dec. 29, 1995, abandoned.

FIELD OF THE INVENTION

The invention relates in general to episomal vectors.

BACKGROUND OF THE INVENTION

In lower organisms, such as prokaryotes and budding yeast, replication origins contain welldefined cis-sequences called "replicators" and interaction of these sequences with a specific initiator protein complex leads to the initiation of DNA synthesis in these cells (Jacob et al., 1963; Stillman, 1994 and references therein; DePamphilis, 1993). Extrachromosomal replicators, generally, in addition to their origin function, encode functions that assure equal distribution of replicated molecules (i.e., partitioning) between daughter cells at cell division. For prokaryotic plasmids these partitioning functions are well studied and can be provided by several different mechanisms in bacterial cells (Nordström, 1990). In higher organisms, less is known about mechanisms for partitioning of extrachromosomal replicators. For artificial plasmids in yeast, chromosomal centromeres can provide this function. In metazoan cells, one well studied example of a stable extrachromosomal replicator exists—the latent origin oriP from Epstein-Barr Virus (EBV). The maintenance function of EBV requires the viral replication factor EBNA-1 and a series of binding sites for EBNA-1 termed the family of repeats (FR). A model that has been suggested for the function of the EBNA-1/FR combination is that EBNA-1 bound to FR provides physical retention of the oriP plasmids in the cell nucleus (Krysan et al., 1989).

Papillomaviruses are also capable of stable extrachromosomal replication. Infection and transformation of the cells by papillomaviruses follows single hit kinetics. (Dvoretzky et al., 1980). Papillomavirus genomes are maintained as multicopy nuclear plasmids in transformed cells. The viral life-cycle can be viewed as three stages (Botchan et al., 1986). First, following initial entry, the papillomaviral genome is amplified in the cell nucleus, i.e., viral DNA is synthesized faster than chromosomal DNA and the copy-number is increased. The second stage represents maintenance of the viral DNA at a constant copy-number and latent phase of the viral infection is established. During the third, vegetative, stage of the viral life-cycle viral DNA amplification is initiated again, late proteins are synthesized and viral particles are assembled.

The E1 and E2 proteins are the only viral factors required for initiation of papillomavirus DNA replication (Ustav and Stenlund 1991; Ustav et al., 1991; Yang et al., 1991; Chiang et al., 1992; Kuo et al., 1994). A similar, if not identical, set of cellular replication factors and enzymes, in addition to viral initiator proteins, is utilized by SV40 (Tsurimoto et al., 1990; Weinberg et al., 1990) and BPV-1 (Muller et al., 1994) at the origin of replication to initiate DNA synthesis. Analysis of the essential cis-sequences shows that the BPV-1 minimal origin (Ustav et al., 1993) resembles a typical eukaryotic origin of replication (DePamphilis, 1993) and it has been suggested that this similarity could also be extended to the mechanisms of replication of all papovaviruses (Nallaseth and DePamphilis, 1994; Bonne-Andrea et al., 1995). However, the ability of the papillomaviruses to persist as plasmids distinguishes papillomaviruses from other papovaviruses. It has been known for more than 10 years that BPV-1 replicates in transformed cells as a multicopy nuclear plasmid, which can persist in the tissue culture cells over long periods of time (Law et al., 1981). This indicates that papillomaviruses have efficient mechanisms for segregation, i.e., control of copy-number and partitioning, in the transformed cells.

The role of viral factors, cis-acting sequences and cellular factors in long-term persistence of papillomaviruses, which relates to the segregation functions of viral DNA, is not clearly understood. That is, the regions of the viral genome which specify copy number are not identified in the prior art; nor are the regions of the viral genome which participate with the host cell to ensure proper segregation of the viral genome during partitioning. Much more is understood with respect to the initial amplification stage of the papillomavirus life-cycle.

Bovine Papillomavirus (13BPV) and Human Papillomaviruses (HPVs) persist as stably maintained plasmids in mammalian cells. Transient assays, i.e., on the order of several hours to 3–4 days, have been used to define the minimal origin of replication (MO) which is required for transient replication in BPV (Ustav et al., EMBO J, 10, 4231–4329, 1991) and for several HPV subtypes. Two trans-acting factors encoded by BPV and HPVs, namely E1 and E2, have been identified in transient assays which are necessary to mediate replication in many cell types via MO (Ustav et al., EMBO J., 10, 449–457 (1991); Ustav et al., EMBO J, 10, 4231–4329, (1991); Ustav et al., PNAS, 90, 898–902 (1993).) E1 and E2 from BPV will replicate via the BPV MO and via the MO of many HPV subtypes. (Chiang et al., PNAS, 89, 5799–5803 (1992). E1 and E2 from HPV will replicate via the BPV MO and via the MO of many HPV subtypes. (Chiang et al., PNAS, 89, 5799–5803 (1992). Replication of plasmids containing the above elements is high level but transient in eukaryotic cells. Plasmid loss is rapid in the presence and absence of selective pressure.

The papillomavirus life cycle has been the subject of much research. Different portions of the viral genome have been tested in short-term, i.e., transient, transcription or replication assays. See, for example, Szymanski et al., 1991, Jour. Virol. 11:5710; Vande Pol et al., 1990, Jour. Virol 64:5420; Sowden et al., 1989, Nucl. Acids Res. 17:2959; Stenlund, 1987, Science 236:1666; Sedman et al., 1995, Eur. Jour. Mol. Biol. 14:6218; Haugen et al., 1988, Eur. Jour. Mol. Biol. 7:4245; and Kuo et al., 1994, Jour. Biol. Chem. 269:24058.

The BPV 69% transforming region has been used to introduce the rat preproinsulin gene into mouse cells (Sarver et al., 1981, Mol. Cell. Biol. 6:486).

The PMS1 and PMS2 regions of BPV have been reported to "independently support" extrachromosomal replication of the Tn5 neomycin gene in cells that provide viral factors in trans. PMS-1 (plasmid maintenance sequence-1) is localized within a 521 bp region mapping at positions 6945–7476 of the BPV genome, and PMS-2 has been localized to a 140 bp region within the putative open reading frame for the E1 protein, which maps at positions 1515–1655 of the BPV genome. It has been reported that recombinant plasmids carrying either of the PMS elements are unrearranged and stably maintained at a constant copy number. In addition, E1, E6 and E7 are identified as candidate factors for trans regulation of the plasmid state. See Lusky et al., 1984, Cell 36:391, and Lusky et al., 1986, Jour. Virol. 11:729.

Woo et al., WO94/12629 report a vector containing a papilloma virus origin of replication, the "vector maintenance sequence" described in Lusky et al., 1984, supra, a therapeutic nucleic acid, and an E2 gene sequence or an E1/E2 chimeric gene. Woo et al. suggest that such a vector may be tested for stable episomal maintenance over a period of 2–30 days post-transfection. The "vector maintenance sequence" of Lusky et al., 1984, which is described in Woo et al., is shown herein not to be capable of providing long-term vector persistence.

Mutations in the E2 gene have a pleiotropic effect on viral gene functions, including oncogenic transformation. These effects may be the result of the requirement for E2 expression to regulate viral transcription (see DiMaio and Neary, 1989, The Genetics of bovine papillomavirus type 1 papillomaviruses and human cancer. (Ed. N. Pfister), CRC Press, Boca Raton, Fla.). The BPV-1 E2 protein has been shown to activate viral enhancers in trans (Spalholz et al., 1985, Cell 42:183). The E2 open reading frame has been shown to encode a site-specific DNA binding protein that can bind to several sites within the E2 responsive enhancers 1 and 2 (Androphy et al., 1987, Nature 325:70; Moskaluk et al., 1987, Proc. Nat. Aca. Sci. 84:1215). E2 recognition sites that have been studied to date include the sequence motif ACCN6GGT, (SEQ ID NO: 1) where N is any nucleotide (Hawley-Nelson et al., 1988, Eur. Jour. Mol. Biol. 7:525; Hirochika et al., 1988, Genes Dev. 2:54; McBride, 1988, Eur. Jour. Mol. Biol. 7:553; Moskaluk et al., 1988a, Prc. Nat. Aca. Sci. 85:1826), and it is suggested that E2 binds this palindrome as a dimer (Dostani et al., 1988, Eur. Mol. Biol. Org. Jour. 7:3 807; McBride et al., 1989, Proc. Nat. Aca. Sci. 86:510). Not all of these sites appear to bind E2 with the same strength. Sites having the motif ACCGN4CGGT (SEQ ID NO: 2) appear to bind better than sites that deviate in the fourth and ninth bases (Hawley-Nelson et al., 1988, supra; Moskaluk et al., 1988b, supra). It also appears that some of the target sites for the protein have different capabilities for activation in vivo (Harrison et al., 1987, Nucl. Acids. Res. 15:10267; Haugen et al., 1987, Eur. Jour. Mol. Biol. 6:145; Spalholz et al., 1987, Jour. Virol. 61:2128). Li et al. (1989, Genes & Develop. 510) analyze 17 E2 binding sites in the BPV-1 genome and show that affinities for E2 vary over a 300-fold range. Li et al. also find that the presence of the conserved consensus ACCGN4CGGT (SEQ ID NO: 2) did not necessarily guarantee that the binding site would be stronger than one with a deviant base, and suggest that the presence of this palindrome is not a sufficient parameter for predicting the strength of a binding site.

A truncated form of E2 protein exists which is defective in transcriptional activation and competent in viral replication.

Dowhanick et al., 1995, Jour. Virol. 69:7791, describe an E2 deletion mutant containing residues 1–218 of the protein which is said to retain a DNA replication function, but is defective in transcriptional trans-activation. Also described are several E2 point mutants (331 and 344) which are defective in both transcriptional transactivation and DNA binding.

In addition, subsequent to Applicant's disclosure of E2 point mutants which are defective in transcriptional activation and replication competent in the subject priority document, which E2 mutants are also described in Abroi et al., 1996, Jour. Virol. 70:6169, additional similar, if not identical in some instances, E2 point mutants have been identified. Ferguson and Botchan, 1996, Jour. Virol. 70:4193, describe mutations at amino acids 73 and 74 which retained replication function but failed to activate transcription". Sakai et al., 1996, Jour. Virol. 70:1602, describe three point mutants (R37A, 173A, and W92A) in BPV defective for transcriptional activation but retaining wild type DNA replication activity in transient assays.

One object of the invention is to provide a recombinant vector which, by virtue of the sequences it contains, is stably maintained and thus persists long-term in mammalian cells.

Another object of the invention is to provide a recombinant episomal vector which is stabilized via regulatory sequences which are contained within a relatively small amount of DNA.

Another object of the invention is to provide a cis-acting element which confers long-term stability to a transiently replicating eukaryotic episomal plasmid.

Yet another object of the invention is to provide an episomal genetic element which replicates independently of the host cell chromosomal DNA, and is therefore not dependent upon regulatory control of replication by the host cell genome.

Another object of the invention is to provide stable and reliable plasmid copy number in both G1 and G2 stages of the cell cycle.

Yet another object of the invention is to provide a recombinant vector which is stably maintained at a constant copy number for multiple cell generations.

Another object of the invention is to provide a recombinant vector which is able to persist over a long time period in eukaryotic, particularly mammalian cells, from which can be expressed a therapeutic, prophylactic, or marker gene.

Another object of the invention is to provide a recombinant vector which is not restricted as to its ability to be maintained in a given cell type, but which is stably maintained in any one of numerous diverse mammalian cell types.

Another object of the invention is to provide a recombinant vector containing sequences of viral origin which do not confer oncogenic properties to the transfected host cell, and is therefore safe to use in humans.

SUMMARY OF THE INVENTION

The invention is based on the discovery of a vector system which permits long-term persistence in episomal form in a mammalian cell, and in particular to the discovery of a minichromosomal maintenance element, which element confers stable persistence of extrachromosomal (i.e., episomal) DNA in mammalian host cells.

The invention encompasses a method of obtaining long-term stable production of a gene product of interest in a host cell, comprising providing a host cell containing a vector comprising (A) a minimal origin of replication of a papilloma virus, (B) a minichromosomal maintenance element of a papilloma virus, and (C) a gene encoding the gene product, wherein the vector, when present in a mammalian host cell, persists in the cell for at least about 50 cell generations in dividing cells or for at least about 8 weeks in non-dividing cells under nonselective conditions without an appreciable loss of copy number.

The invention also encompasses a method of obtaining long-term stable production of a gene product of interest in a host cell, comprising providing a host cell containing a vector comprising papillomavirus sequences consisting essentially of (A) a papillomavirus E2 gene, (B) a minimal origin of replication of a papilloma virus,(C) a minichromosomal maintenance element of a papilloma virus, and (D) a gene encoding the gene product, wherein the vector persists in the cell for at least about 50 cell generations in dividing cells or for at least about 8 weeks in non-dividing cells under nonselective conditions without an appreciable loss of copy number.

The invention also encompasses a method of obtaining long-term stable production of a gene product of interest in a host cell, comprising providing a host cell containing a pair of vectors comprising (I) a first vector comprising papillomavirus sequences consisting essentially of (A) a papillomavirus E2 gene, (B) a minimal origin of replication of a papilloma virus, and (C) a minichromosomal maintenance element of a papilloma virus, and (II) a second vector comprising papillomavirus sequences consisting essentially of (A) a gene encoding the gene product, (B) a minimal origin of replication of a papilloma virus, and (C) a minichromosomal maintenance element of a papilloma virus, wherein the vector persists in the cell for at least about 50 cell generations in dividing cells or for at least about 8 weeks in non-dividing cells under nonselective conditions without an appreciable loss of copy number.

The invention also encompasses use of a recombinant vector for obtaining long term stable maintenance of erogenous DNA in a eukaryotic host cell wherein the recombinant vector comprises: a minimal origin of replication of a papillomavirus; a minichromosomal maintenance element of a papillomavirus; and a heterologous DNA sequence encoding an expressible gene.

Preferably, the time period over which the vector persists in the host cell under nonselective conditions without an appreciable loss of copy number is 6 weeks, and most preferably 8 weeks or 12 weeks or longer, or in terms of cell generations, 100 or 120 cell generations or longer.

According to the claimed methods, long-term persistent vectors will include one in which the minichromosomal maintenance element consists essentially of the region of BPV mapping to positions 7590 to 7673; or wherein the minichromosomal maintenance element comprises (BPV E2 binding sites 6, 7 and 8) x, wherein x is 3 to 6 or wherein the minichromosomal maintenance element comprises at least 2 of the 3 E2 binding sites 6, 7 and 8.

The invention therefore also encompasses a recombinant vector for stable long-term persistence of erogenous DNA in a mammalian host cell, the vector comprising a minimal origin (MO) of replication of a papillomavirus, a minichromosomal maintenance element (MME) of a papillomavirus, and a gene encoding a gene product of interest, wherein the vector is defined hereinbelow (1–4).

1. The vector comprising papilloma virus sequences consisting essentially of (A) a minimal origin of replication of a papilloma virus, (B) a minichromosomal maintenance element of a papilloma virus consisting essentially of at least two of the three E2 binding sites 6, 7, and 8, wherein the region of the vector comprising the minimal origin of replication and minichromosomal maintenance element consists of a DNA sequence different from the natural papilloma virus sequence, and wherein the vector, when present in a mammalian host cell which expresses E1 and E2, persists in the cell for at least about 50 cell generations in dividing cells or for at least about 8 weeks in non-dividing cells under nonselective conditions without an appreciable loss of copy number.

2. The vector comprising papilloma virus sequences consisting essentially of (A) a minimal origin of replication of a papilloma virus, and (B) a minichromosomal maintenance element of a papilloma virus consisting essentially of multiple E2 binding sites, wherein the distance between the minimal origin of replication and the minichromosomal maintenance element is less than about 1.0 kb, wherein the vector, when present in a mammalian host cell which expresses E1 and E2, persists in the cell for at least about 50 cell generations in dividing cells or for at least about 8 weeks in non-dividing cells under nonselective conditions without an appreciable loss of copy number.

3. The vector comprising papilloma virus sequences consisting essentially of (A) a minimal origin of replication of a papilloma virus, (B) a minichromosomal maintenance element of a papilloma virus consisting essentially of the region of BPV mapping to about positions 7590–7673 wherein the vector, when present in a mammalian host cell which expresses E1 and E2, persists in the cell for at least about 50 cell generations in dividing cells or for at least about 8 weeks in nondividing cells under nonselective conditions without an appreciable loss of copy number.

4. The vector comprising papilloma virus sequences consisting essentially of (A) a minimal origin of replication of a papilloma virus, and (B) a minichromosomal maintenance element of a papilloma virus consisting essentially of (BPV E2 binding sites 6, 7, and 8)x wherein x is 3–6, wherein the vector, when present in a mammalian host cell which expresses E1 and E2, persists in the cell for at least about 50 cell generations in dividing cells or for at least about 8 weeks in nondividing cells under nonselective conditions without an appreciable loss of copy number.

As used herein, the term "consisting essentially of means that, with respect to papillomavirus sequences, those sequences which are both necessary and sufficient for long-term vector persistence without an appreciable loss of copy number.

In a preferred embodiment of the invention, a vector of the invention will comprise papillomavirus sequences as well as other sequences relating to expression of a gene of interest. The papillomavirus sequences in the vector will preferably consist essentially of a papillomavirus MME and MO, and thus will not contain papillomavirus sequences that are not required for long-term stable persistence in a eukaryotic host cell. The vectors thus advantageously do not contain papillomavirus sequences which are not both necessary and sufficient for long-term persistence in the episomal state. In addition, the vectors do not contain oncogenic sequences which are present in the papillomavirus genome.

In preferred embodiments, the minichromosomal maintenance element of a papillomavirus is from BPV; the minimal origin of replication of papillomavirus is from BPV; the papillomavirus E1 protein is from BPV; the papillomavirus E2 protein is from BPV.

Preferably, the vector further comprises a gene or genes encoding papillomavirus E2 and/or E1 proteins, and the E2 gene most preferably encodes a mutant form of E2 which is a point mutant that is replication competent but defect in transcriptional activation. As used herein, a "point mutant" may refer to either a single amino acid change, or several individual amino acid changes (2, 3, 4 etc.) which together confer the desired phenotype. A point mutant may be an amino acid substitution or a deletion or insertion.

One particularly useful form of a vector of the invention is a recombinant vector or vector system for stable persistence of erogenous DNA in a host cell, the vector comprising a minimal origin of replication of a papillomavirus, a minichromosomal maintenance element of a papillomavirus, and one or both of the papillomavirus E1 and E2 genes.

The invention also encompasses a mutant form of a papillomavirus E2 protein wherein the replication function of the protein is competent and the transcriptional activation function of the protein is defective, wherein the mutant form of E2 protein differs from the wild-type E2 in a nucleotide point mutation which translates into an amino acid substitution.

Preferred E2 point mutants are mutated in an alpha helical domain, for example in alpha helix 2 or 3, as defined herein.

Additional preferred E2 point mutants useful according to the invention are R37A, E74A, and D 122A and D143A/R172C.

A particularly striking feature of the invention is that the stable vectors of the invention are not restricted to the host cell specificity of papillomavirus. This release from the natural papillomavirus host cell type restriction has been achieved by removing key genetic elements of the papillomavirus genome from their native context; for example, expression of the papillomavirus genes encoding E1 and E2 proteins is not controlled by the promoters that are native to these genes, but rather the E1 and E2 genes are placed under the control of non-native, i.e., heterologous promoters, which are either functional in a broad range of mammalian cells or tissues or are cell- or tissue-specific.

It is preferred according to the invention that the expressible papillomavirus gene encoding E1 or E2 include a structural gene encoding E1 or E2 operatively associated with regulatory sequences for expression of the structural gene in a host cell. Such regulatory sequences will include a promoter and/or may optionally include an enhancer. The promoter is preferably a promoter that is non-native (i.e., heterologous) to the E1 or E2 structural gene. The promoter is may be functional in more than a single tissue type, i.e., one that is able to initiate transcription in a broad range of tissue types, and therefore unrestricted with respect to its tissue specificity. Alternatively, the promoter may be functionally restricted to a single tissue type, and therefore tissue-specific.

As used herein, tissue-specific and cell-type-restricted both refer to wherein a promoter is operable substantially in the same tissue-type or cell-type.

Preferred promoters comprise one of the thymidine kinase promoter and a strong promoter such as the SRalpha promoter. It is expected that a vector of the invention which includes tissue-specific regulatory elements operatively associated with the E1 and/or E2 genes will be capable of long-term persistence only in those cell types in which the regulatory elements are functional.

In its most useful form, a recombinant vector of the invention will include an expressible gene of interest.

A vector of the invention which contains an expressible gene of interest contains not only a structural gene encoding a protein or RNA of interest, but also is operatively associated with regulatory sequences for expression of the structural gene in a host cell. Such regulatory sequences may include not only a promoter, but also additional regulatory sequences such as an enhancer, splice sites, and polyadenylation sequences. These regulatory elements that control expression of the structural gene promoter may be regulatory elements that are native to the structural gene (i.e., the control sequences that are naturally associated with these genes in their native environment), or they may be non-native to the structural gene, and therefore heterologous regulatory elements. These elements, particularly the promoter, may be functional in more than a single tissue type or may be functionally restricted to a single tissue.

It is expected that a vector of the invention which includes a tissue-specific regulatory element that is operatively associated with a structural gene of interest will express that gene of interest only in those host cell types in which the regulatory elements are functional (i.e., specific).

It is preferred according to the invention that the host cell type-restricted expression (i.e., tissue-specificity) of the structural gene of interest be coordinated with the tissue-specificity of the regulatory elements operatively associated with the E1 and E2 genes. That is, one may envision that the tissue-specificity of E1, E2, and structural gene of interest is the same. Alternatively, the tissue-specificity of E1 and E2 gene expression may be broader than the tissue-specificity of expression of the gene of interest, resulting in a broad host cell type range for long-term persistence of a vector of the invention, and a more limited host cell type range for expression of the gene of interest. Alternatively, the tissue-specificity of E1 and E2 gene expression may be quite limited (for example, to a single cell type), and the tissue-specificity of expression of the gene of interest broad or unlimited, resulting in a limited host cell type in which a vector of the invention can persist long-term, which in turn is the limiting factor in determining the type of host cell in which the gene of interest is expressed.

In another preferred embodiment of a vector of the invention, the vector also includes a bacterial host cell origin of replication and a gene encoding a selectable marker for preparation of vector DNA in a bacterial host cell.

The invention also features host cells containing the vectors herein described, such host cells being most preferably being eukaryotic, and of mammalian origin, such as of muscle, gut, or brain origin.

The invention also features a method of manufacture of a vector, which method includes culturing a host cell containing a vector described herein. It is particularly preferred that such manufacture occur in a lower eukaryotic cells, e.g., yeast or insect, or prokaryotic cells, e.g., bacterial cells such as E.coli or Salmonella. Therefor, the vector will further include an origin of replication of yeast, insect or bacterial origin, and one or more genes encoding a selectable marker, e.g., a gene encoding kanamycin resistance, for selection of cells containing the vector.

The invention also features a method of obtaining stable expression of a gene of interest in a cell, comprising providing a host cell as described above. The invention also features methods of treating a disease stemming from a genetic defect, comprising administering a therapeutically effective or a prophylactic amount the vector of the invention to a patient afflicted with the disease.

The invention also includes use of a recombinant vector of the invention in the treatment of a disease.

The invention also encompasses a gene delivery system comprising a vector of the invention in combination with a gene delivery vehicle, which may be of viral or non-viral origin.

The invention also encompasses a method of producing a protein or RNA of interest in a host cell or a transgenic animal, comprising culturing a host cell under conditions which permit production of the protein of interest, or providing a transgenic animal which produces the protein, as described herein.

The invention also encompasses a mammalian model of disease, for screening of drugs to treat the disease or for testing of therapeutic or prophylactic regimes, the mammalian model comprising a transgenic animal whose cells contain a vector of the invention.

The invention also encompasses a transgenic animal containing an episomal vector as described herein, the vector encoding a protein of interest.

As used herein, a "transgenic animal" refers to an animal, preferably a mammal, which contains in some, but not necessarily all, of its cells an episomal vector, as described herein.

The invention also features kits for providing stable persistence of a vector in a host cell, the kit comprising a vector or a host cell as described herein and packaging materials therefore.

A kit of the invention may also include a mutant E2 protein as described herein or a gene encoding this protein, wherein the E2 mutant is thus provided for stable persistence of a vector in a host cell.

Uses and Advantages of the Invention are as Follows.

The invention is useful in in vivo and ex vivo human gene therapy where correction of inherited or acquired genetic defects is desired. The invention also is useful in vaccination protocols where resistance or immunity to infectious pathogens, such as HIV, Hepatitis C Virus, Hepatitis B virus, Herpes virus, parasitic pathogens such as Tuberculosis and Leishmaniasis, and protozoans such as ameobic dysentery, is desired, or the elimination or induced quiescence of aberrant cells, such as cancer cells, is considered beneficial.

Recombinant vectors of the invention are useful in that they permit persistent expression of a therapeutic gene in both dividing and non-dividing cells; for example, in differentiated cells, such as those in brain, and muscle.

Recombinant vectors of the invention are also useful for high level transient expression in cells where desired, such as for cancer therapy or in vivo vaccination.

Both in vivo and ex vivo gene therapy strategies are possible with this vector system, including stable, multicopy gene maintenance and expression, in haemopoietic and other stem cells, and in the committed and differentiated progeny of these cell types.

For human gene therapy, uses of the recombinant vectors of the invention are not limited in terms of delivery of the vector to a cell. That is, vectors of the invention may be delivered to a cell via non-viral or viral delivery systems. Delivery systems of non-viral origin include those which employ cationic liposomes, where vector size constraints do not limit the nature and number of plasmid vector components. Delivery systems of viral origin include viral particle-producing packaging cell lines as transfection recipients for the above E1/E2/MO/MME-containing plasmids into which viral packaging signals have been engineered, such as those of adenovirus, herpes viruses and papovaviruses.

Recombinant vectors of the invention also are useful in transgenesis, including production of transgenic animals via pronuclear injection, or embryonic stem cell transfection and embryo chimera generation.

Recombinant vectors of the invention also are useful for preparation of cell factories for stable, high level expression of proteins of therapeutic value in cultured mammalian cells.

Further features and advantages of the invention will become more fully apparent in the following description of the embodiments and drawings thereof and from the appended claims.

DESCRIPTION OF THE DRAWINGS

Before describing the invention in detail, the drawings will be briefly described.

FIG. 8 (Parts a–i) represents a comparison of the stable replication modes of BPV origin containing plasmid and chromosomal DNA in the CHO4.15 cells. BrdU labeling of the CHO4.15 cells carrying stably replicating pNeoBgl40 was done for a) and e)—3.5, b) and f)—9.5, c) and g)—15.0 and d) and h, i)—24 hours, respectively. Episomal—a), b), c), d) and total chromosomal DNA —e), f), g), h, i) were prepared at respective time points and analyzed as described in Materials and Methods. CsCl gradients were aliqoted, denatured, renatured and loaded onto the nylon filters by slot-blotter and hybridized with radioactive BPV-1 origin probe for episomal DNA and with radioactive total CHO DNA for genomic DNA gradients. Intensity of hybridization was quantitated by use of the Phosphoimager.

FIGS. 20, 20A–20F provides the nucleotide and amino acid sequence of the BPV1 E2 sequence (SEQ ID NO: 3). The positions which were mutated to produce E2 point mutants are designated as * and are referred to in the text by amino acid residue. The E2 protein sequence (SEQ ID NO: 4) begins at the MET indicated as 1.

FIG. 21 provides the nucleotide sequence of the BPV upstream regulatory region (SEQ ID NO: 5). The MME sequence is located between positions 7475(Cla 1 site) and the Hpa 1 site (7947).

DESCRIPTION

The invention is based on the recognition that DNA replication in papillomavirus from the minimal origin (MO) per se is not sufficient for long-term persistence, but that in addition another viral sequence is required. This sequence, termed herein a minichromosomal maintenance element (MME) comprises a binding site for proteins which are essential for papillomavirus replication. Although the MME sequence may include binding sites for replication proteins that are of viral or human origin, for example, in BPV, the sequence appears to be dependent on viral proteins E1 and E2, and is specifically bound by the viral E2 protein, when the sequence is linked to the minimal origin sequence.

The invention thus is based on the discovery of a cis-acting element, referred to herein as a minichromosomal maintenance element (MME), which confers long-term stability to a transiently replicating eukaryotic episomal plasmid. An MME is distinct from a minimal origin of replication (MO), and is required in addition to an MO for long-term plasmid persistence in a host cell.

RECOMBINANT VECTORS OF THE INVENTION

The invention encompasses a genetic construct comprising a single plasmid containing the MO and MME sequences (MO/MME vectors) and a cloning site for insertion of a gene of interest. The invention also encompasses a genetic construct comprising a single vector containing genes encoding E1 and E2 plus MO and MME sequences (E1/E2/MO/MME vectors) and a cloning site for insertion of a gene of interest. In its most useful aspect, the invention features the above described plasmids wherein a gene of interest also is contained in the plasmid.

Optionally, vectors of the invention may include multiple cloning site cassettes and selectable markers conferring drug resistance to mammalian and bacterial cells, and reporter genes such as lacZ FIG. 7). These vectors can be used as stable expression vectors in a wide range of both dividing and non-dividing (post-mitotic) cell types.

Figure 9:
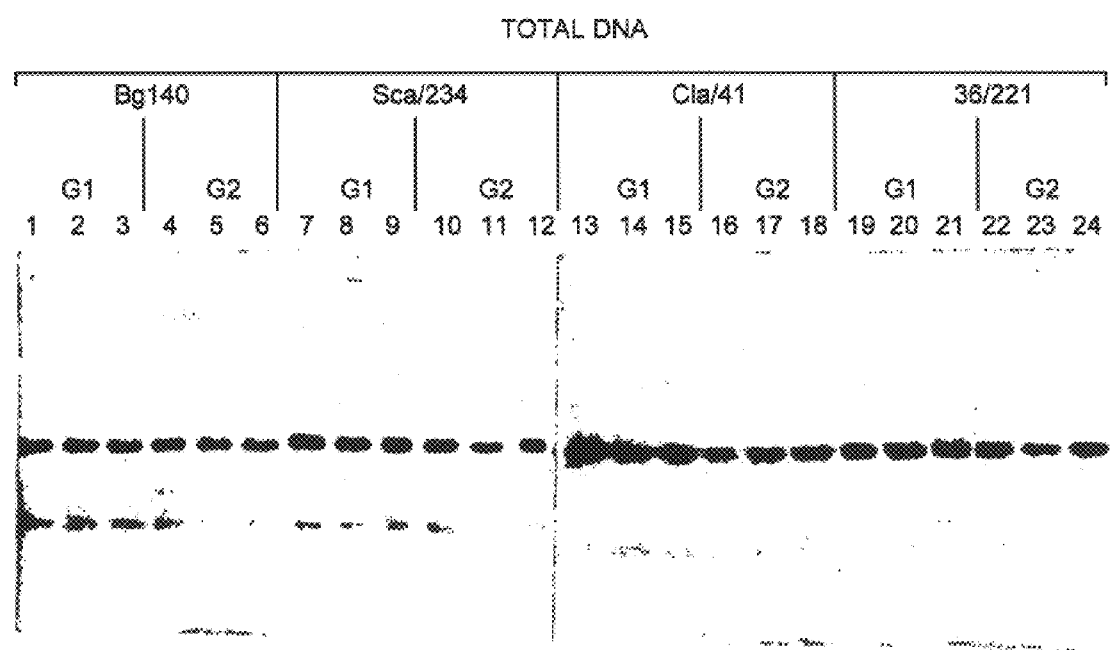
FIG. 9 shows the copy number of BPV-1 origin-bearing plasmids is similar in G1 and G2 phases of the cell cycle. Southern blot analysis of plasmid copy number in G1 and G2 phases of the cell cycle. Derivatives of CHO4.15 cell line with stably, extra chromosomally replicating BPV-1 origin-containing plasmids were arrested in G1/S with mimosine or hydroxyurea and in G2 with hydroxyurea, followed by Hoecsht 33342 treatment. Arrest was verified with FACS analysis, total DNA was extracted and an equal amount of DNA was loaded onto each lane. Analysis of four different established cell lines is shown on the figure with 3 parallels for each cell cycle arrest.

An important property of a plasmid containing these determinants is that replication of this episomal plasmid is not subject to regulation by the cellular controls which regulate host genome replication; that is, replication occurs independently and is under E1/E2 control in the S-phase of the cell cycle. (FIG. 8). The initiation of E1/E2-dependent replication of MO/MME-containing plasmids is random in the cell cycle but over-replication does not occur; stable copy number is maintained in both G1 and G2. (FIG. 9).

Vectors of the invention are safe to use in human cells and impart no known oncogenic properties to recipient cells. All papilloma-encoded oncogenic sequences have been deleted. (FIGS. 2 and 3).

Definitions

As used herein, "papillomavirus" refers to a member of the papilloma family of viruses, including but not limited to bovine papillomavirus (BPV) and human papillomavirus (HPV).

"Minimal origin of replication" (MO) refers to a minimal cis-sequence within a papillomavirus that is necessary for initiation of DNA synthesis. The MO of BPV-1 is located at the 3' end of the upstream regulatory region within a $60\mu$ fork, corresponding to a 52 base pair DNA fragment (7928–7947/1–25) including an AT-rich region, a consensus sequence to which all papilloma viral E2 proteins bind, and an E1 protein binding site spanning nucleotide 1. The MO of HPV is located in the URR fragment (for example, in HPV11 at nt 7072–793 3/1–99) (Chiang et al. PNAS 1992).

In a transient replication assay, the efficiencies of replication of plasmids bearing a Minimal Origin (MO) and a full size Origin of Replication are equal. Only two viral proteins, E1 and E2, are required for stable replication of the full size Origin. An observation which led in part to the discovery which forms the basis of the invention is that the minimal origin of replication (MO) is absolutely essential, but it is not sufficient to stably maintain the plasmids in an episomal state; additional elements in the Upstream Regulatory Region are not only required, but are sufficient, for stable persistence of the plasmids (FIG. 2).

"E1" refers to the protein encoded by nt 849–2663 of BPV subtype 1; or to nt 832–2779 of HPV of subtype 11, or to equivalent E1 proteins of other papillomaviruses, or to functional fragments or mutants of a papillomavirus E1 protein, i.e., fragments or mutants of E1 which possess the replicating properties of E1.

"E2" refers to the protein encoded by nt 2594–3837 of BPV subtype 1; or to nt 2723–3823 of HPV subtype 11, or to equivalent E2 proteins of other papillomaviruses, or to functional fragments or mutants of a papillomavirus E2 protein, i.e., fragments or mutants of E2 which possess the replicating properties of E2. Numerous E2 mutants are described herein which are defective in the E2 transcriptional activating activity and competent in the replicating ability.

"Minichromosomal maintenance element") (MME) refers to a region of the papilloma viral genome to which viral or human proteins essential for papilloma viral replication bind, which region is essential for stable episomal maintenance of the papilloma viral MO in a host cell. Preferably, the MME is a sequence containing multiple binding sites for the transcriptional activator E2, although the MME also may be a sequence containing host cell factor binding sites. An MME is most likely to be located in the upstream regulatory region of the viral genome. The MME in BPV is herein defined as the region of BPV located within the upstream regulatory region which includes a minimum of about six sequential E2 binding sites, and which gives optimum stable persistence with about ten sequential E2 binding sites, and which may include as many as about 20–30 or as many as about 50 sequential E2 binding sites. The sequential binding sites which constitute the MME need not be identical in sequence, but must be able to bind E2. In addition, between each sequential binding site in the MME, there may be spacer nucleotides, for example, 6 nucleotides, sufficient to insert a restriction enzyme site. The spacer nucleotides may be absent from the MME or may extend to a length of 10, 20 or even 50 nucleotides, so long as the binding of E2 to each separate binding site is not disrupted by the presence of the spacer.

Figure 5:
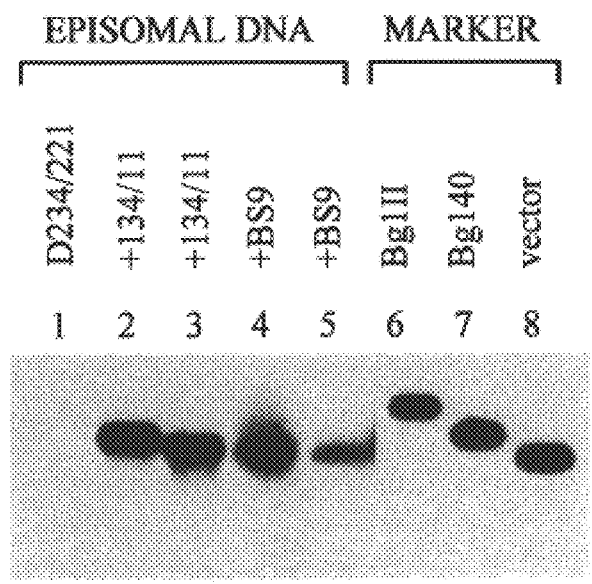
FIG. 5 shows restoration of stable replication of the plasmids by an MME consisting of oligomerized E2 binding sites. Low molecular weight DNA was extracted from the G418 resistant cells and linearized with HindIII (lanes 1–4) or with XbaI (lane 5). Lane 1 represents analysis of the DNA from the cells transfected with original D234/221 mutant with deleted MME. Insertion mutants with E2REI (BPV nucleotides 7611–7673) cloned into D234/221 adding back 18 and 9 E2 binding sites restored stable replication of the plasmid (lanes 2,3). Mutant with oligomerized 10 E2 binding sites cloned into D234/221 (lane 4) and mutant with deleted PMS1 with inserted 10 oligomerized E2 binding sites (lane 5) replicate in the long term assay. Lanes 6–8 contain 100 ng of linearized respective marker DNA.

The Minichromosome Maintenance Element (MME) of BPV comprises multiple, binding sites for the E2 protein (FIG. 3). 10–20 tandem repeats of E2 binding sites impart greater stability and higher plasmid copy number (approx. 30 copies per cell, FIG. 4) in cells expressing the BPV (or HPV) E1 and E2 proteins. (FIG. 5). It is believed that MME/MO-bearing plasmids function in a wide range of eukaryotic cells including rodent, monkey and human cells, and in almost any tissue type.

The MME confers (E1+E2)-dependent stable replication upon plasmid transfection into a host cell line expressing both E1 and E2. It is observed that neither E1 nor E2 alone is sufficient to permit MME-mediated plasmid stability (FIG. 6). E1 and E2 can be provided to the plasmid either in cis or in trans (i.e. from integrated E1 and E2 expression vectors or from the same episomal plasmid).

"E2 binding site" refers to the minimum sequence of papillomavirus double-stranded DNA to which the E2 protein binds. This binding site is in most papillomaviruses located in the upstream regulatory region in BPV and HPV. In BPV, the E2 binding site is a palindromic 12 nucleotide sequence (ACCN6GGT, (SEQ ID NO: 1) where N is any nucleotide) which is repeated approximately 10 times within the URR. The affinities of the 10 E2 binding sites for E2 varies among the binding sites in the BPV URR, with site 9 (ACCGN4CGGT, (SEQ ID NO.: 2) where N is any nucleotide) being the strongest E2 binding site.

A "host cell" which is stably transformed according to the invention may be any prokaryotic or eukaryotic cell, an is preferably a mammalian cell, and most preferably a human cell. The cell may be derived from any tissue, for example, muscle, nerve tissue, etc.

When the E1 and/or E2 genes are located in cis with respect to the MO and MME, this refers to a genetic context in which one or both genes are located on the same episomal element or the same vector as the MO or MME. In contrast, when the E1 and/or E2 genes are located in trans with respect to the MO and MME, this refers to a genetic context in which the E1 and/or E2 genes are not located on the same episomal element as the papilloma MO or MME, such as a context in which the E1 and/or E2 genes are integrated into the host cell chromosome or the E1 and E2 genes are carried on a separate (non-contiguous) genetic element (vector or episome).

"Stable maintenance" or "long-term persistence" refers to two characteristics of vectors of the invention. First, it refers to the ability of a vector according to the invention to persist or be maintained in undividing cells or in progeny cells of dividing cells in the absence of continuous selection over the long-term. As used herein, "long-term" refers to a period of time that is longer than at least about 5 weeks, for example longer than 8 weeks (where a given cell doubling time is about 16 hours). Of course, for a longer or shorter cell doubling time, the definition of "long-term" changes accordingly. Second, it refers to the ability of a vector according to the invention to persist without an appreciable loss of copy number from one cell division to the next. In determining whether a given vector is capable of long-term persistence, the recombinant vector may be introduced into the host cell under conditions in which the vector is selected for, when the selection conditions are thereafter removed, the copy number of the recombinant vector nevertheless remains constant and reliable thereafter; for example, in non-dividing cells, a vector of the invention persists for a period that is longer than at least 5 weeks, for example, 6 weeks, 8 weeks, 12 weeks or longer, for a host cell which doubles in about 16 hours. A vector of the invention is capable of persisting, in dividing cells, over about at least 50 generations, 60 generations, 80 cell generations, or 120 cell generations or longer under non-selective conditions without an appreciable loss of copy number. We have found that loss of copy number over 80 generations of cell doublings is less than about 10% (over 80 generations). Therefore, loss of copy number from one cell generation to the next is less than about 0.125% or about 0.1%. Therefore, the vectors of the invention are not subject to an appreciable loss of copy number from one cell generation to the next. In contrast, "short-term persistence" of a plasmid in a host cell refers to the inability of a plasmid to persist in a host cell long-term, as defined herein, without an appreciable loss of plasmid copy number, as defined herein.

A "gene of interest" refers to a gene encoding a gene product of interest such as a protein of interest or an RNA of interest. A "protein of interest" refers to any therapeutic, prophylactic or marker protein useful according to the invention. In addition to any therapeutic protein selected for a treatment using a vector of the invention, a therapeutic protein may include a cell or viral surface antigen to which an immune response may be elicited when used in a vaccine.

"Heterologous" or "erogenous" gene refers to a coding sequence that is introduced into a host cell on a vector of the invention. The coding sequence may be identical to a sequence contained within the host cell, or it is most likely not identical to a host cell sequence.

"Heterologous promoter" refers to a promoter that is not the natural (or homologous) promoter that initiates transcription from the gene with which it is associated, whether that gene be the gene encoding a protein of interest or the genes encoding the E1 and E2 proteins. A "strong" promoter, with respect to E1 and E2 expression, refers to a promoter which supports overexpression of the E1 and/or E2 gene to an extent that the vector is maintained in sufficiently high copy number so as to make the host cells unhealthy. An example of a strong promoter is the SR-alpha promoter; other strong promoters will provide about the same level of expression of a reporter gene in an assay for quantitating gene expression and thus promoter strength, e.g., a betagalactosidase assay.

As explained hereinabove, a vector useful in the invention will contain papillomavirus MO and MME sequences, as defined herein, and a cloning site for insertion of a gene of interest, and will require the presence of the papillomavirus E1 and E2 proteins for long-term persistence in a host cell. The E1 and E2 proteins are effective in trans in the cell and therefore the genes encoding these proteins may be present in trans with respect to the vector, or they may be present in cis, i.e., within the vector DNA. In addition to the above-described sequences, a vector useful in the invention may contain a heterologous gene encoding a protein of interest and also may contain sequences for regulation of that gene.

Described below are experiments in which the BPV MME is localized and characterized. This experimental strategy also is useful for localizing and characterizing the HPV MME. Following the description of the BPV MME characterization is a description of the components of vectors of the invention; i.e., heterologous genes of interest in vectors of the invention, heterologous regulatory sequences, e.g., promoters, which may be used to direct E1 and E2 gene expression and to direct heterologous gene expression, E2 mutants useful according to the invention, host cells useful in the invention, and delivery vehicles useful for delivering vectors of the invention to host cells. The Examples provided hereinbelow describe specific embodiments of the invention and are meant to illustrate and not to limit the applicability of the invention.

Localization of BPV MME Sequence

We have constructed a cell line CH04.15 expressing constitutively the viral proteins E1 and E2, that are required for initiation of viral DNA replication. It has previously been demonstrated that the minimal origin of replication and the viral E1 and E2 proteins are sufficient for plasmid replication. It is demonstrated herein that the E1 and E2 viral proteins are not only necessary, but are sufficient when coupled with the MME for long-term episomal persistence.

Using the cell line CH04.15 it is shown herein that the BPV-1 minimal origin of replication (MO) is absolutely necessary, but is not sufficient for stable extrachromosomal replication of viral plasmids. By deletion and insertion analysis, an additional element (Minichromosome Maintenance Element—MME) in the Upstream Regulatory Region of BPV-1 has been identified which assures stable replication of the MO containing plasmids. This element is composed of multiple binding sites for the transcriptional activator E2. MME appears to function in the absence of replication but requires E1 and E2 proteins for activity. In contrast to EBV or EBV oriP-containing plasmids, for example, stably maintained BPV-1 plasmids are not subject to once-per-cell cycle replication as determined by density labeling experiments. These results indicate that papillomavirus episomal replicators replicate independently of the chromosomal DNA of their hosts.

Construction of cell lines expressing E1 and E2 proteins

The E1 and E2 proteins of BPV-1 are necessary for initiation of DNA replication from the viral origin of replication. Expression of these two proteins from heterologous expression vectors allows replication of a minimal origin in transient replication assays (Ustav and Stenlund, 1991; Ustav et al., 1991). However, due to the lack of persistence of the transfected expression vectors, replication can not be monitored for more than few days after transfection.

To determine whether additional trans-acting factors or cis-acting elements are required for long term persistence of the viral DNA, continuous expression of these two factors has to be assured. We therefore constructed several cell lines constitutively expressing the E1 and E2 proteins. Expression of these proteins was directed from integrated constructs for E1 protein from CMV promoter (cell line CH0212) and for E2 protein from HAP 70 promoter (cell line CH049). In the cell line CHO4.15 which expresses both E1 and E2, the E1 protein was expressed from SRα-promoter and the E2 protein from HSP 70 promoter. Selection of the respective cell lines and amplification of the expression units of interest was achieved by utilizing the glutamine synthesize mini gene from the PSVLGS. 1 plasmid according to the protocol described earlier (Bebbington and Hentschel, 1987). Expression of E1 and E2 was identified by immunoprecipitation using specific rabbit polyclonal sera (data not shown) and by in vivo replication assays. The three cell lines and the parental CHO cells were transfected with the BPV-1 origin containing plasmid pUC/Alu in combination with E1 and E2 expression vectors. The cell line CHO4.15 which expresses both E1 and E2, supports replication of the origin plasmids in the absence of erogenous E1 and E2. The E2 expressing cell line, CHO49, supports replication in the presence of an E1 expression vector, but fails to do so without erogenous E1. The E1 expressing cell line, CHO212, supports replication only in the presence of an E2 expression vector. In the parental CHO cell line, co-expression of both E1 and E2 is required for replication. No replication of pUC/Alu can be detected in the absence of E1 and E2.

Described below are experiments which demonstrate the trans and cis-acting elements which are not only necessary but are sufficient for long-term episomal persistence. The E1 and E2 proteins are both necessary and sufficient for stable replication of the BPV- I origin containing plasmids. In addition, the BPV-I URR contains sequences which are not only required, but are sufficient for long-term replication of the papilloma-derived episome.

This experimental strategy and procedure also may be used to determine the exact location in HPV of the MME, simply by substituting HPV for BPV, and testing regions of the HPV genome. Such testing would begin with the URR of BPV, which region includes binding sites for E2 and for cellular factors involved in replication.

The experimental protocol used for defining the BPV MME was as follows.

To determine what viral trans-acting factors and cis-sequences were required for long term replication of BPV-1, we used the CHO4.15 cell line which constitutively expresses both the viral E1 and E2 proteins. Different fragments of BPV-1 were cloned into the vector pNeo5' (Lusky and Botchan, 1984 ). This plasmid provides amino glycoside 3'-phosphotransferase as a marker for selection of the cells in the presence of geneticine (G418). We used a 2.5 kb BglII fragment from the BPV-1 genome (nucleotides 6946–1515) as a starting fragment. This fragment contains the URR including the E2 dependent transcriptional enhancer, the minimal origin of replication and part of the early ORF's (construct 12, FIG. 2A). This plasmid, in parallel with a minimal origin fragment in the same backbone (construct 13, FIG. 2A), were transfected into the CHO4.15 cell line by electroporation and processed according to the scheme in FIG. 1A.

Figure 1A:
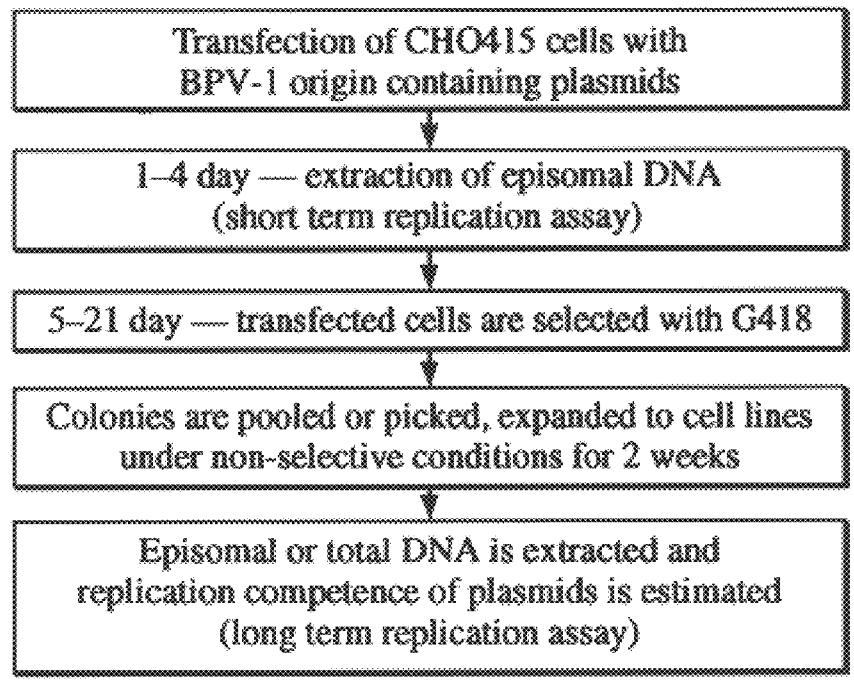
FIG. 1A is a scheme of the experimental protocol.
Figure 1B:
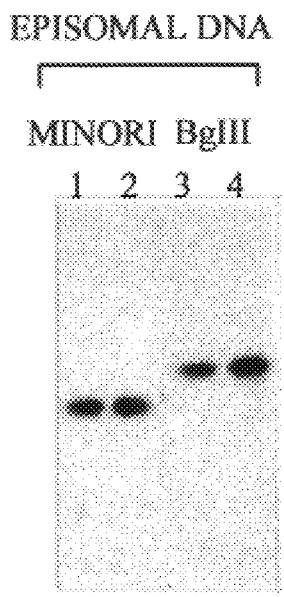
FIG. 1B is a short term replication assay for the plasmids in the CHO4.15 cells. Low molecular weight DNA was extracted from the CHO4.15 cells transfected with the plasmids containing minimal origin or 2.5 kb BglII fragment and analyzed by Southern blotting after digestion with DpnI and linearizing enzyme XbaI (lanes 1, 2) and HindIII (lanes 3, 4). Lanes 1, 2—episomally replicating minimal origin containing plasmid DNA extracted 36 and 60 hours after transfection and lanes 3,4—episomal DNA extracted 36 and 60 hours after transfection with the plasmid containing 2.5 kb origin fragment.

In FIG. 1A, both transient and long-term plasmid persistence was determined. A portion of the transfected cells were used after plating for analysis of transient replication. The remaining portion of the cells were selected in the presence of G418 for three weeks, colonies were then pooled or picked and grown under nonselective conditions for two additional weeks, to give a total of five weeks, at which time low molecular weight DNA was harvested and analyzed for the presence of replicated plasmid. The ability of the origin-containing plasmids to replicate extra chromosomally in transient and long term replication assays was examined by Southern analysis of the episomal DNA (see Materials and Methods for details). The two plasmids containing the 2.5 kb BglII fragment and the minimal origin respectively, replicated to comparable levels in the transient replication assay (FIG. 1B). After selection in the long term replication assay, however, the result was very different. While the plasmid containing the 2.5 kb BglII fragment could be readily detected in episomal form, the minimal origin containing plasmid could not be recovered (compare lanes 12 and 13, FIG. 2B). These results showed that sequences present in the larger plasmid, but absent in the plasmid containing only the minimal origin were required for long term replication, and that an activity in addition to replication was required for stable persistence of a plasmid in the CHO4.15 cells. These results also indicated that it was possible to maintain BPV origin containing plasmids for an extended period of time (e.g., five weeks) without the regulatory circuit that the viral genome can provide.

Figure 2A:
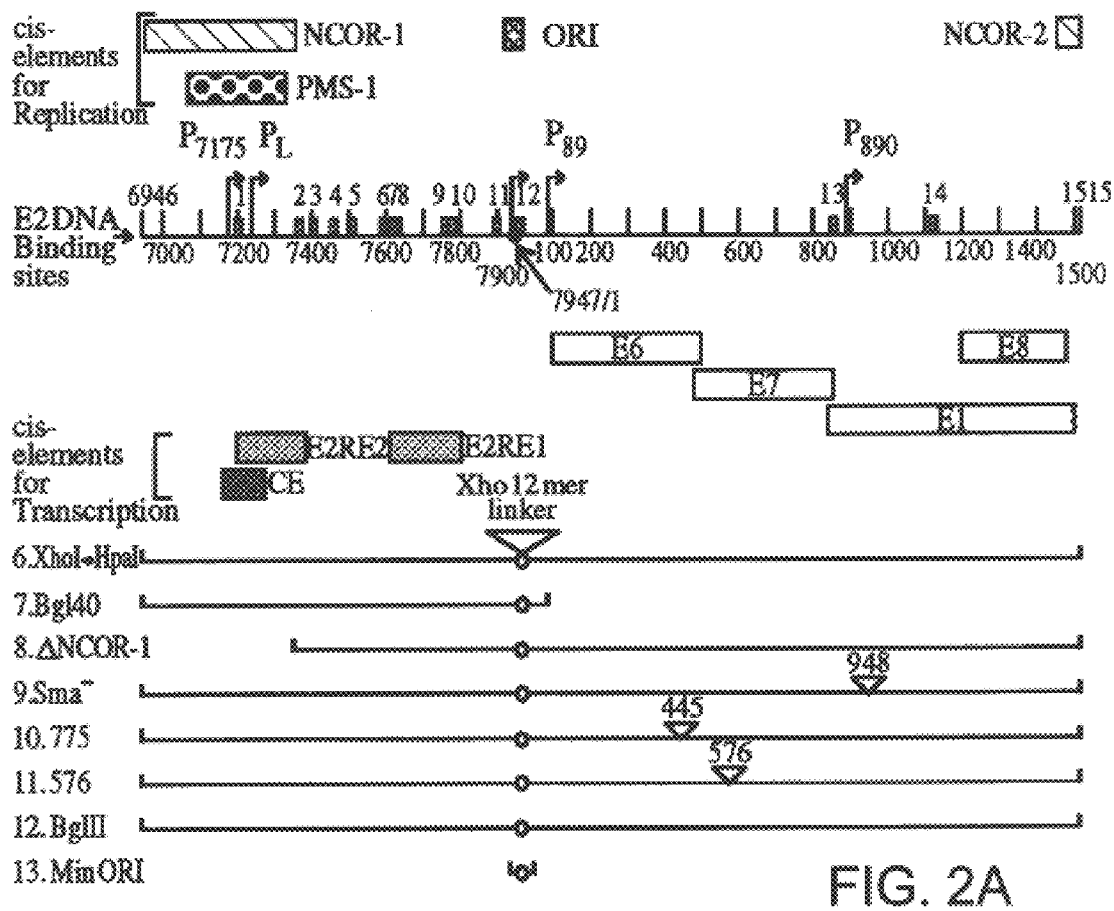
FIG. 2A stable replication of the BPV-1 origin containing plasmids in the CHO4.15 cell line. Representation of the BPV-1 fragment (BPV nucleotides 6945–1515) used in this experiment. The respective mutants in this fragment are depicted and are further described in Materials and Methods. The following genetic elements are indicated: NCOR-1 and 2—Negative Control Of Replication 1 and 2; PMS-1—Plasmid Maintenance Sequence; ORI—minimal origin of replication; E2RE1 and E2RE2—E2 responsive enhancer 1 and 2; CE—constitutive enhancer; E1, E6, E7 and E8—respective ORF-s; $P_{7175}$, $P_L$, $P_{89}$, $P_{890}$—respective promoters; boxes indicate location of 14 E2 binding sites in this fragment.
Figure 2B:
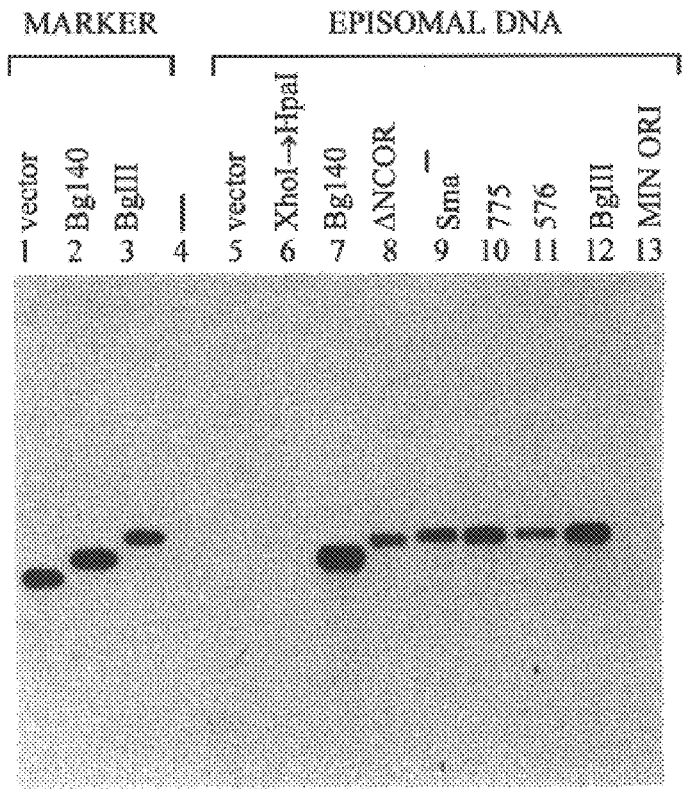
FIG. 2B is a southern blot analysis of stable cell lines for the presence of episomal plasmids. The marker lanes 1, 2, 3—contain 100 pages of linearized vector pNeo5', pNeoBgl40 and pNeoBglII, respectively. Low molecular weight DNA was extracted from CHO4.15 cells after transfection and G418 selection (see Materials and Methods for details). The plasmids used were the vector plasmid pNeo5' (lane 5), pNeoXhoI→HpaI with disrupted E1 protein binding site (lane 6), pNeoBgl40 (lane 7), pNeoΔNCORI with deleted Negative Control Region (lane 8), mutants Sma⁻' 775 and 576 with disrupted 5'-part of E1, E6 and E6/E7 ORFs respectively (lanes 9–11), the wild type pNeoBglII (lane 12), and the minimal origin containing plasmid pNeoMO (lane 13).

To determine what sequences within the BglII fragment were responsible for maintenance in the long term assay, we generated mutations within that fragment and assayed these plasmids for maintenance. Initially, we generated mutations in the sequences suggested previously to have effects on replication. The BPV-1 BglII fragment contains coding sequences for three potential proteins, E6, E7 and the N-terminal part of the E1 protein. Mutations which interrupted E1 ORF, E6 ORF and E6/7 ORF (Lusky and Botchan, 1985; Schiller et al., 1984; Berg et al., 1986)—construct 9 (pNeo Sma⁻), construct 10 (pNeo775), construct 11 (pNeo576), respectively and in addition a deletion removing all coding sequences—construct 7 (pNeoBgl4O), were introduced into the pNeo5' (FIG. 2A). None of these mutations had a detectable effect on maintenance (compare lane 12 with lanes 7, 9, 10 and 11 FIG. 2B) indicating that the coding sequences contained within the BglII fragment were dispensable. Consequently the E1 and E2 are the only viral gene products required for maintenance.

It has been suggested previously that BPV-1 URR contains two partially overlapping cis-regulatory control elements for stable replication, termed Plasmid Maintenance Sequence (PMS-1) (Lusky and Botchan, 1984) and Negative Control of Replication (NCOR-1) (Roberts and Weintraub 1986). In order to demonstrate that these two sequences were not necessary or sufficient for long-term plasmid persistence, each sequence was deleted by removing the sequence between the HindIII and MluI sites (nt. 6959–7351, construct 8—pNeoΔNCOR, FIG. 2A). This deletion had no deleterious effect on long term replication of the plasmid (lane 8, FIG. 2B), demonstrating that these putative elements were not required. Finally, as a negative control, an XhoI linker insertion mutant overlapping with HpaI site was generated (construct 6, FIG. 2A). This mutation generated an origin defective for replication in the transient replication assay, and it is also defective for long term replication (lane 6, FIG. 2B). We concluded from these results that cis-elements required for stable replication of BPV-1 are located within the URR and are unrelated to the previously proposed elements PMS-1 and NCOR-1. We have named this cis-element in the BPV-1 URR Minichromosome Maintenance Element (MME).

MINICHROMOSOMAL MAINTENANCE ELEMENTS OF THE INVENTION

A minichromosome maintenance element is localized and defined as follows.

The Minichromosome Maintenance Element is Composed of Redundant Sequences.

Figure 3A:
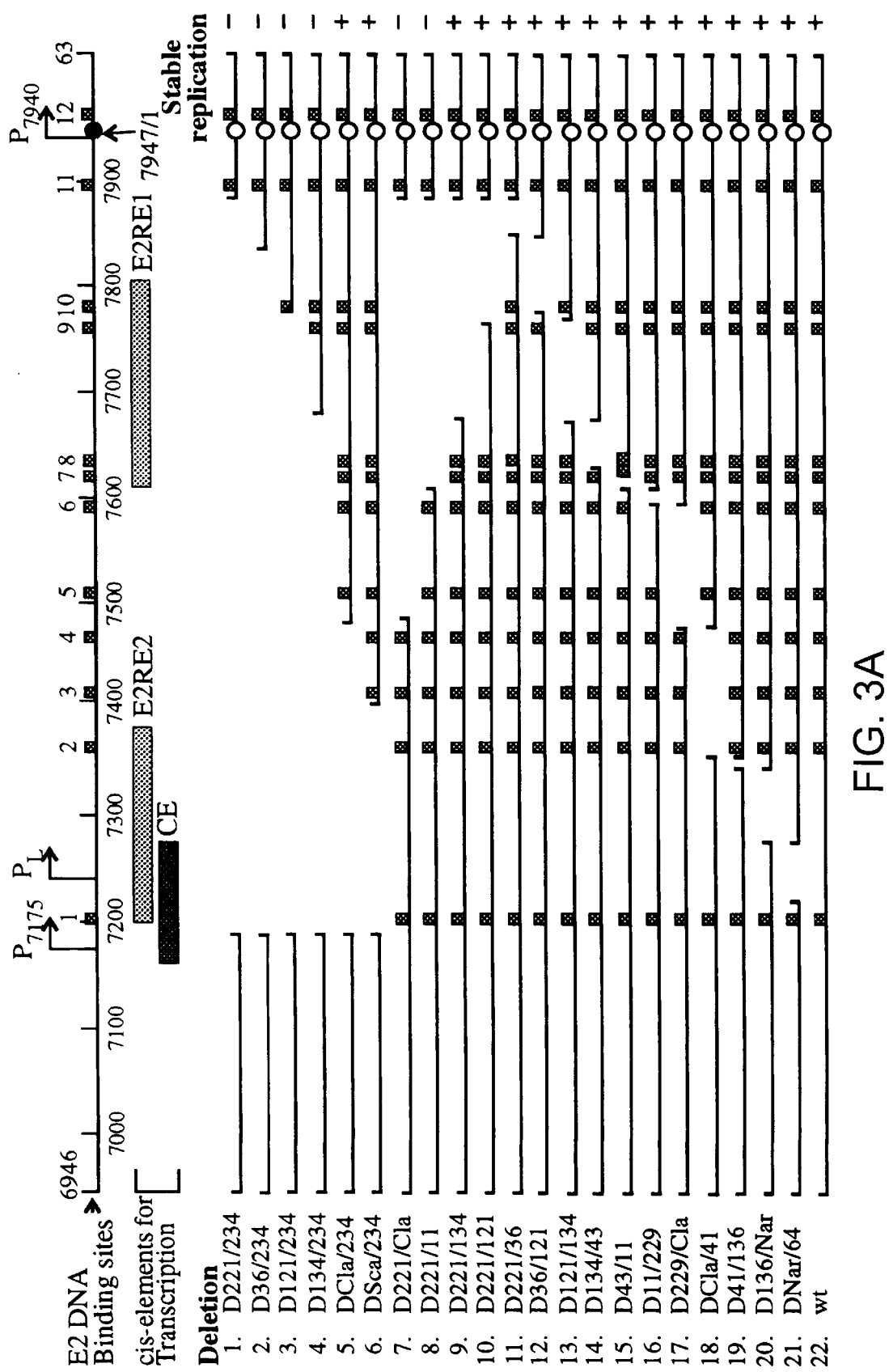
FIG. 3A shows stable extrachromosomal replication of the plasmids with deletions in the URR in CHO4.15 cells. Representation of BPV-I fragments with respective deletions. $P_{7175}$, $P_L$, $P_{7940}$—respective promoters in this fragment, E2REI and E2RE2—E2 responsive enhancer, CE constitutive enhancer, boxes indicate E2 protein binding sites. End points of the respective deletions are given in Materials and Methods. Circle indicates the location of the minimal origin. Ability of respective deletion mutants to function in long term replication assay is indicated by (+) or (−).
Figure 3B:
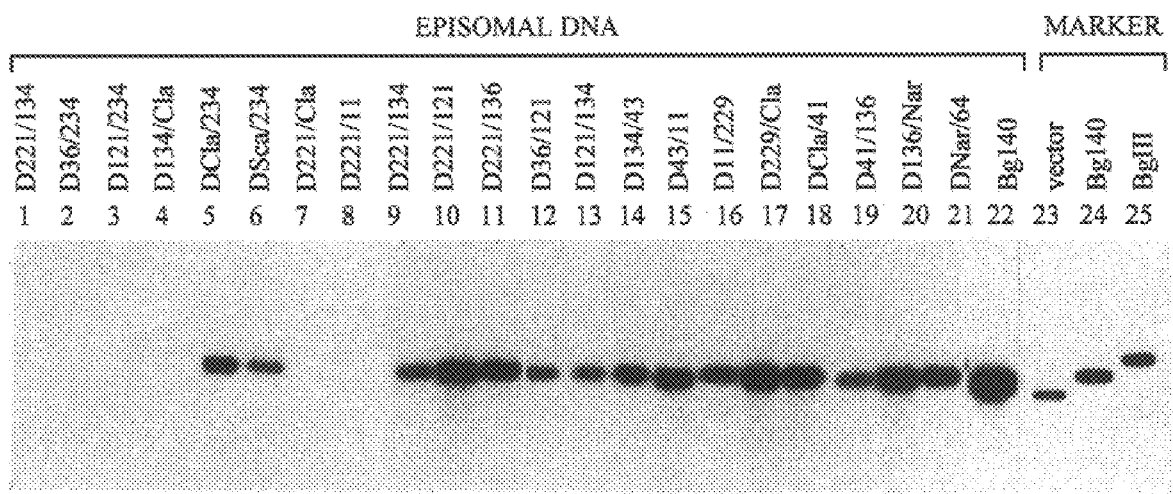
FIG. 3B. Low molecular weight DNA was extracted from the cells, transfected with respective plasmids and selected for G418, digested with the linearizing enzyme HindIII and analyzed by Southern blot (lanes 1–22). Lanes 23, 24 and 25 contain 100 pg of linearized pNeo5' vector, pNeoBgl40 and PNeoBglII marker DNA.

To define the sequences required for long term replication we generated a series of deletion mutants within the URR FIG. 3A). These deletions were made in the context of the plasmid pNeoBgl40 (BPV-1 sequence from 6946 to 63), and the deletion mutants were tested in the long term replication assay. The first series of constructs (1 –6, FIG. 3A) had a fixed 5'-end (nucleotide 7187) and progressive deletions were made at the 3'-end of the URR (nucleotides 7892, 7834, 7771, 7475, 7389, respectively). The first four of these deletions (constructs 1–4, FIG. 3A) were defective for stable replication (FIG. 3B), but the plasmids with less extensive deletions (plasmids 5 and 6, FIG. 3A) were maintained at the wild type level (lane 5 and 6, FIG. 3B). Another set of deletions (constructs 7–11, FIG. 3A) had a fixed 3'-end (nucleotide 7890) and progressive deletions from the 5'- end (7476, 7611, 7673, 7771, 7834, respectively). Two mutants of this series were unable to replicate stably (deletions 7 and 8, FIGS. 3A and 3B), but plasmids with less extensive deletions replicated efficiently (lanes 9–11, FIGS. 3A and 3B). The results from the unidirectional deletions showed that a sequence in the vicinity of nucleotide 7600 was required for long term replication (compare constructs 4 and 5, and 8 and 9). To map this sequence more precisely we generated a third set of deletions. These deletions were constructed as scanning deletions (constructs, lanes 11–21, FIGS. 3A, 3B). Surprisingly, none of the introduced mutations resulted in loss of MME activity demonstrating that no single unique sequence within the URR was required, but that maybe some redundant sequence element was responsible.

The MME is Composed of Binding Sites for the E2 Transcription Activator.

To address directly if the sequences in the vicinity of nucleotides 7600 were responsible for the MME activity we generated a fragment between nucleotides 7590 and 7673, and inserted this fragment into the deletion mutant D221/234 (construct 1 in FIG. 3A) to determine if replication in the long term replication assay could be restored (this fragment corresponds to the sequence between the deletion end-points D 134 and D11). This fragment inserted in three and six copies restored MME activity in the long term replication assay (FIG. 5, compare lanes 1 with 2,3). A known constituent of this fragment are three high affinity E2 binding sites. A possibility that occurred to us was that the MME activity was contributed by E2 binding sites. This would be consistent with the apparent redundancy, since the URR contains 10 binding sites for E2. To determine if E2 binding sites were involved in MME activity we oligomerized a high affinity E2 binding site 9 of the BPV-1 URR (5'-ACCGTTGCCGGT-3') (SEQ ID NO: 6) with six nucleotide spacing (Li et al., 1989) and inserted these oligomers (10 copies) into D221/234 deletion mutant. This insertion restored the MME activity (lane 4, FIG. 5). To rule out involvement of other BPV sequences we added 10 oligomerized E2 binding sites to the minimal origin of replication. Those constructs replicated with similar efficiency as plasmids with wild type BPV-1 sequences in the stable assay (lane 5, FIG. 5). However, plasmids with less than six additional oligomerized E2 binding sites failed to replicate in the long term replication assay (data not shown). These results strongly suggest that binding sites for the E2 protein can be responsible for providing MME activity to the BPV-1 origin.

The MME Enhances the Frequency of Formation of G418-resistant Colonies Without Replication.

Figure 6A:
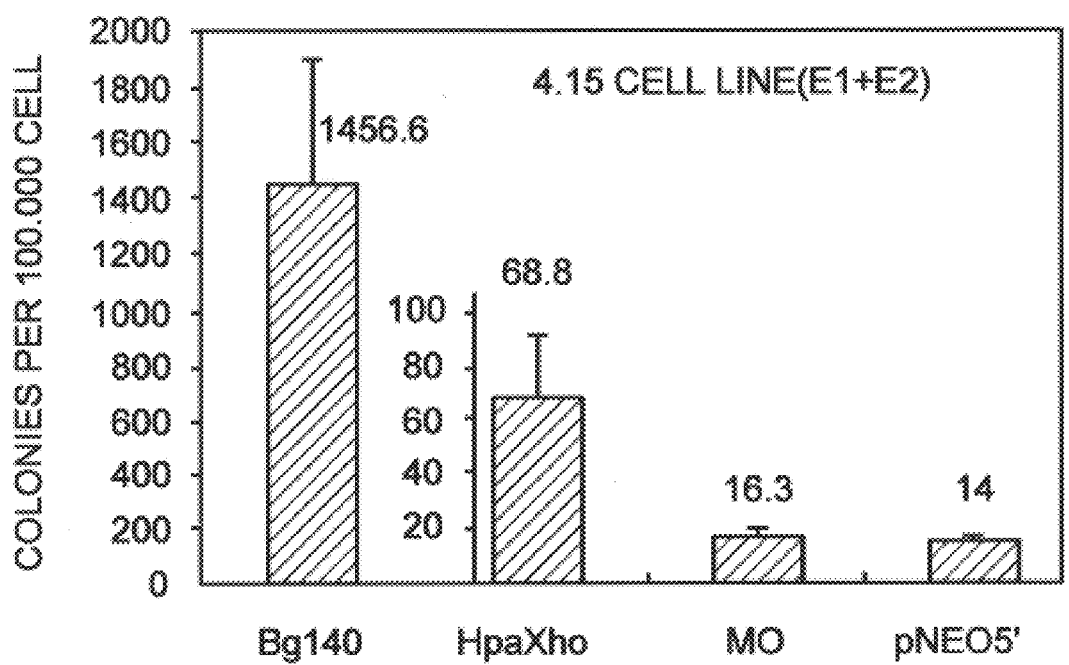
FIG. 6 (Parts A–C) shows the transformation efficiency (colonies per 100.000 cells) for G418 resistance of the plasmids pNeoBgl40 (Bgl40), pNeoXhoI→HpaI (HpaXho), pNeoMO (MO) and vector pNeo5'. 500 ng of the respective plasmid DNA was electroporated into the cells and 84 hours later cells were trypsinized, counted and plated. Complete medium containing 450 μg/ml of G418 was used for selection. Colonies were counted at the 10th day of selection. Presented values are average of three independent measurements. A. CHO4.15 cells, B. CHO212 cells and C. CHO49 cells.
Figure 6B:
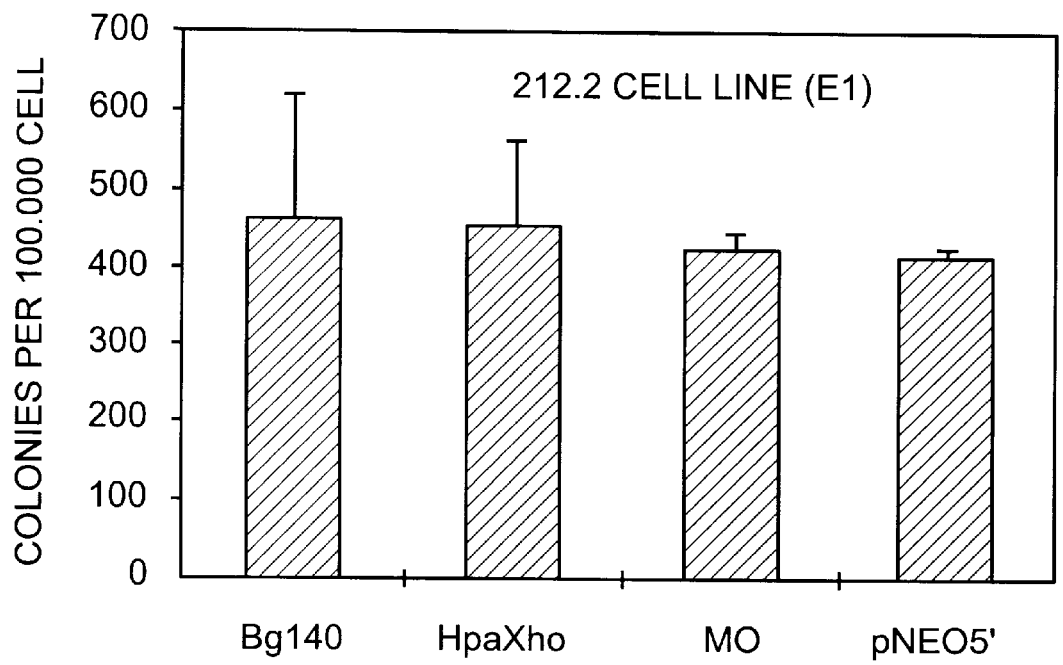
Figure 6C:
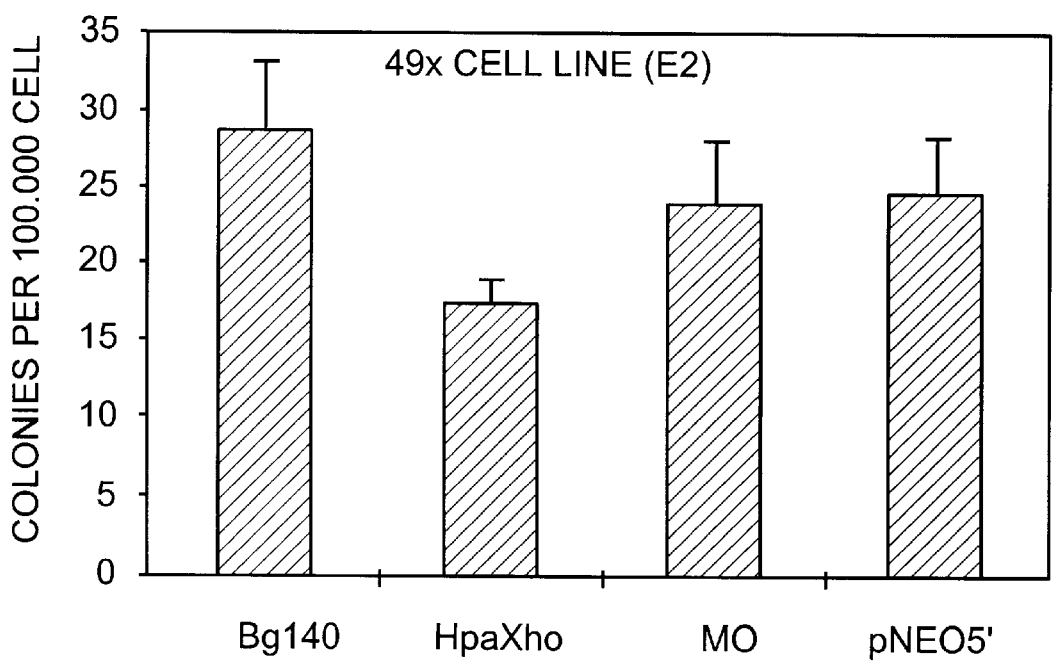

It has previously been observed that for EBV, multimerized EBNA-1 binding sites (Family of Repeats—FR) in an EBNA-1 dependent fashion are required for stable replication of oriP containing plasmids (Krysan et al., 1989; Kirchmaier and Sugden, 1995; Middleton and Sugden, 1994). This activity can be measured by increased transformation frequency of the plasmids carrying FR, and is thought to be caused by enhanced nuclear retention of plasmids containing FR. To determine if a similar activity could be determined for MME we measured the transformation frequency of four different plasmids. First, pNeo5' carries the selectable neomycin resistance marker, but lacks BPV sequences and consequently is defective for replication in both the short term and long term replication assays. Second, the minimal origin plasmid, in addition carries the BPV minimal origin and is replication competent in the short term replication assay but not in the long term assay. The third plasmid pNeoHpaI→XhoI carries the whole Bgl40 fragment, and is thus nominally capable of maintenance, but because of the linker insertion in the E1 binding site the plasmid is defective for replication. The fourth plasmid pNeoBgl40 is replication competent in both the short and long term replication assays. We used CHO4.15 cells to measure transformation frequency of these different plasmids (FIG. 6). The vector with the selectable marker only and the plasmid containing the minimal origin transformed CHO4.15 cells with similar frequency, 14 and 16 colonies per $10^5$ cells, respectively. In the parallel experiment, pNeoHpaI→XhoI which is replication defective with a mutant E1 binding site, but carrying the sequences required for MME activity, transformed CHO4.15 cells 4 to 5 times more efficiently than vector alone or a plasmid with minimal origin of replication (68.6 colonies per $10^5$ cells) (FIG. 6A). The plasmids with the complete origin transformed cells with approximately 100 times higher efficiency than the vector containing only the minimal origin of replication (approximately 1600 colonies per $10^5$ cells). These results indicated that MME activity could be measured in a stable transformation assay even in the absence of replication. When the same experiments were also performed in CHO212 (E1 cell line) and CHO49 (E2 cell line), all plasmids transformed with approximately the same efficiency in these two cell lines (FIGS. 6B and 6C). We conclude that enhanced transformation activity requires both E1 and E2 proteins.

We measured the possible effect of an MME consisting of oligomerized E2 binding sites on plasmid retention in the short term assay, as it has been done with the EBV oriP containing plasmids. However, attempts to reproduce a direct effect on nuclear retention in transient assay failed to show a significant effect (data not shown).

BPV Origin Plasmids Replicate Approximately at 15 Copies Per Haploid Genome.

Figure 4A:
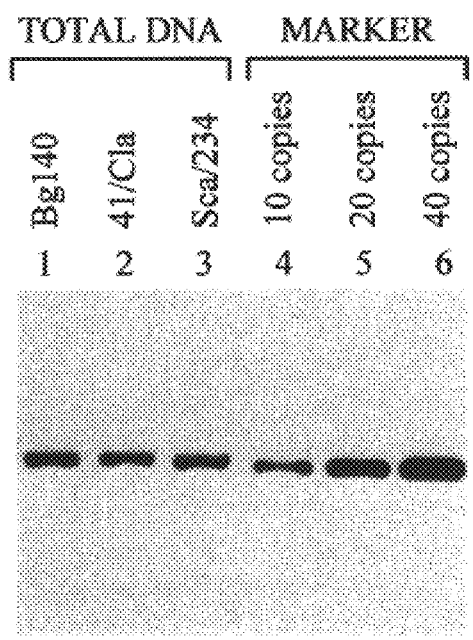
FIG. 4A represents an analysis of state and copy-number of BPV-1 origin containing plasmids in CHO4.15 cells. Copy-number measurement of BPV plasmids stably replicating in CHO4.15 cells. Total DNA was extracted from the stable cell lines and subjected for linearization with HindIII. Lanes 1–3 represent analysis of 2 µg of total DNA from three independent cell-lines, a series of plasmid dilutions for copy-number reconstruction is included in lanes 4–6.
Figure 4B:
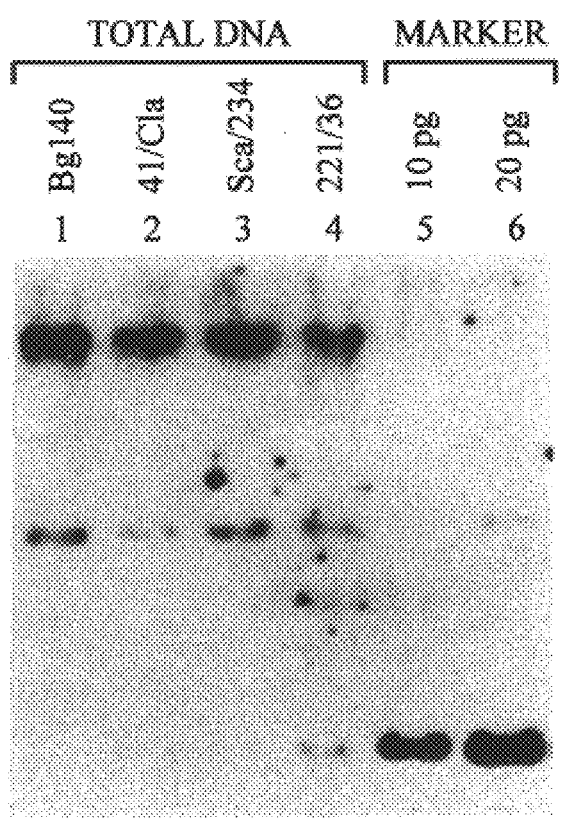
FIG. 4B shows plasmid DNA, wherein a total of DNA 2 µg, cut with plasmid noncutter ApaI, from four independent cell-lines is analyzed (lanes 1–4). Respective marker of uncut plasmid DNA is shown in lanes 5 and 6.

One of the factors that is expected to influence the stable persistence of a plasmid is the copynumber. We therefore performed experiments to estimate the average number of episomal copies per haploid genome in different established cell lines. After digestion with the single-cut restriction endonuclease (HindIII) total DNA from three independent cell lines—pNeoBgl40, pNeo41/Cla and pNeoSca/234 was loaded in equal amounts onto the gel and was analyzed by Southern blotting using radioactively labeled BPV-1 origin and neo probe. All three cell lines contained approximately the same number of episomal plasmids—15 copies per haploid genome (FIG. 4A). Even though no specific effort was made to determine the number of integrated copies, digestion with a non-cutter enzymes did not change the appearance of the three forms and oligomers of the plasmid (FIG. 4B). Consistent with previous reports, the majority of the plasmids were present in the oligomeric form. We conclude from these results that the plasmids are mostly episomal in the CHO4.15 cell line under the conditions used.

Mode of replication

One explanation for the apparent high stability of BPV-1 plasmids in the cells could be that the plasmids are subject to the cellular once per cell cycle replication control. To determine if this was the case we performed density labeling experiments using the cell line CHO4.15 containing the replicating plasmid pNeoBgl40. The experiments were performed by continuous labeling of the cells with BrdU for 3.5, 9.5, 15 or 24 hours. Low molecular weight DNA and total chromosomal DNA were extracted after each time point and analyzed by CsCl gradient centrifugation, followed by slot blotting, and hybridization with plasmid probe or genomic DNA probe to identify the peaks in the gradient. The density gradient profiles are shown in FIG. 8. The data is summarized in the table as fractions of Bgl40 DNA and CHO chromosomal DNA that had incorporated no BrdU (light-light—LL), BrdU incorporated into one strand (heavy-light—HL), or into both strands (heavy-heavy—HH) in the CHO4.15 cells stably transformed by this plasmid (FIG. 8). After labeling with BrdU for 3.5 hours (panels a) and e)) the episomal BPV-1 origin containing plasmids were divided between three forms of DNA: 5% heavy-heavy, 19% heavy-light and 76% light-light, while chromosomal DNA is distributed between two forms 27% heavy-light and 73% light-light. After labeling for 9.5 hours, the plasmid has accumulated considerable amount (21%) of heavy-heavy DNA, while chromosomal DNA shows no detectable signal in the heavy-heavy area. After labeling for 15 hours, distribution of the episomal DNA is 34% heavy-heavy, 38% heavy-light, 28% light-light. At the same time chromosomal DNA showed still very little, if any, heavy-heavy DNA. After labeling for 24 hours, episomal DNA was preferentially in the heavy-heavy fraction of the DNA (66%), 24% heavy-light and 10% light-light, while chromosomal DNA showed considerable amount of heavy-heavy DNA (24%), but with most of the DNA still in the once replicated DNA fraction. These results are consistent with a doubling time of approximately 16 hours for the pNeoBgl40 containing cell lines. The considerable percentage of the unreplicated chromosomal DNA after 24 hours is likely to be due to growth arrest of a fraction of the cells by the conditions used for BrdU labeling. It appears clear from these results that the stably maintained pNeoBgl40 plasmid does not replicate once per cell cycle and stable persistence of the BPV-1 plasmids is not a function of once per cell cycle replication control.

Mechanism of Action

Three mechanisms of action can be envisioned for the MME. First, the MME could affect the efficiency of initiation of replication. Although no difference in replication initiation can be detected during the time-course of the transient replication assay (Ustav et al., 1991), it is conceivable that a gradual accumulation of methylated residues at the origin of replication or some other form of modification (including nucleosome occlusion) could prevent initiation of replication and results in gradual loss of replication activity. It is possible that MME can affect these processes and prevent inactivation of the origin. Alternatively, the minimal origin containing plasmids are competent for over replication during the S-phase of the cell cycle, which could be toxic to cells. MME could prevent this process, in analogy to the function of iterons for certain bacterial plasmids (for review Nordström, 1991). Third, MME could influence the partitioning process thereby affecting the loss rate of plasmids during cell division.

It is interesting to note that the ability of the minimal origin containing plasmids to replicate appears to have no detectable effect on transformation frequency. One might have expected that an increase in the quantity of plasmid DNA in the cells as a result of replication would lead to a higher frequency of integration. However, this appears not to be the case, possibly because these minichromosomes are poor substrates for the required recombination events or are lost with very high frequency at cell division. The very large increase in transformation frequency of the plasmids with both MO and MME compared to integrating marker presumably reflects the fact that the two functions together can bypass the requirement for integration possibly by providing an efficient segregation/partitioning function in addition to replication.

Materials and Methods

The following methods are routinely used in the invention. These methods are stated in terms of the detailed experiments performed herein. However, each method may be generalized by one of skill in the art for use in carrying out the invention in its broadest sense, as described below and claimed.

Plasmid construction.

(i) Expression vectors.

The E1 and E2 protein expression vectors pHSE2 (Szymanski and Stenlund, 1991), pCGE2 and pCGEag (Ustav and Stenlund, 1991) have been described earlier. The E1 expression vector pE1—1×5 contains the BPV-1 E1 ORF with XhoI linkers (within nucleotides 619 to 2757) and carries a point mutation at the splice donor site at nucleotide 1235. This fragment was cloned into the XhoI site downstream of the SRα-promoter in the plasmid pBJ5GS (kind gift from Dr. L. Berg).

(ii) Origin plasmids.

All origin fragments of the BPV-1 genome were cloned in sense orientation into the BamHI site of the pNeo5'(Lusky and Botchan, 1984). pNeoBglII contains a BglII fragment from BPV-1 (nt. 6946 to 1515) cloned in the sense orientation relative to the transcription of the neo gene. pNeoXhoI→HpaI contains the same BglII fragment with an XhoI linker insertion into the HpaI site (Ustav et al., 1991). pNeo 576, pNeo775 and pNeoSma⁻ plasmids contain the same BglII fragment with the mutations 576, 775 and Sma–which affect E6/7 ORF, E6 ORF and the 5'-part of the E1 ORF, respectively (Lusky and Botchan,1985; Schiller et al., 1984; Berg et al., 1986). pNeoΔNCOR has a deletion between HindIII (nt. 6958) and MluI (nt.7351). pNeoBgl40 contained a BPV-1 fragment from nucleotide 6946 to 63, which was amplified by PCR using respective primers and cloned in sense orientation into the BamHI site. pNeoMO contained minimal origin sequence (nucleotides 7914 to 27) cloned into the BamHI site. Linker deletion mutants of the BPV-1 genome (Szymanski and Stenlund, 1991) were used as templates for PCR. Primers—5'-AAAAGCTTTCTTTGGACTTAGA-3' (SEQ ID NO.: 7) (BPV-1 nucleotides 6959–6979) and 5'-ATAGCCAGCTAACTATAGATCT-3' (SEQ ID NO.: 7) (BPV-1 nucleotides 45 to 63 flanked by BglII site) were used to amplify origin fragments. PCR products were cloned into the HindIII and BamHI site of the pNeoBgl40. Deletion mutants lacked following sequence: D221/234-7187/7892; D36/234 7187/7834; D121/234-7187/7771; D134/234-7187/7673; DCla/234-7187/7475; DSca/234 7187/7389; D221/Cla-7476/7892; D221/11-7611/7892; D221/134-7673/7892; D221/121 7771/7892; D221/36-7834/7892; D36/121-7771/7834; D121/134-7673/7771; D134/43-76227673; D43/11-7611/7622; D11/229-7597/7611; D229/Cla-7476/7597; DCla/41-7355/7476; D41/136-7344/7356; D136/Nar-7273/7344; DNar/64-7214/7273 and junctions contained 8-mer BamHI Tinkers; D221/234+134/1 1×3 contains an insertion of the fragment 7590–7673 in three copies and D221/234+134/1 1×6 in six copies. D221/234+10BS9 has an insertion of the E2 protein binding site 9 in ten copies. DHindIII/221+10BS9 is a deletion between nucleotides 6959/7892 which carries 10 copies of oligomerized E2 binding site 9. All deletion and insertion mutants were verified by sequencing.

Construction of cell lines.

CHO-K1 (Chinese Hamster Ovary—ATCC CCL 61) was used as the parental cell line to express BPV-1 replication proteins.

(i) E2 cell line CHO49. The E2 expression vector pHSE2 was linearized with XhoI and the plasmid pBJ5GS carrying glutamine synthetase minigene expression unit (Bebbington and Hentschel 1987). pBJ5GS (kind gift of Dr. L.Berg) was linearized with SalI endonuclease. The plasmids were mixed at a 1:1 ratio and ligated into the concatemers at high DNA concentration (300 μ/ml) overnight at 16° C. using T4 DNA ligase.

Ten micrograms of the ligated DNA was mixed with 50 μg carrier DNA and was electroporated into the 7×10$^6$ CHO-K1 cells using Ham's F12 medium supplemented with 10% fetal bovine serum at 220V, using a BioRad electroporation apparatus at the capacitance setting 960 μF. Selection for glutamine synthetase was done at 25 μM concentration of the L-methionine sulfoximine (Sigma) in glutamine free Glasgow Minimal Medium supplemented with dialyzed fetal bovine serum, non-essential amino acids, glutamic acid, aspartic acid, sodium pyruvate, nucleosides, penicillin and streptomycin, essentially as has been described by Bebbington and Hentschel (Bebbington and Hentschel, 1987). Colonies were picked ten days after the selection, expanded and used for the second round of selection at 250 μM of L-methionine sulfoximine. This step was included to amplify the sequences coupled to the selection marker. Cell lines were expanded and tested for expression of E2 protein by immunoprecipitation with polyclonal rabbit antibodies against E2 protein (Ustav and Stenlund, 1991) after labeling with $^{35}$S L-methionine using Translabel (ICN) and by functional transient replication assay as described below.

(ii) E1 cell line CHO212.

E1 protein expression vector pCGEag (Ustav and Stenlund 1991) was linearized by the XhoI and pBJ5 GS was linearized, mixed at a 1:1 ratio and ligated into the concatemers and the cell line expressing E1 protein was generated essentially same way like E2 expressing cell line.

(iii) E1 and E2 expressing cell line CHO4.15.

E1 protein expression vector pE1-1×5 containing glutamine synthetase minigene and E1 coding sequence was linearized with SalI and pHSE2 was linearized with the XhoI restriction endonuclease. Linear plasmids were ligated into the concatemers at a ratio 1:1, CHO-K1 cell were transfected by electroporation and selected as described above.

Transient replication assays were done as described earlier (Ustav and Stenlund, 1991) using the respective cell lines. For testing the cell lines in functional assay for expression of the BPV-1 replication proteins we used 50 ng of pUC/Alu (Ustav et al., 1991) as origin containing plasmid and 250 ng of the E1 expression vector pE1-1×5 or pCGE2 to complement E2 cell line CHO49 or E1 cell line CHO212, respectively. All pNeo5' based origin plasmids were tested for their ability to replicate in the CHO4.15 cell line by transfecting 100 ng of the plasmid DNA together with 50 ptg of denatured carrier salmon sperm DNA into the CHO4.15 cells at 240V by electroporation. Extrachromosomal DNA was extracted from the cells at 48 and 72 hours post-transfection by alkaline lysis as described earlier (Ustav and Stenlund, 1991). DNA was purified, digested with DpnI and linearizing enzyme and were analyzed by Southern analysis. Specific probes for hybridization were made by random priming.

Stable replication

CHO4.15 cells were electroporated with 100 ng of origin containing plasmid DNA in the presence of 50 μg of carrier DNA. Ninety six hours after transfection CHO4.15 cells were trypsinized and subjected for the antibiotic G418 selection at the concentration 450 μml. Colonies were pooled or single colonies were picked after two weeks, expanded and episomal or total DNA were analyzed by Southern blotting.

Copy-number measurement

Total DNA from established cell lines, containing replicating BPV-1 origin plasmids, was extracted and digested either with a plasmid single-cutter (HindIII) or a plasmid non-cutter (ApaI), followed by electrophoresis in 0.7% agarose/TAE gels. The copynumber was measured by Southern blotting, using probe containing sequences from the BPV ori and neo gene. Results were quantitated by comparing band intensity to a two-fold dilution series of plasmid DNA using phosphoimager.

BrdU labeling and analysis of the replication mode

Cells were labeled with 35 μg/ml BrdU in MEM medium, containing 2'-deoxycytidine (20 μg/ml) using procedures described earlier (Yates and Guan, 1991). Episomal and chromosomal DNA was extracted at time points indicated in Results section. CsCl solution was added to DNA preparation to 1.74 g/ml and centrifuged for 48 hours at 37000 rpm. 24 fractions were collected from each gradient, subjected to denaturation and neutralization, and slot-blotted onto nylon filters. Filters were hybridized with labeled BPV-1 or CHO genomic DNA probes. Radioactivity was counted with Phosphoimager, Fuji.

Nuclear retention measurement by stable transformation assay 48 hours following transfection the cells were trypsinized, counted and plated at 3 different dilutions. G4 18 selection was applied, and the selective medium was changed every 3 days. Colonies were counted after 10 days.

TREATMENT OF DISEASES ACCORDING TO THE INVENTION

The invention is useful in vivo and ex vivo human gene therapy where correction of inherited or acquired genetic defects is desired, and is therefore useful to treat any disease where gene delivery provides benefit, whether the gene is delivered to a terminally differentiated host cell, such as a hepatocyte, or to an undifferentiated cell such as a stem cell. The invention is useful in treatment of chronic or acute diseases, e.g., T-cell diseases, inflammation, fibroses of the liver, and arthritis. The invention also is useful in vaccination protocols where resistance or immunity to infectious pathogens, such as HIV, Hepatitis C Virus, Hepatitis B virus, is desired, or the elimination or induced quiescence of aberrant cells, such as cancer cells, is considered beneficial.

Recombinant vectors of the invention are useful in that they permit persistent expression of a therapeutic gene in both dividing and non-dividing cells; for example, in differentiated cells, such as those in gut, brain, and muscle.

Recombinant vectors of the invention are also useful for high level transient expression in cells where desired, such as for cancer therapy or in vivo vaccination.

Both in vivo and ex vivo gene therapy strategies are possible with this vector system, including stable, multicopy gene maintenance and expression, in haemopoietic and other stem cells, and in the committed and differentiated progeny of these cell types.

Nucleic acid vectors suitable for use in the present invention include circular and linear lengths of DNA.

For human gene therapy, uses of the recombinant vectors of the invention are not limited in terms of delivery of the vector to a cell. That is, vectors of the invention may be delivered to a cell via non-viral or viral delivery systems. Delivery systems of non-viral origin include those which employ molecular conjugates, cationic liposomes, or synthetic peptides, where vector size constraints do not limit the nature and number of plasmid vector components. Delivery systems of viral origin include viral particle-producing packaging cell lines as transfection recipients for the above E1/E2/MO/MME-containing plasmids into which viral packaging signals have been engineered, such as those of adenovirus, herpes viruses and papovaviruses.

Recombinant vectors of the invention also are useful in transgenesis, including production of transgenic animals via pronuclear injection, or embryonic stem cell transfection and embryo chimera generation.

Heterologous Genes Useful According to the Invention

Heterologous genes useful in vectors of the invention may also encode antigenic determinants of viruses, so as to be useful as vaccines, such antigenic determinants as are present in coat proteins of flu viruses, malaria, TB, and HIV. For modulation of physiologic activity in brain cells, genes including the following may be of interest: CCKA, CCKB, CREB, TH, NT3, NT4, BDNF, GDNF, and NGF.

Regulatory Sequences Useful According to the Invention

As described below, regulatory sequences which may be carried in vectors of the invention will of course include heterologous promoter and enhancer sequences which control expression of the heterologous gene of interest, and which may be confer a tight level of regulation upon the heterologous gene, including inhibition or activation of gene expression, promoter/enhancer strength, tissue specificity, or relatively little regulation beyond the initiation of transcription.

Vectors useful according to the invention may advantageously include a gene encoding a therapeutic agent, a promoter which directs expression of the gene, and optionally a cellular-derived gene regulatory element which confers tissue specific gene expression. The promoter/gene combination may be subject to any one of numerous forms of gene regulation known in the art, for example, production of the gene product may be subject to continuous inhibition by associated factors and thus may require the presence of an activator; alternatively, the gene product may be continuously expressed, and only inhibited under certain conditions. Gene expression may be regulated at either the transcriptional or translational level. Where such regulation is transcriptional, it may be at the level of the promoter or at the level of RNA elongation or processing. Therefore, vectors useful according to the invention may include a heterologous promoter/gene combination that is turned-on and turned-off in trans by the presence or absence of a regulatory factor.

Heterologous Regulatory Sequences for E1 and E2 Gene Expression

In addition to heterologous sequences to regulate a heterologous gene of interest which is carried on the episomal vector, heterologous regulatory sequences are also used in the invention to control expression of the papilloma E1 and E2 genes. Proper control of expression of E1 and E2 is critical for determining plasmid copy number, stability and segregation, and therefore the invention encompasses maintenance of an MO+MME-containing plasmid in eukaryotic cells. The presence of heterologous regulatory elements has been found to influence persistent expression, expression in different cell types, and expression in vivo.

Figure 10:
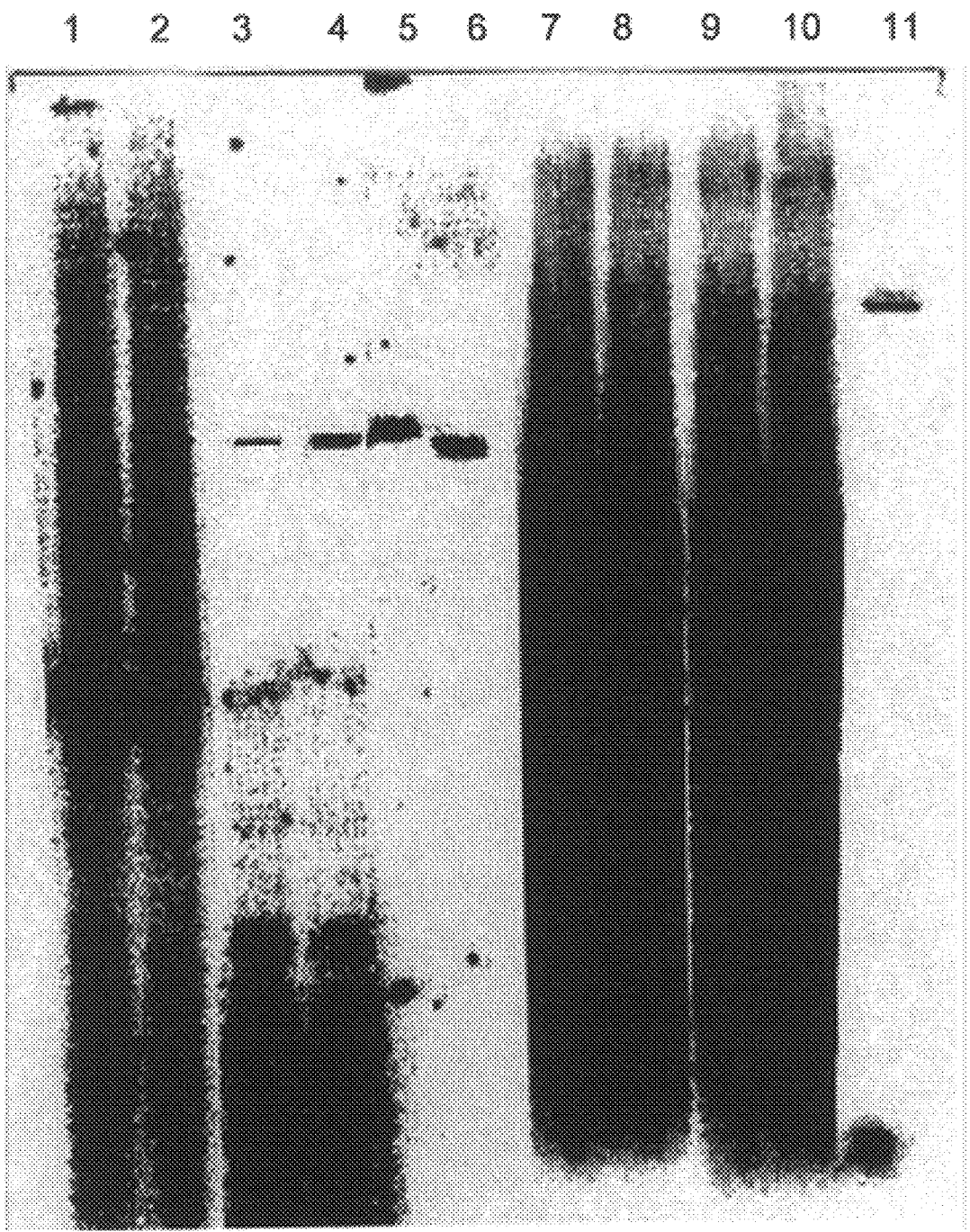
FIG. 10 shows transient replication of pSR alpha and pTk vectors (FIG. 7) in CHO (lane 1–4) and C333A (lanes 7–10) cell lines. 2 micrograms of respective plasmid was transfected into the cells by electroporation, time points were taken 36 and 48 hours post-transfection and low-molecular weight DNA was extracted, digested with DpnI and HindIII and analyzed by Southern blotting. Lanes 1–2 and 7–8 represent transient replication of SR alpha vector in CHO and C33A cells respectively. Over-replication is clearly visible in case of both cell lines. Lanes 3–4 and 9–10 represent transient replication of TK vectors in CHO and C33A cells respectively. Some over-replication is detectable in C33A cells, whereas replication of TK vector in CHO cells is weak, but without smear. The latter is characteristic for onion-skin type over-replication. Lanes 5–6 and 11 represent respective molecular-weight markers.

Choice of a heterologous promoter to drive E1 gene expression has been found to confer certain advantages to a vector of the invention, depending upon the intended use of the construct. For example, it has been found that a strong promoter such as SRalpha (a hybrid of SV40 early region and HTLV-1 LTR) to drive expression of the E1 gene can be used advantageously according to the invention to drive plasmid copy number very high, that is, to levels which render the host cell unhealthy and prevent normal cell division. This generates unstable, onion skin-like products and leads to cell inviability (FIG. 10). However, a strong promoter is advantageously used where high level transient expression of a vector heterologous gene is desired, for example, in treatment of a cancerous condition where it is desirable to produce a high level of heterologous gene product (for example, a toxin) and it is also desirable to kill the host cell (for example, tumor cells). This type of vector of the invention takes advantage of the ability of the MO/MME vector system to replicate at very high levels independently of the cell cycle.

Figure 11:
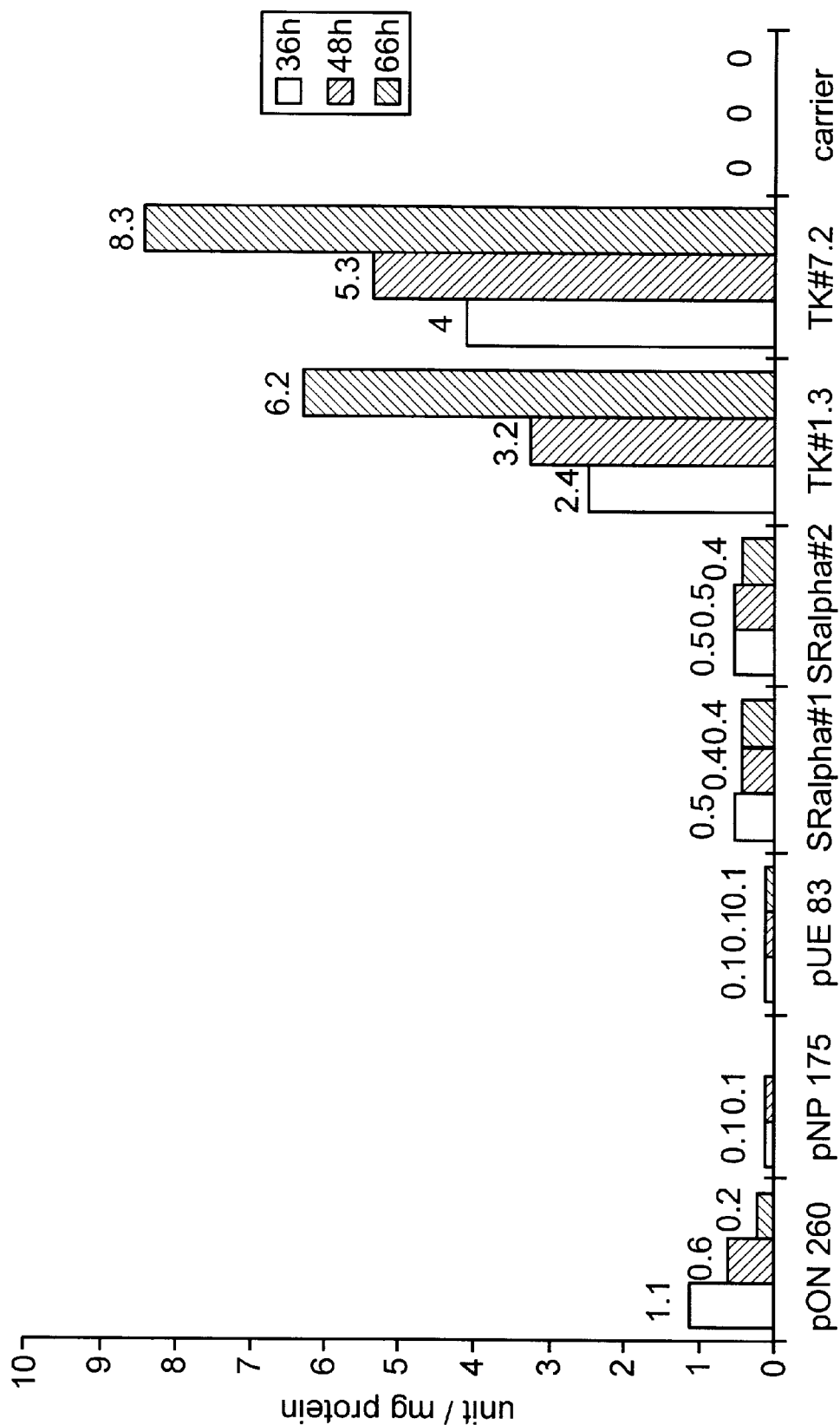
FIG. 11 shows beta-galactosidase activity in CHO cells transfected with equimolar amounts of vector plasmids. In plasmids pON260 beta-galactosidase gene is expressed from immediate early CMV promoter. In other vector constructs beta-galactosidase is expressed from RSV LTR.
Figure 12A:
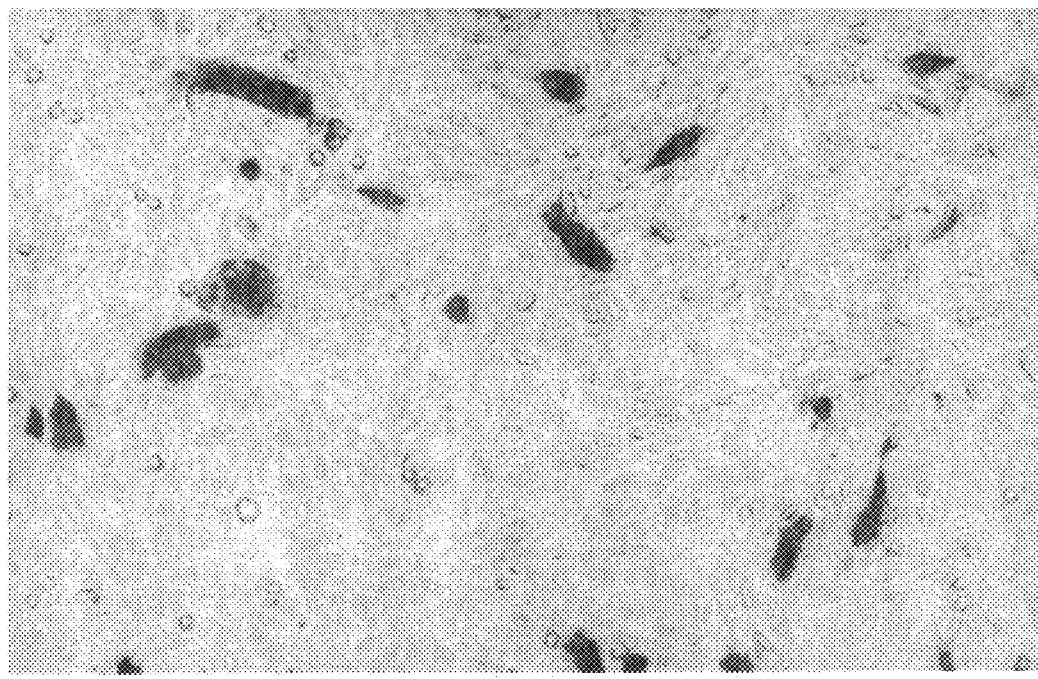
FIGS. 12A and B shows beta-galactosidase assay for the cells transfected with the pSR alpha and pTK constructs after 56 hours. In the case of TK constructs formation of lacZ-positive blue colonies could be detected, however in the case of SRalpha constructs only single, strongly stained, blue cells could be detected in the culture indicating that plasmids are not inherited to each of the daughter cells during cell division.
Figure 12B:
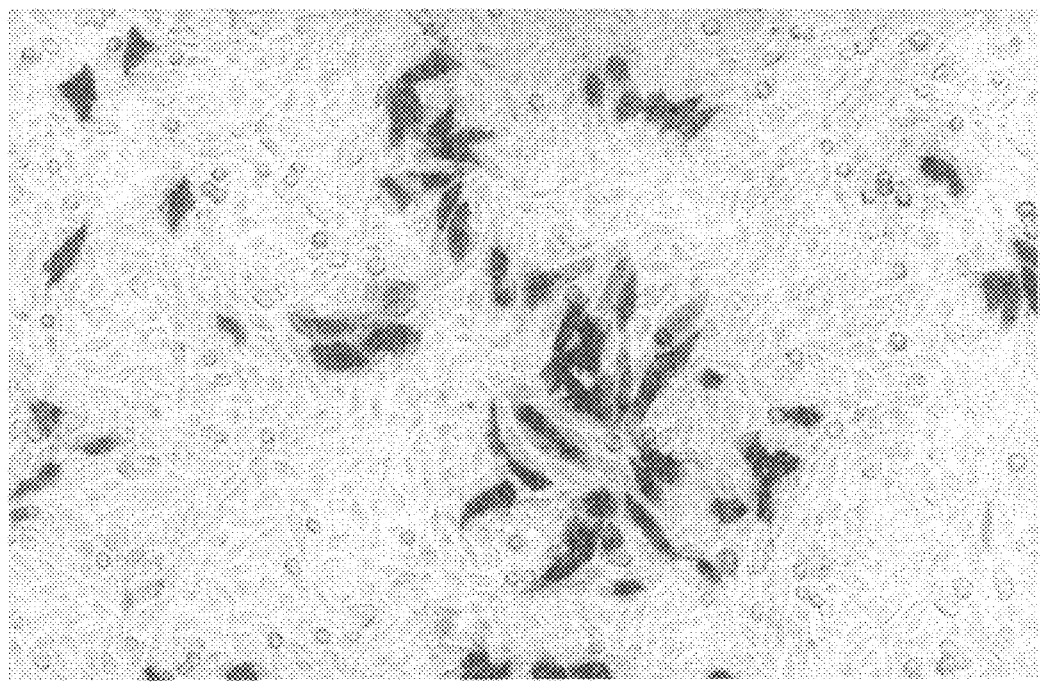

In contrast, it has also been found that use of a weaker promoter, such as the thymidine kinase promoter, to drive E1 gene expression can be used advantageously in the invention to permit sufficient E1 protein expression to regulate stable (MO+MME)-containing plasmid replication at high efficiency.(FIG. 10). Similarly, use of the weaker promoter such as thymidine kinase promoter permits E1 protein synthesis to a level compatible with efficient expression of a reporter gene product from the constructs in transient assay (FIG. 11). The results shown in FIG. 12 demonstrate stable expression of beta-gal in the cells upon selection. SRalpha-E1 constructs express reporter, however cells are not dividing while Tk-E1 constructs work for expression in transient as well as in stable cells; cells divide normally to give colonies which stain blue for beta-gal protein.

Figure 13A:
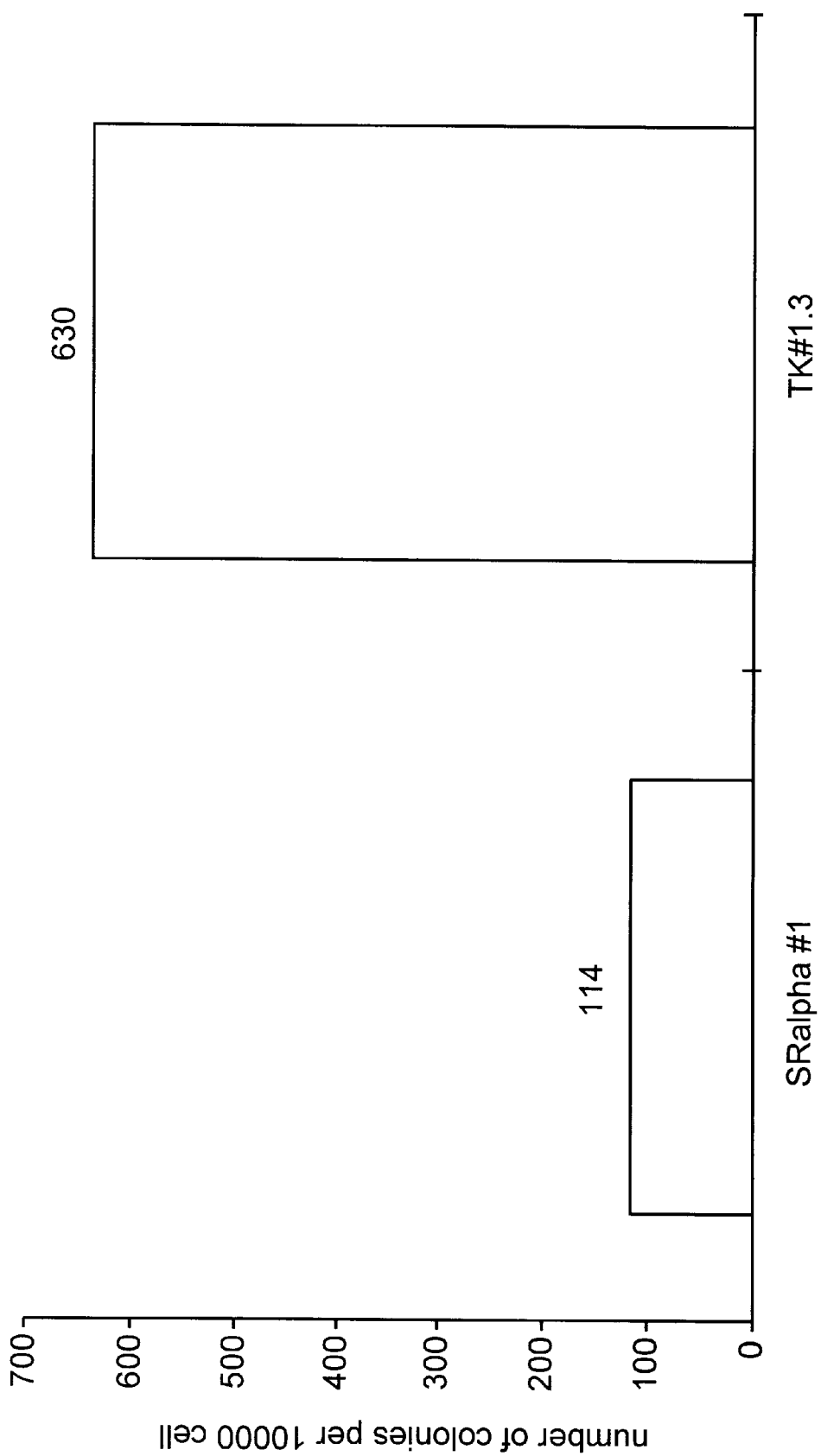
FIG. 13A shows a number of colonies per 10000 cells transfected with equal molar amounts of vectors selected for G418.
Figure 13B:
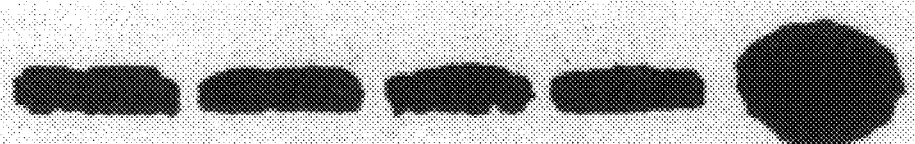
FIG. 13B is an analysis of the episomal DNA in the cells transfected and selected for G418 with the TK-E1 constructs.

Proper control of post-transcriptional processing of E1 and E2 transcripts further influences the replicative and expression properties of the plasmid system (efficiency, compatibility with host replication system, stability, toxicity), and is improved by incorporation of sequences such as those of human beta globin gene (exxonII, intronII, exonIII sequences), and SV40 sequences which incorporate splice, polyA and mRNA stability sequences. Improved expression vectors harboring such elements in the E1 and E2 expression domains are described herein. FIGS. 13A and 13B show G418 selection of different vectors (SRalpha-E1 and TkE1 constructs).

In addition to the use of regulatory sequences for regulation of E1 and E2 gene expression, the invention also encompasses the use of regulatory sequences for control of a heterologous gene encoding a protein of interest, which gene is carried on an episomal vector of the invention.

The adenovirus E1A promoter and enhancer, the human CMV-MIE promoter and enhancer, retroviral LTR elements, herpesvirus promoters, and poxvirus promoters are representative examples of heterologous regulatory elements useful in the invention.

Modification of a heterologous promoter useful according to the invention may be accomplished according to a number of strategies. For example, the use of negative regulatory elements which decrease the level of transcription is envisaged. Especially preferred, however, is the modification of the promoter sequences in order to reduce the basal levels of transcription. Promoter sequences may be modified in order to remove regulatory elements which respond to cell-specific regulatory factors. Preferably, therefore, elements responsible for activation by cell-specific factors may be mutated or deleted.

Modified Forms of a Promoter Useful in the Invention

The invention encompasses the use of modified forms of a heterologous promoter, which exhibit decreased levels of basal transcription. Such heterologous promoters may be useful in the invention, because it may be desirable to confer upon the host cell a low enough level of transcription of, for example, an anti-viral gene or a gene encoding a toxin so as to prevent deleterious effects on the host cell by virtue of the presence of the encoded gene product in the cell.

Modified forms of a given promoter may be made, as is well-known in the art, using conventional PCR and incorporating random or directed base substitutions, deletions, or insertions in the native promoter sequence.

Transactivatable viral promoters useful according to the invention include but are not limited to the following: Herpes Virus (HSV-1), immediate early promoter (Liv et al., 1990, Biotechniques 9:168; Rice et al., 1990, Jour. Virol. 64:1704; Howard et al., 1993, Exp. Cell. Res. 207:194); Visna Virus promoters (Carroth et al., 1994, Jour. Virol. 68:6137); Papillomavirus promoters (Storey et al., 1990, Jour. Ge. Virol. 71–965 and Ibaraki et al., 1993, Virus Genes 7:187; Epstein-Barr Virus promoters (TPI and Barn HIC promoters) Cohen et al., 1991, Jour. Virol. 65–5880; Sung et al., 1991 Jour. Virol. 65:2164; and Meitinger et al., 1994, Jour. Virol. 68:7497); CMV promoters (IE2, IE1, and MIE promoters) (Malone et al., 1990, Jour. Virol. 64:1498; Cockett et al., 1991, Nucl. Ac. Res. 19:319; and Pizzomo et al., 1991, Jour. Virol. 65:3839); Hepatitis B promoters (Seto et al., 1990, Nature 344:72; Raney et al., 1991, Jour. Virol. 65:5774; Lauer et al., 1994, Hepatology 19:23); Spumaretroviral promoters (Rethwillm et al., 1990, Virol. 175:568, Venkatesn et al., 1993, Jour. Virol. 67:3868); HTLV-1 promoters (Franklin et al., 1993, Jour. Biol. Chem. 268:21225; Kadison et al., 1990, Jour. Virol. 64:2141); and Adenoviral promoters (E2) (Obert et al., 1994, Mol. All. Biol. 14:1333).

Heterologous promoters useful according to the invention, including modified forms of a given promoter, are first tested for basal activity using a reporter gene, and are also tested to determine if they possess or retain the ability to be trans-activated. Where a vector of the invention includes heterologous promoter/gene combination which is present in the cell in an inhibited state and which requires transactivation for production of the encoded heterologous gene product, such promoter/gene combinations may be most useful provided they possess or retain the ability to be transactivated while exhibiting a low enough level of basal activity such that the gene product is virtually undetectable.

A vector of the invention, whether its heterologous promoter is modified or unmodified, may be tested for its ability to be trans-activated to the extent that differential killing of transformed cells occurs. Functional tests of diminished basal activity from vectors of the invention will include the use of prodrug activating systems, such as ganciclovir, in cells containing a vector in which the heterologous promoter/gene combination is in the inhibited versus the activated state.

Regulatory Elements conferring Cell-Type Specific Heterologous Gene Expression

Cellular-derived genetic elements also may be included in episomal vectors of the invention.

These genetic elements thus are responsive to, i.e., subject to control by, cellular factors. Tissue-specific promoters may confer tissue specificity.

E2 Mutants Defective for Transcriptional Activation

The invention also encompasses the use of E2 mutants which are defective in the E2 transcriptional activator function. A gene encoding such an E2 mutant is incorporated into the episomal vector system of the invention.

Full-length E2 protein has two functional domains which are well-conserved among the E2 proteins of different papollomaviruses, a 200 amino acid transactivation domain at the amino terminus and a 90–100 amino acid carboxy terminal domain that is essential for dimerization and DNA binding. A flexible spacer hinge region separates the trans-activation and DNA binding domains.

In order to provide an E2 mutant which is defective in transcriptional activation, but which are able to supply the E2 function that is necessary and sufficient for episomal persistence, point mutations have been made in the gene encoding this protein. These mutations are useful where they eliminate the transcriptional activating activity of the protein without affecting the ability of the resultant protein to stably maintain (MO+MME)-containing plasmids in transfected cells.

E2 mutants were made by selected mutation of amino acids which are believed to lie in hydrophilic domains at the protein surface, and by then changing basic or acidic amino acids to a small hydrophobic and/or polar residue, e.g., alanine, which has a short side chain consisting of a single —$CH_3$ group; serine, which also contains a single carbon atom side chain (—$CH_2OH$); valine, leucine, threonine and isoleucine, which are hydrophobic amino acids having side chains ranging from 2–4 carbon-containing groups. The mutation is introduced into the E2 gene using oligonucleotide-directed mutagenesis in M13 phage. It is within the scope of the invention to locate additional point mutations which abolish the transcription activating activity of E2 without deleteriously affecting its replication function to maintain episomal vectors according to the invention.

Manufacture of Vectors of the Invention

The invention also features vectors which include sequences conferring replication and selection in lower eukaryotic or prokaryotic host cells in order to manufacture a useful quantity of vector DNA, e.g., 100 μg–mg quantities.

Additional sequences which may be present in a vector of the invention to enable manufacture of vector DNA include other origins of replication, e.g., a bacterial or yeast origin of replication, which permits preparation of vector DNA in prokaryotic or eukaryotic cells, or baculovirus sequences which allow for vector replication in insect cells.

This aspect of the invention is applicable to most strains of bacteria, for example, gram positive and negative bacterial strains, and yeast. Gram negative bacteria useful according to the invention include but are not limited to *E. coli* and Salmonella, e.g., *S. typhimurium*. Gram positive species useful according to the invention include but are not limited to Bacillus and Lactococcus.

Prokaryotic and Eukaryotic Origins of Replication

The invention can be utilized advantageously with a plasmid origin of replication that permits replication of at least 10, preferably at least 20–100, and most preferably at least 200–500 copies of the plasmid per host cell. Those origins of replication that permit replication of moderate (i.e., 2050) to high plasmid (i.e., 200–500) copy numbers are especially useful. Of course, if desired, a plasmid having a copy number, as high as 1000–2000 copies per cell, also may be used.

Plasmids with low copy numbers (i.e., 10 copies or less) are most advantageously used according to the invention after mutation to bring about increased copy number (J. Scott, 1984, Microbial Reviews 48:1–23). Of the frequently used origins of replication, pBR322 (20 copies/cell) is useful according to the invention, as is pUC (at 200 copies/cell). Other plasmids whose origins of replication may be useful according to the invention are those which require the presence of plasmid encoded proteins for replication, for example, the pT181, FII, and FI origins of replication.

Examples of origins of replication which are useful according to the invention in *E. coli* and *S. typhimurium* include but are not limited to pMB 1 (25 or more copies per cell, Bolivar et al., 1977, Gene 2:95–113), ColE1 (15 or more copies per cell, Kahn et al., 1979, Methods Enzymol. 68:268280), p15A (about 15 copies per cell, Chang et al., 1978, J. Bacteriol. 134:1141–1156); pSC101 (about 6 copies per cell, Stoker et al., 1982, Gene 18:335–341); R6K (less than 15 copies per cell, Kahn et al., 1979, supra); R1 (temperature dependent origin of replication, Uhlin et al., 1983, Gene 22:255–265); lambda dv (Jackson et al., 1972, Proc. Nat. Aca. Sci. 69:2904–2909). An example of an origin of replication that is useful in Staphylococcus is pT181 (about 20 copies per cell, J. Scott, 1984, Microbial Reviews 48:1–23. Of the above-described origins of replication, pMB1, p15A and ColE1 are preferred because these origins do not require plasmid-encoded proteins for replication.

Genes Encoding Selectable Marker Useful in Vectors of the Invention

Genes encoding selectable markers useful in vectors of the invention include antibiotic resistance genes, for example encoding resistance to antibiotics such as ampicillin, kanamycin or tetracycline, are the most common dominant selectable markers used in molecular biology cloning and fermentation procedures for the production of recombinant proteins or plasmid DNA.

Preparation of vector DNA can also be used in conjunction with antibiotic resistance. Representative antibiotic resistance genes useful according to the invention include, for example, the kanamycin gene, from pUC4K (Pharmacia Biotech) by restricting the plasmid with XhoI and filling in the 5' overhang. This plasmid DNA is then restricted with PstI and the fragment containing the kanamycin gene is then gel purified. Other useful antibiotic resistance genes are well-known in the art, including the genes encoding chlorainphenicol acetyl transferase, ampicillin, and tetracycline.

A vector of the invention which is intended for manufacture in bacteria will include in addition to the papillomavirus replication elements described herein, for example, a bacterial origin of replication and a gene encoding a selectable marker. The vector DNA will be transformed into a bacterial host, and the host grown under selection conditions. Plasmid DNA is then prepared according to conventional means.

Delivery of Episomal Vector to Host Cell

Vectors of the invention may be delivered to a host cell via any one of a number of vector delivery means. The invention is not limited by the mode of delivery of the vector to the host cell. Transfer of a vector of the invention to a host cell can be accomplished via any of the following, including but not limited to direct injection of naked DNA, for example, using a gene gun, transfection using calcium phosphate coprecipitation, fusion of the target cell with a liposomal vehicle, erythrocyte ghosts or spheroplasts carrying DNA, plasmid and viral vector-mediated transfer, DNA protein complex-mediated gene transfer such as receptor-mediated gene transfer, and viral infection.

Receptor-mediated gene transfer is dependent upon the presence of suitable ligands on the surfaces of cells which will allow specific targeting to the desired cell type followed by internalization of the complex and expression of the DNA. One form of receptor-mediated gene transfer is wherein a DNA vector is conjugated to antibodies which target with a high degree of specificity cell-surface antigens (Wong and Huang, 1987, Proc. Nat. Aca. Sci. 84:7851; Roux et al., 1989, Proc. Nat. Aca. Sci. 86::9079; Trubetskoy et al., 1992, Bioconjugate Chem. 3:323; and Hirsch et al., 1993, Transplant Proceedings 25:138). Nucleic acid may be attached to antibody molecules using polylysine (Wagner et al., 1990, Proc. Nat. Aca. Sci. 87:3410; Wagner et al., 1991, Proc. Nat. Aca. Sci. 89:7934) or via liposomes.

Increased expression of DNA derived from ligand-DNA complexes taken up by cells via an endosomal route has been achieved through the inclusion of endosomal disruption agents, such as influenza virus hemagglutinin fusogenic peptides, either in the targeting complex or in the medium surrounding the target cell. The fusogenic peptide of the HA molecule is a modified form of HA which retains two important functions of HA. It allows for fusion of the targeted DNA/ligand complex to the cell membrane, but without the host cell sialic acid-binding specificity of the natural molecule. Instead, host cell binding specificity is conferred by the ligand/receptor interaction. The modified HA fusogenic peptide also retains the HA function of endosomal uptake, thus allowing for uptake of the complex into the host cell via membrane fusion, and the endosomal escape function of HA, which allows for escape of the enveloped DNA from the endosomal/lysosomal destruction pathway. The fusogenic peptide may include the HA amino acid sequence GLFGAIAGFIGAGTGGMIAGGC (SEQ ID NO.: 9).

1. Viral Vectors

Recombinant viral vectors as well as other DNA transfer schemes can be used in practice of the present invention. A recombinant viral vector of the invention will include DNA of at least a portion of a viral genome which portion is capable of infecting the target cells. By "infection" is generally meant the process by which a virus transfers genetic material to its host or target cell. Preferably, the virus used in the construction of a vector of the invention is also rendered replication-defective to remove the effects of viral replication on the target cells. In such cases, the replication-defective viral genome can be packaged by a helper virus in accordance with conventional techniques. Generally, any virus meeting the above criteria of infectiousness and capabilities of functional gene transfer can be employed in the practice of the invention.

Suitable viruses for practice of the invention include but are not limited to, for example, papovavirus and herpesvirus, well known to those skilled in the art; suitable vector packaging cell lines for stably transducing mammalian cell lines are known in the art.

It will be appreciated that when viral vector schemes are employed for gene transfer according to the invention, the use of an attenuated or a virulent virus also may be desirable.

2. Delivery of-Gene via DNA-Protein Complexes

Targeted gene delivery is also achieved according to the invention using a DNA-protein complex. Such DNA-protein complexes include DNA complexes with a ligand that interacts with a target cell surface receptor. Cell surface receptors are thus utilized as naturally existing entry mechanisms for the specific delivery of genes to selected mammalian cells. It is known that most, if not all, mammalian cells possess cell surface binding sites or receptors that recognize, bind and internalize specific biological molecules, i.e., ligands. These molecules, once recognized and bound by the receptors, can be internalized within the target cells within membrane-limited vesicles via receptor-mediated endocytosis. Examples of such ligands include but are not limited to proteins having functional groups that are exposed sufficiently to be recognized by the cell receptors. The particular proteins used will vary with the target cell.

Typically, glycoproteins having exposed terminal carbohydrate groups are used although other ligands such as antibodies or polypeptide hormones, also may be employed. Using this technique the phototoxic protein psoralen has been conjugated to insulin and internalized by the insulin receptor endocytotic pathway (Gasparro, Bio-chem. Biophys. Res. Comm. 141(2), pp. 502509, Dec. 15, 1986); the hepatocyte specific receptor for galactose terminal asialoglycoproteins has been utilized for the hepatocyte-specific transmembrane delivery of asialoorosomucoid-poly-L-lysine non-covalently complexed to a DNA plasmid (Wu, G. Y., J. Biol. Chem., 262(10), pp. 44294432, 1987); the cell receptor for epidermal growth factor has been utilized to deliver polynucleotides covalently linked to EGF to the cell interior (Myers, European Patent Application 86810614.7, published Jun. 6, 1988); the intestinally situated cellular receptor for the organometallic vitamin $B_{12}$-intrinsic factor complex has been used to mediate delivery to the circulatory system of a vertebrate host a drug, hormone, bioactive peptide or immunogen complexed with vitamin $B_{12}$ and delivered to the intestine through oral administration (Russel-Jones et al., European patent Application 863 07849.9, published Apr. 29, 1987); the mannose-6-phosphate receptor has been used to deliver low density lipoproteins to cells (Murray, G. J. and Neville, D. M., Jr., J. Bio. Chem. Vol. 225 (24), pp. 1194–11948, 1980); the cholera toxin binding subunit receptor has been used to deliver insulin to cells lacking insulin receptors (Roth and Maddox, J. Cell. Phys. Vol. 115, p. 151, 1983); and the human chorionic gonadotropin receptor has been employed to deliver a ricin a-chain coupled to HCG to cells with the appropriate HCG receptor in order to kill the cells (Oeltmann and Heath, J. Biol. Chem, Vol 254, p. 1028 (1979)). Ligands selected from biotin, biotin analogs and biotin receptor-binding ligands, and/or folic acid, folate analogs and folate receptor-binding ligands to initiate receptor mediated transmembrane transport of the ligand complex, as described in U.S. Pat. No. 5,108,921.

Generally, a ligand is chemically conjugated by covalent, ionic or hydrogen bonding to the nucleic acid. A ligand for a cell surface receptor may be conjugated to a polycation such as polylysine with ethylidene diamino carbodiimide as described in U.S. Pat. No. 5,166,320. DNA may be attached to an appropriate ligand in such a way that the combination thereof or complex remains soluble, is recognized by the receptor and is internalized by the cell. The DNA is carried along with the ligand into the cell, and is then expressed in the cell. The protein conjugate is complexed to DNA of a transfection vector by mixing equal mass quantities of protein conjugate and DNA in 0.25 molar sodium chloride. The DNA/protein complex is taken up by cells and the gene is expressed.

Delivery of the foreign DNA into the target cell may also be achieved via the DNA construct's association with an endosomal disruption agent, such as the influenza hemagglutinin fusogenic peptide, as described above.

3. Liposomal Gene Transfer

Liposomes have been used for non-viral delivery of many substances, including nucleic acids, viral particles, and drugs. A number of reviews have described studies of liposome production methodology and properties, their use as carriers for therapeutic agents and their interaction with a variety of cell types. See, for example, "Liposomes as Drug Carriers," Wiley and Sons, NY (1988), and "Liposomes from Biophysics to Therapeutics," Marcel Dekker, NY (1987). Several methods have been used for liposomal delivery of DNA into cells, including poly-L-lysine conjugated lipids (Zhou et al., Biochem. Biophys. Acta. 1065:8–14, 1991), pH sensitive immunoliposomes (Gregoriadis, G., Liposome Technology, Vol I, II, III, CRC, 1993), and cationic liposomes (Felgner et al., Proc. Natl. Acad. Sci., USA, 84:7413–7417, 1987). Positively charged liposomes have been used for transfer of heterologous genes into eukaryotic cells (Felgner et al., 1987, Proc. Nat. Aca. Sci. 84:7413; Rose et al., 1991, BioTechniques 10:520). Cationic liposomes spontaneously complex with plasmid DNA or RNA in solution and facilitate fusion of the complex with cells in culture, resulting in delivery of nucleic acid to the cell. Philip et al. 1994, Mol. and Cell. Biol. 14:2411, report the use of cationic liposomes to facilitate adeno-associated virus (AAV) plasmid transfection of primary T lymphocytes and cultured tumor cells.

Delivery of an agent using liposomes allows for non-invasive treatment of diseases. Targeting of an organ or tissue type may be made more efficient using immunoliposomes, i.e., liposomes which are conjugated to an antibody specific for an organ-specific or tissue-specific antigen. Thus, one approach to targeted DNA delivery is the use of loaded liposomes that have been made target-specific by incorporation of specific antibodies on the liposome surface.

Host Cells Useful in the Invention

The cells targeted for in vivo or ex vivo gene transfer in accordance with the invention include any cells to which the delivery of the therapeutic gene is desired. Eukaryotic cells are preferred, and particularly mammalian cells. For example, brain cells, cells of the central nervous system, nerve cells, gut cells, skin cells, kidney cells, endothelium, lung cells, liver cells, cells of the immune system such as T-cells, B-cells, and macrophages.

Dosage, Mode of Administration and Pharmaceutical Formulation

Vector DNA may be formulated as naked DNA for parenteral administration or as a transfection mixture. In the latter case, the transfection mixture may be assembled just prior to use. In the case of a pharmaceutical composition, the vector DNA includes the papillomavirus MO and MME sequences, optionally, the E1 and E2 genes, and a gene whose expression is intended to have some beneficial therapeutic effect on the cells of the recipient. For optimal efficiency of delivery of naked DNA to a target tissue, it is preferred that the vector DNA be delivered at 10–100 ug/10,000 cells, optimally about 50 ug/10,000 cells.

The DNA may be exchanged into isotonic phosphate free buffer and sterile filtered, and then aliquotted into suitable vials. The vials may be stored at 4° C., 20° C. or 80° C. or alternatively the mixture may be freeze dried from a buffer containing an appropriate carrier and bulking agent. In these cases, the dosage form is reconstituted with a sterile solution before administration.

For delivery of vector DNA in vivo or ex vivo, the vector containing a gene of physiological importance, such as replacement of a defective gene or an additional potentially beneficial gene function, is expected to confer long term genetic modification of the cells and be effective in the treatment of disease.

For example, a patient that is subject to a viral or genetic disease, or who is being vaccinated against a virus or pathogen, may be treated in accordance with the invention via in vivo or ex vivo methods. For example in vivo treatments, a vector of the invention can be administered to the patient, preferably in a biologically compatible solution or a pharmaceutically acceptable delivery vehicle, by ingestion, injection, inhalation or any number of other methods. The dosages administered will vary from gene to gene, disease to disease, and from patient to patient; a "therapeutically effective dose" will be determined by the level of enhancement of function of the transferred genetic material balanced against any risk or deleterious side effects. Monitoring levels of gene introduction, gene expression and/or the presence or levels of the encoded therapeutic protein will assist in selecting and adjusting the dosages administered. Generally, a composition including the vector will be administered in a single dose in the range of 10 ng–1 mg/kg body weight, preferably in the range of 100 ng–100 ug/kg body weight, such that at least one copy of the therapeutic gene is delivered to each target cell. Vector DNA may be administered as a single dose, or in multiple doses, as needed. The therapeutic gene will, of course, be associated with appropriate regulatory sequences for expression of the gene in the target cell.

Ex vivo treatment is also contemplated within the present invention. Cell populations can be removed from the patient or otherwise provided, transduced with a therapeutic gene in accordance with the invention, then reintroduced into the patient. In general, ex vivo cell dosages will be determined according to the desired therapeutic effect balanced against any deleterious side-effects. Such dosages will usually be in the range of $10^5$–$10^8$ cells per patient, daily weekly, or intermittently; preferably $10^6$–$10^7$ cells per patient.

EXAMPLES

The following examples describe detailed embodiments of the invention in which a given gene of interest is introduced and stably maintained in a specific host cell, or a specific disease is exemplified for treatment according to the invention.

Example 1

Recombinant Host Cells of the Invention

Recombinant vectors of the invention may be used in the in vitro production of a protein of interest, for example, cell factories may be prepared by transforming a host cell with a recombinant vector of the invention. The vector will contain the papillomavirus MO, MME and a gene encoding the protein of interest, and may optionally include the genes encoding the HPV or BPV E1 and E2 genes. Alternatively, a cell line may be prepared that carries in its chromosome the E1 and E2 genes, such that the encoded proteins are in trans to the papilloma episomal sequences. A cell line carrying a recombinant vector of the invention, whether it carries the E1 and E2 genes in cis or in trans to the vector permits stable, high level expression of proteins of therapeutic value in cultured mammalian cells.

Where it is desirable according to the invention to determine the copy number (per haploid or diploid host cell genome) of a recombinant vector of the invention. Vector copy number may be determined as described herein for copy number determination of the BPV origin-containing plasmids.

Described below is an example in which a host cell line is engineered to contain chromosomal copies of the E1 and E2 genes. This cell line is advantageous for production of a desired protein or RNA in that it can be transfected with a vector of the invention encoding the desired protein or RNA, and cultured to produce that molecule.

We constructed several cell lines constitutively expressing the E1 and E2 proteins. Expression of these proteins was directed from integrated constructs for E1 protein from CMV promoter (cell line CHO212) and for E2 protein from HAP70 promoter (cell line CHO49). In the cell line CHO4.15 which expresses both E1 and E2, the E1 protein was expressed from SRαpromoter and the E2 protein from HSP70 promoter. Selection of the respective cell lines and amplification of the expression units of interest was achieved by utilizing the glutamine synthetase minigene from the pSVLGS.1 plasmid according to the protocol described earlier (Bebbington and Hentschel, 1987). Expression of E1 and E2 was identified by immunoprecipitation using specific rabbit polyclonal sera (data not shown) and by in vivo replication assays. The three cell lines and the parental CHO cells were transfected with the BPV-1 origin containing plasmid pUC/Alu in combination with E1 and E2 expression vectors. The cell line CHO4.15 which expresses both E1 and E2, supports replication of the origin plasmids in the absence of erogenous E1 and E2. The E2 expressing cell line, CHO49, supports replication in the presence of an E1 expression vector, but fails to do so without erogenous E1. The E1 expressing cell line, CHO212, supports replication only in the presence of an E2 expression vector. In the parental CHO cell line, co-expression of both E1 and E2 is required for replication. No replication of pUC/Alu can be detected in the absence of E1 and E2.

Figure 7A:
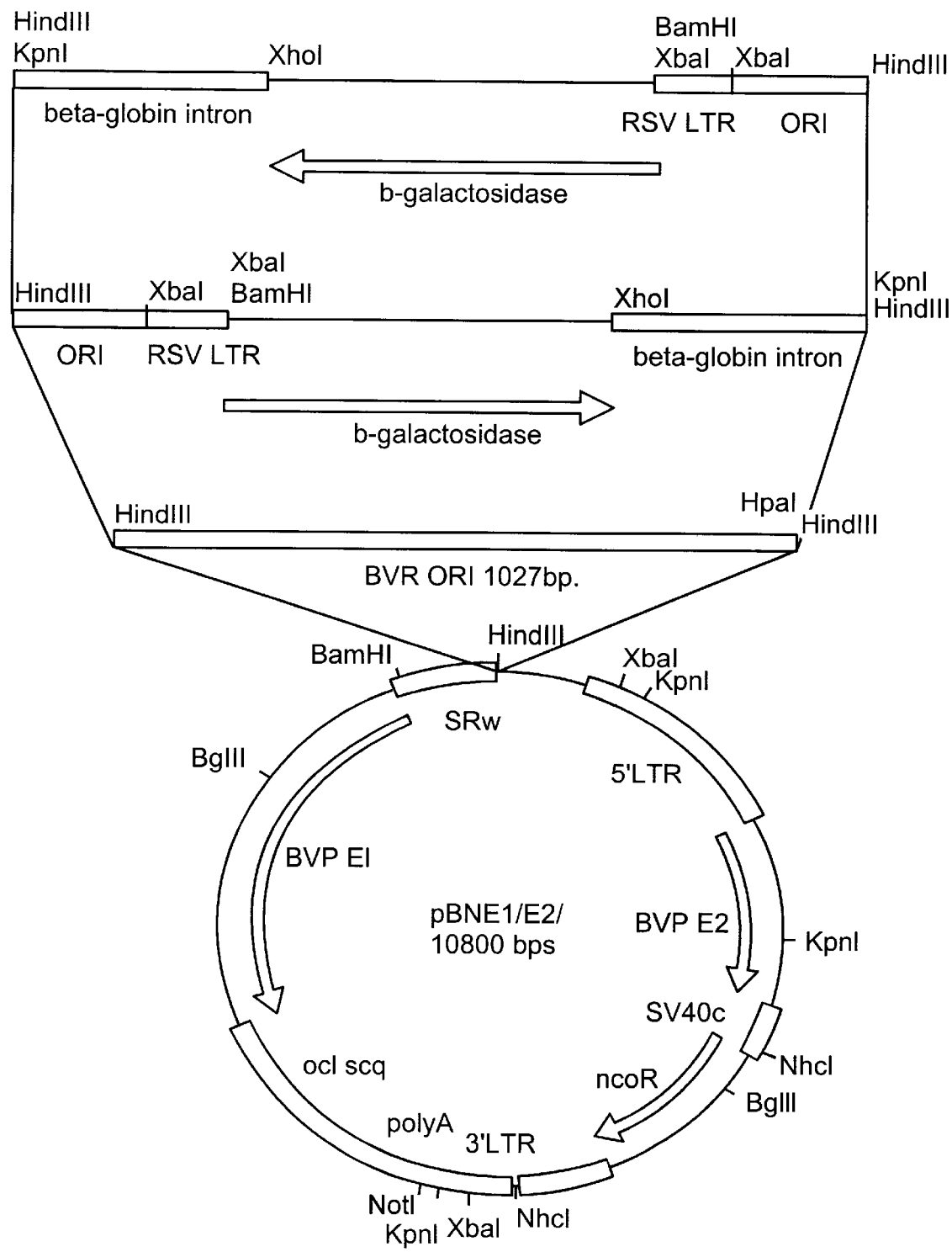
FIG. 7A is a schematic illustration of a plasmid in which E1 expression is under the control of the SR promoter.
Figure 7B:
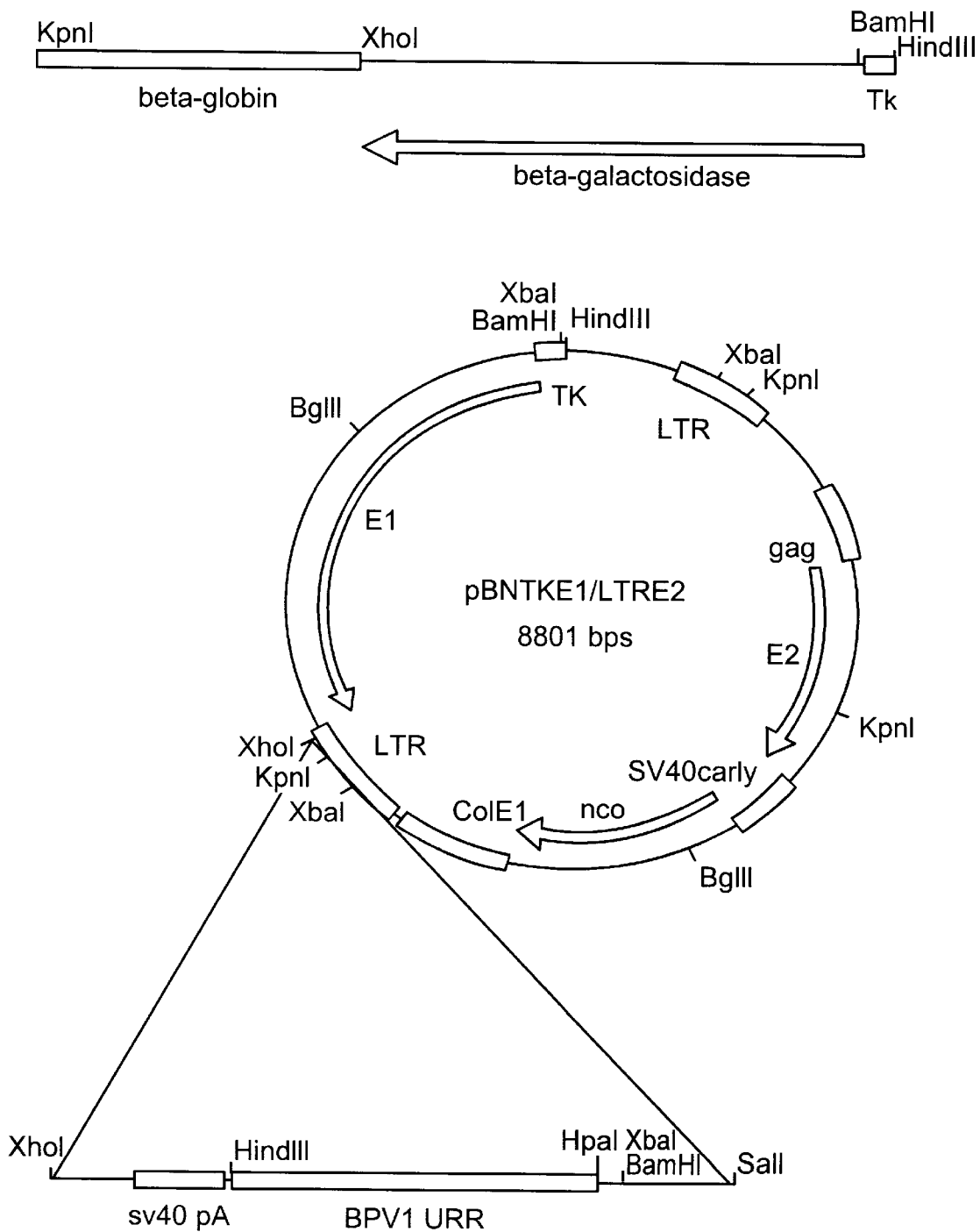
FIG. 7B is a schematic illustration of a plasmid in which E1 expression is under the control of the Thymidine kinase promoter.
Figures 1, 7C:
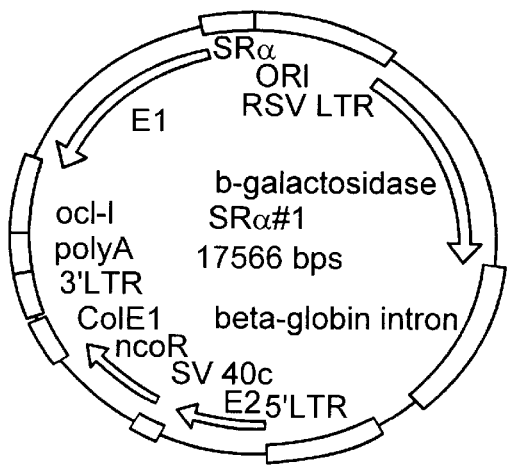
FIG. 7C is a schematic representation of the plasmid maps shown in FIGS. 7A and 7B.
Figures 2, 7C:
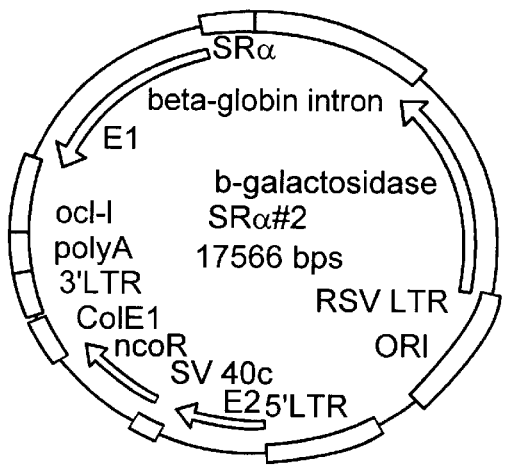
Figures 3, 7C:
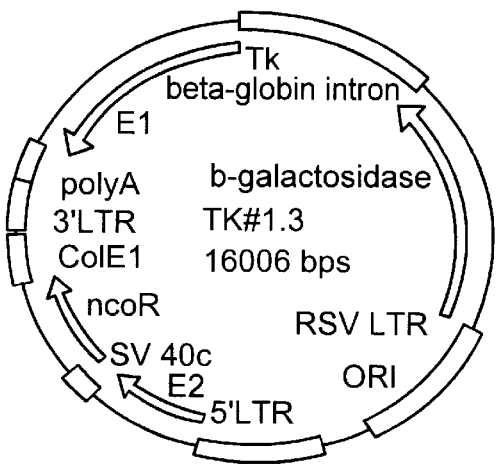
Figures 4, 7C:
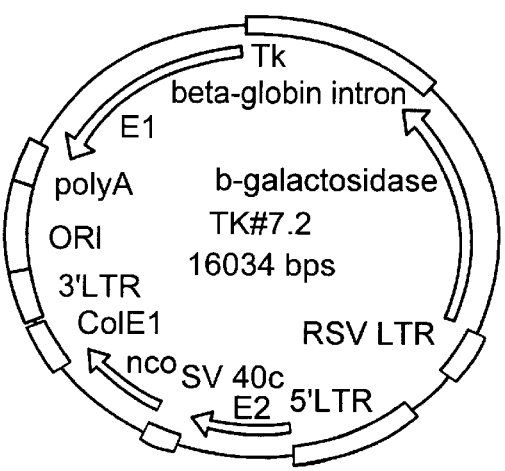

The cell line CHO4.15 is transformed with a vector of the invention, for example, the pBN/TKE1-0 vector shown in detail in FIG. 7B. Alternatively, where transient high level expression of the gene of interest is desired, the vector pBNE1, shown in FIG. 7A may be used to produce relatively higher quantities of the protein of interest. We have observed MO/MME vector persistence in CHO4.15 cells for at least 80 cell generations with a copy number loss less than 10% over 80 generations. Each of these vectors contains the beta-galactosidase reporter gene. However, as is described below, the beta-gal gene can be removed and substituted with a gene of interest. The transformed cells are grown under conditions, as described in Materials and Methods, to produce the encoded molecule of interest.

Example 2

E2 Transcriptional Activator Mutants

The invention also encompasses the use of E2 point mutants which are defective in the E2 transcriptional activator function and competent in the replication function. Such E2 mutants are incorporated into the episomal vector system of the invention. Point mutations have been made in the gene encoding this protein which eliminate the transcriptional activating activity of the protein without affecting the ability of the resultant protein to stably maintain (MO+MME)-containing plasmids in transfected cells.

The mutants were made by selected mutation of amino acids which are believed to lie in hydrophilic domains (i.e., hydrophilic domains of between about 4–15 amino acids) and/or alpha helical domains at the protein surface. Such mutants are made, for example, by amino acid substitutions in the alpha helix region 2 (amino acid residues 23–49) and helix 3 (amino acids residues 62–82), and by then changing basic or acidic amino acids to a small hydrophobic residue. The mutation is introduced into the E2 gene using oligonucleotide-directed mutagenesis in M 13 phage. It is within the scope of the invention to locate additional point mutations which abolish the transcription activating activity of E2 without deleteriously affecting its replication function.

Figure 14A:
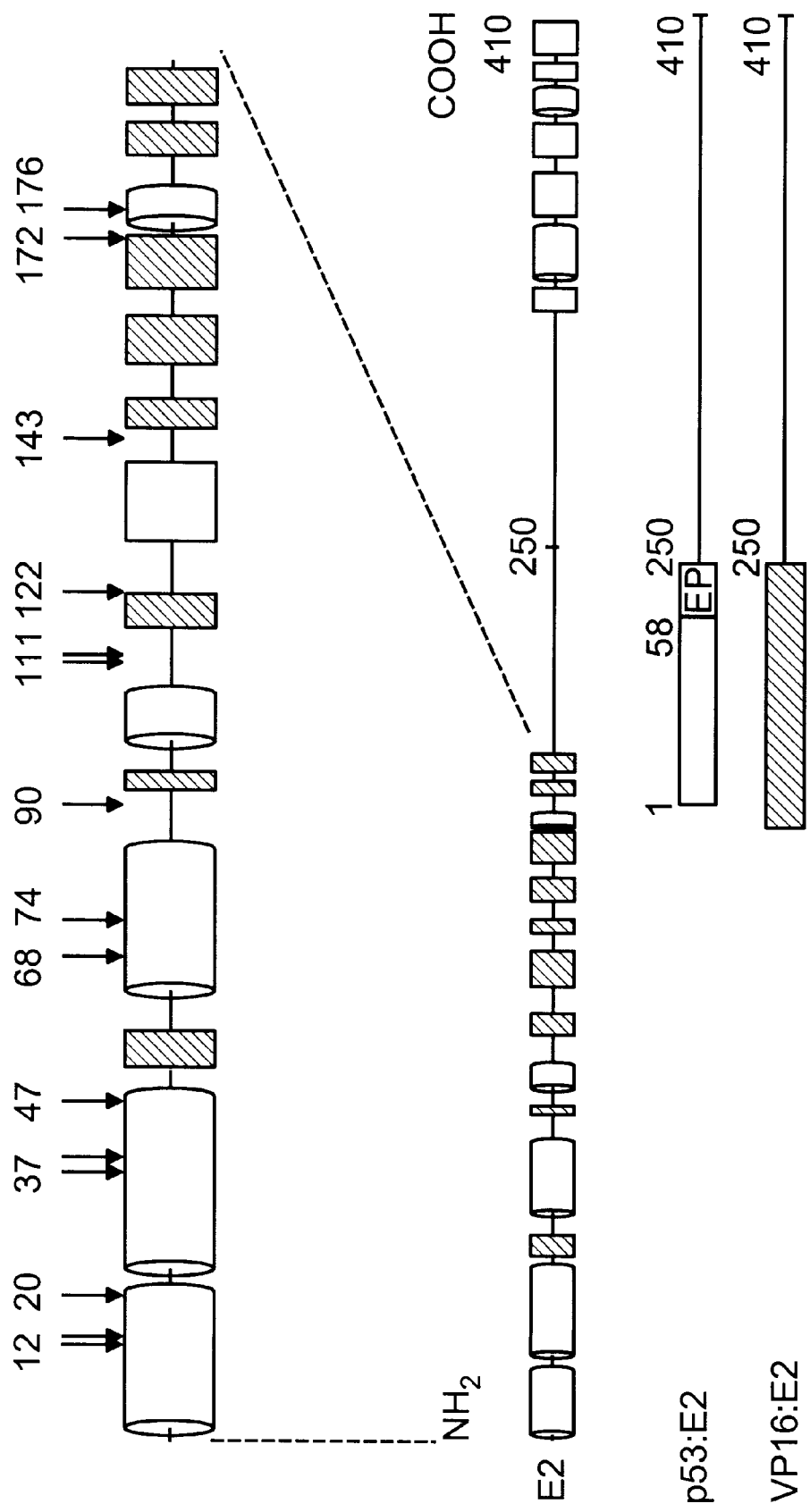
FIG. 14A is a schematic representation of the designed E2 point mutations and chimeric E2 proteins.

FIG. 14A depicts the location of the mutations and schematically illustrates the predicted secondary structure (cylinder—-helix, shaded box—-sheet) for the N-terminal and the X-ray structure for the C-terminal portions of the E2 protein. The locations of mutations are indicated by arrows; numbers refer to the position of the mutated residue in the E2 protein.

Figure 14B:
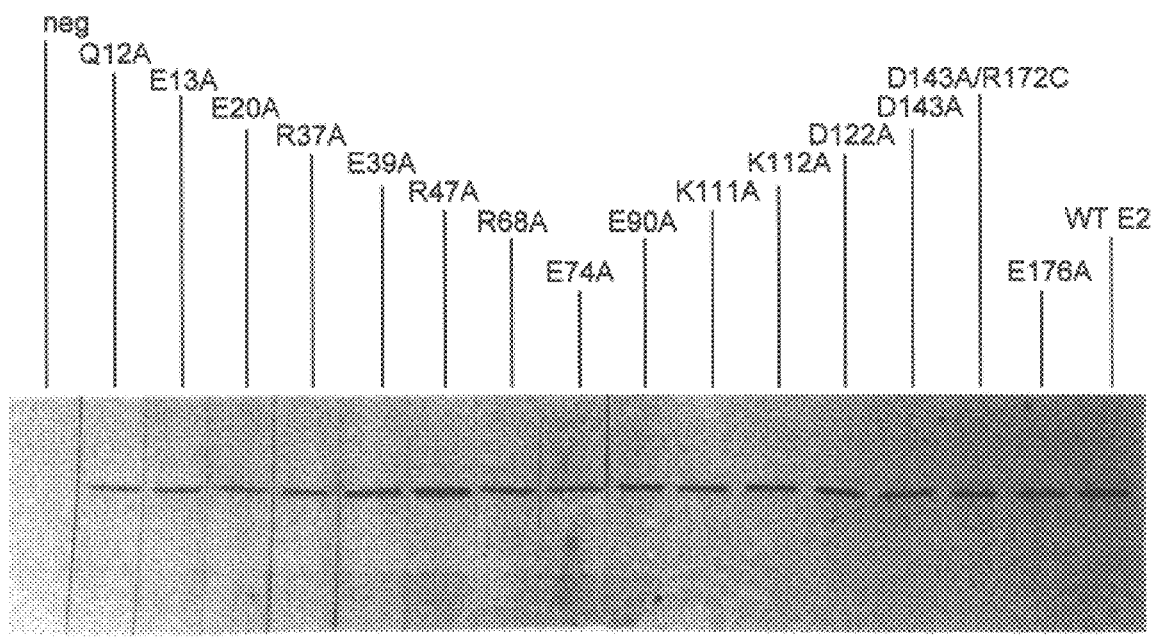
FIG. 14B shows an immunoblots of the E2 proteins.

FIG. 14B demonstrates that mutant E2 proteins are stably expressed in cells. Immunoblots of the E2 proteins are shown. Cell lysates were prepared from COS-7 cells containing a wild-type (WT) or mutant E2 expression plasmid. 30 µl of cell lysate was loaded on each lane. The negative control lysate was prepared from cells electroporated with carrier DNA. The substitutions of amino acids are shown on the lettering, and single amino acid code is used; the numbers refer to the positions of the substituted residues in the E2 protein.

Figure 15A:
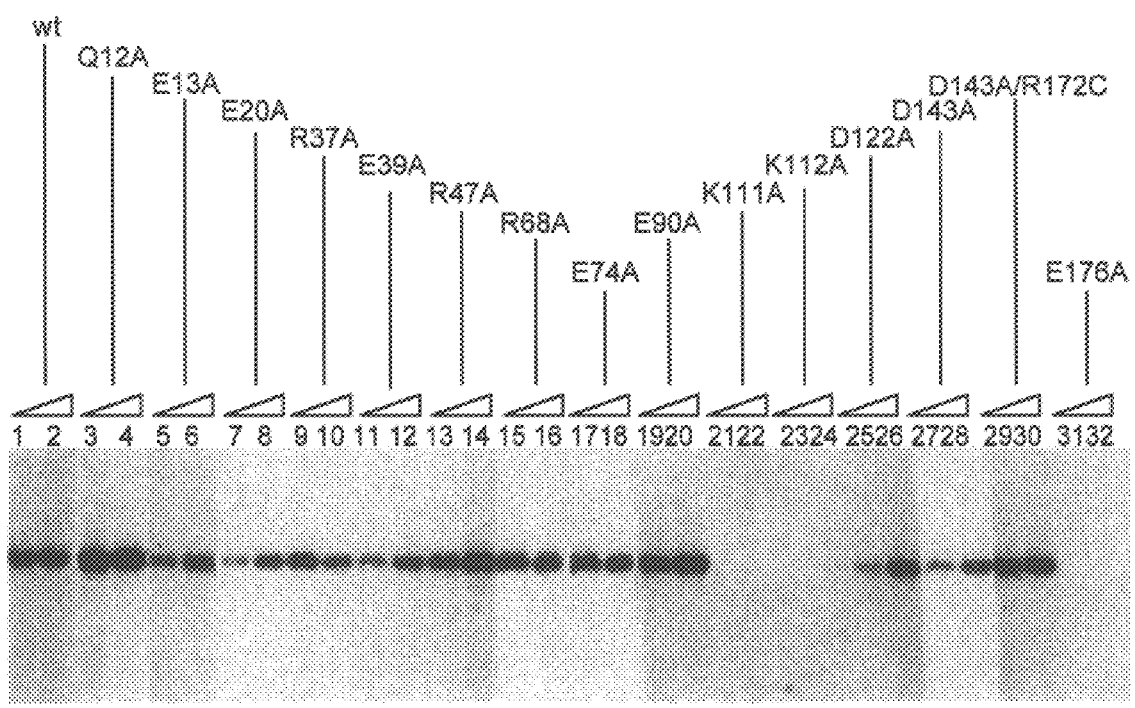
FIG. 15A shows the transient replication properties of the mutated E2 proteins in CHO cells.

FIG. 15A shows the replication activation properties of the mutant E2 proteins using transient replication assays of the mutated E2 proteins in CHO cells. Cells were electroporated with 100 ng of reporter plasmid pUC/Alu, 500 ng of pCGEag and 250 ng of pCGE2, which expresses wild-type E2 or its derivatives. Cells were harvested either 36 or 48 hours after electroporation, low mol.wt. DNA was digested with DpnI and linearizing enzyme HindIII and analyzed by the Southern blotting.

Figure 15B:
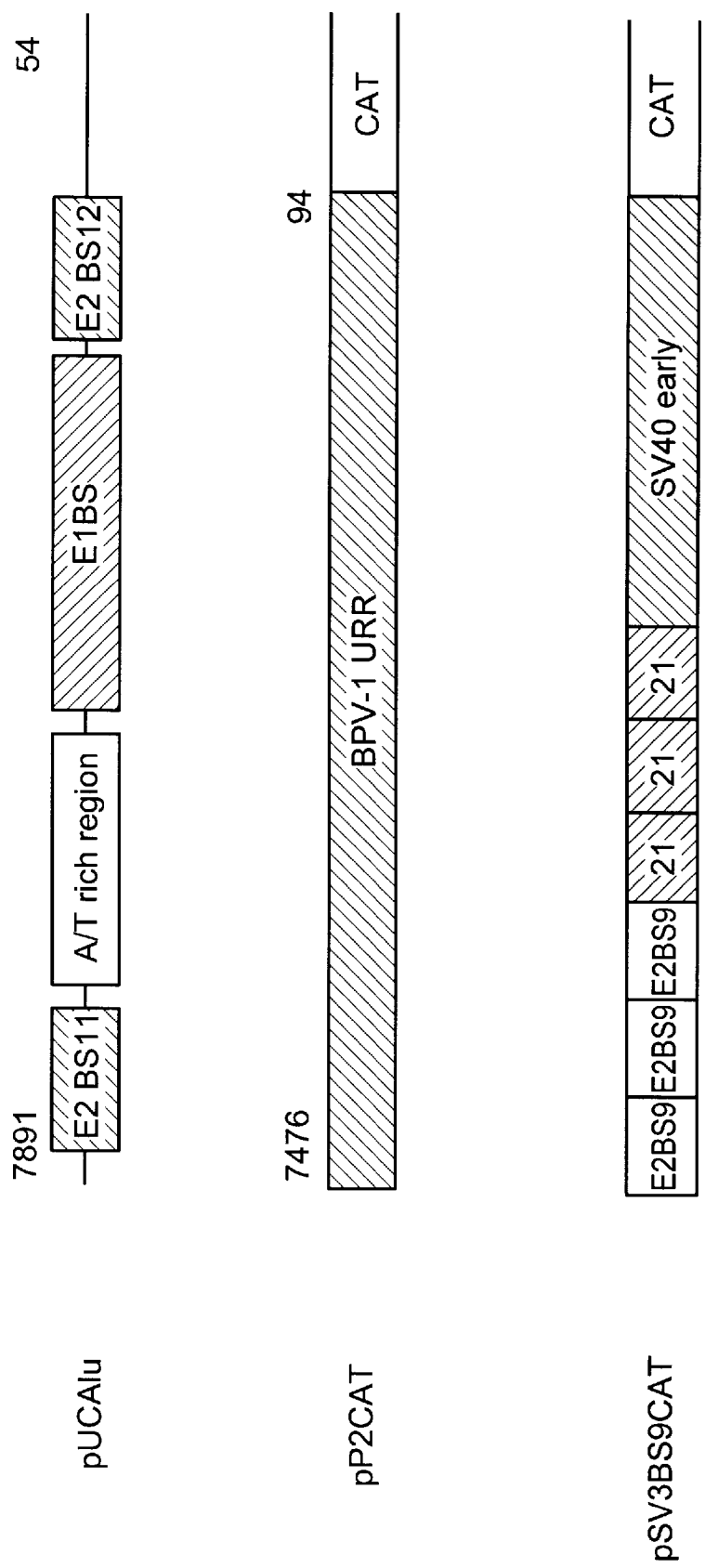
FIG. 15B shows the structure of the reporter plasmids used. The numbers indicate nucleotide positions in the BPV URR sequence. pUCAlu was used for transient replication studies. pPCAT and pSV3BS9CAT are the CAT reporter plasmids used in transcriptional activation assays.

FIG. 15B shows the reporter constructs for determining transcription activation properties of the E2 mutants, and origin constructs for determining activation of replication. The numbers indicate nucleotide positions in the BPV URR sequence. pUCAlu was used for transient replication studies. pPCAT and pSV3BS9CAT are the CAT reporter plasmids used in transcriptional activation assays.

Figure 16:
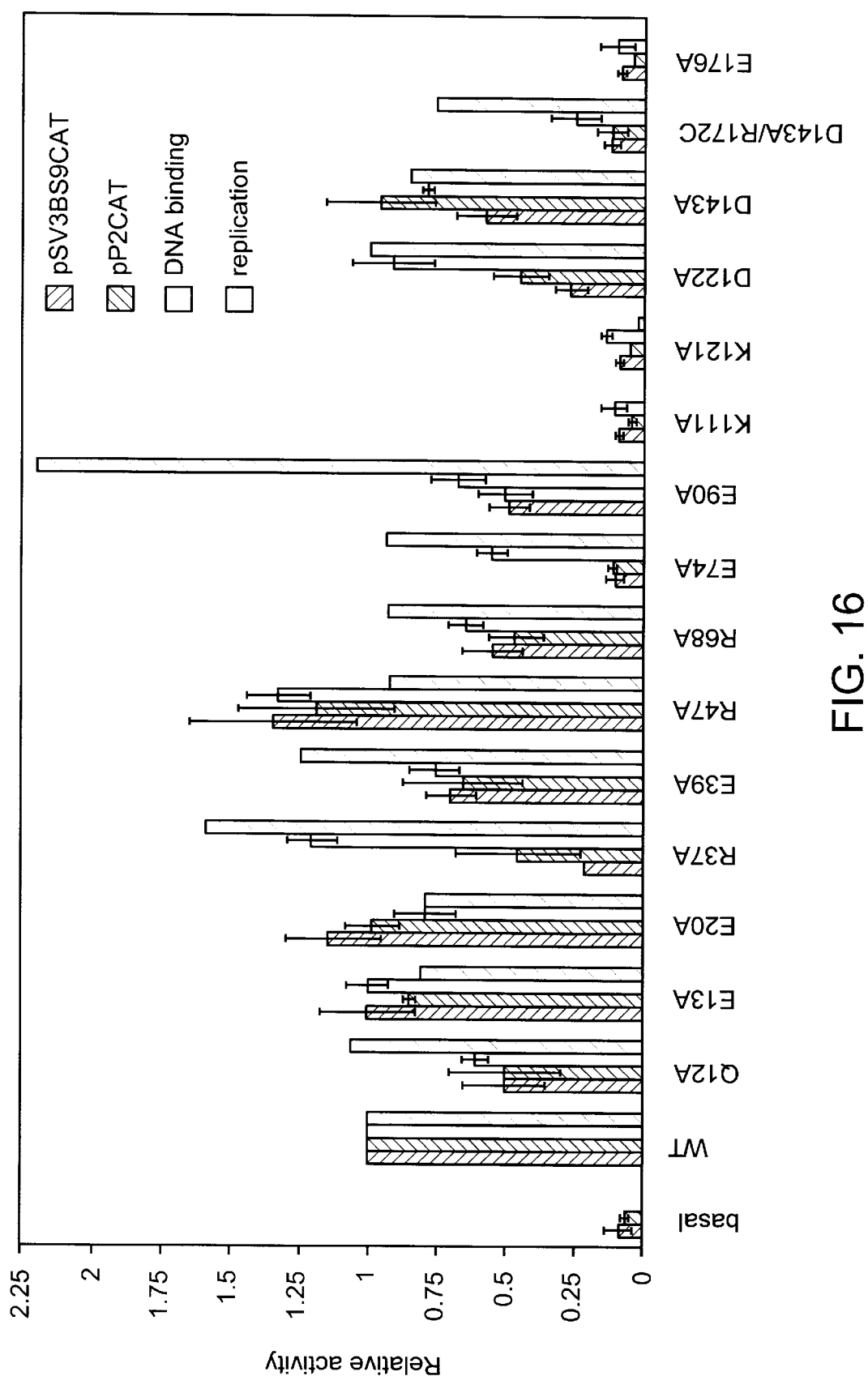
FIG. 16 represents a comparison of transactivation and DNA binding abilities of E2 protein mutants.
Figure 17A:
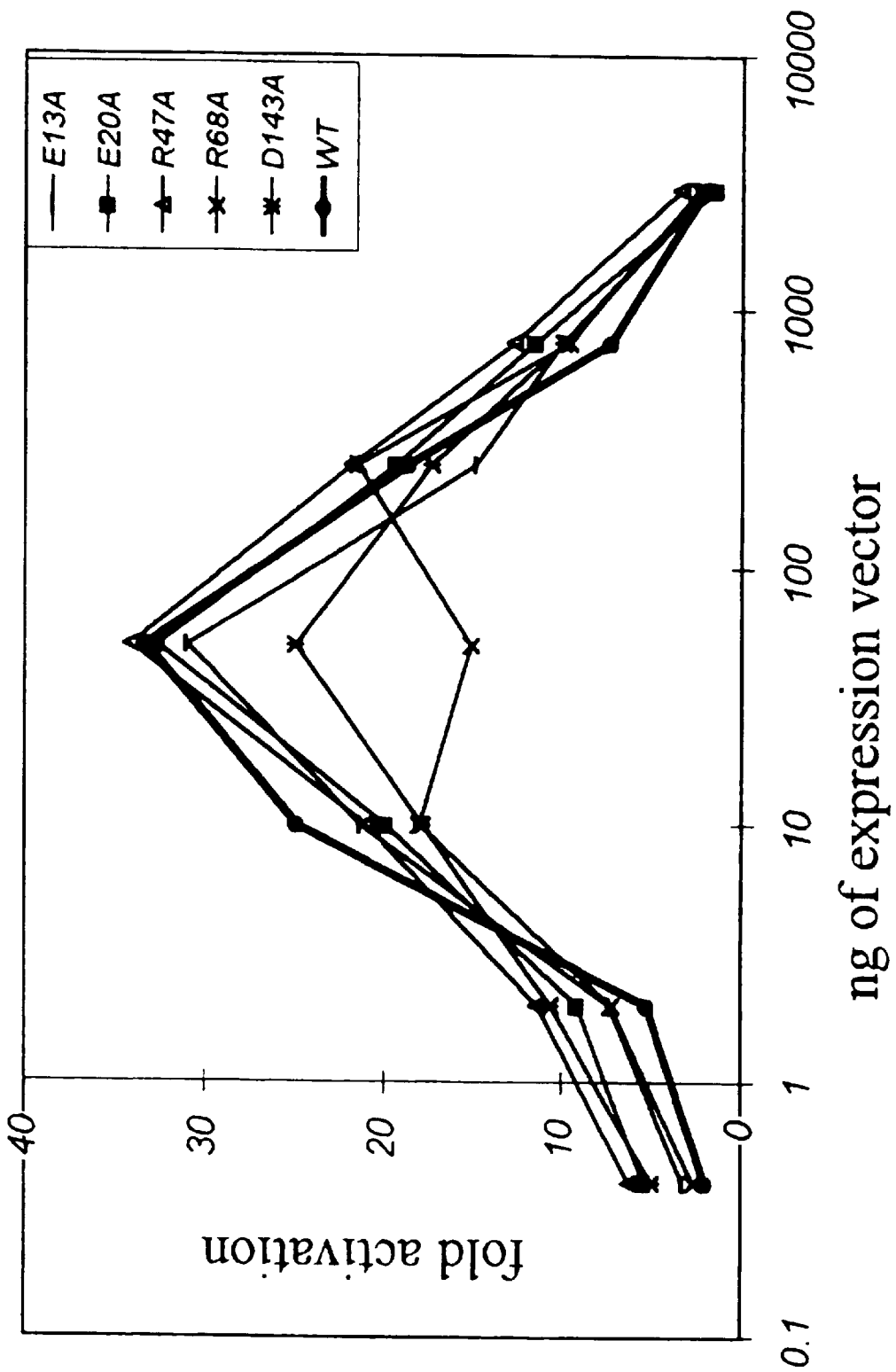
FIG. 17 (Parts A–D) shows results of a transient transcription assay for the E2 protein mutants. A. Mutations with nearly wild-type properties in transient transcription assay. B. Mutations, which transcriptional activity has decreased to 50% of that of the wild-type protein. C. Inactive mutations for transcription. D. Transcriptional properties of chimeric proteins p53:E2 and VPI6:E2.
Figure 17B:
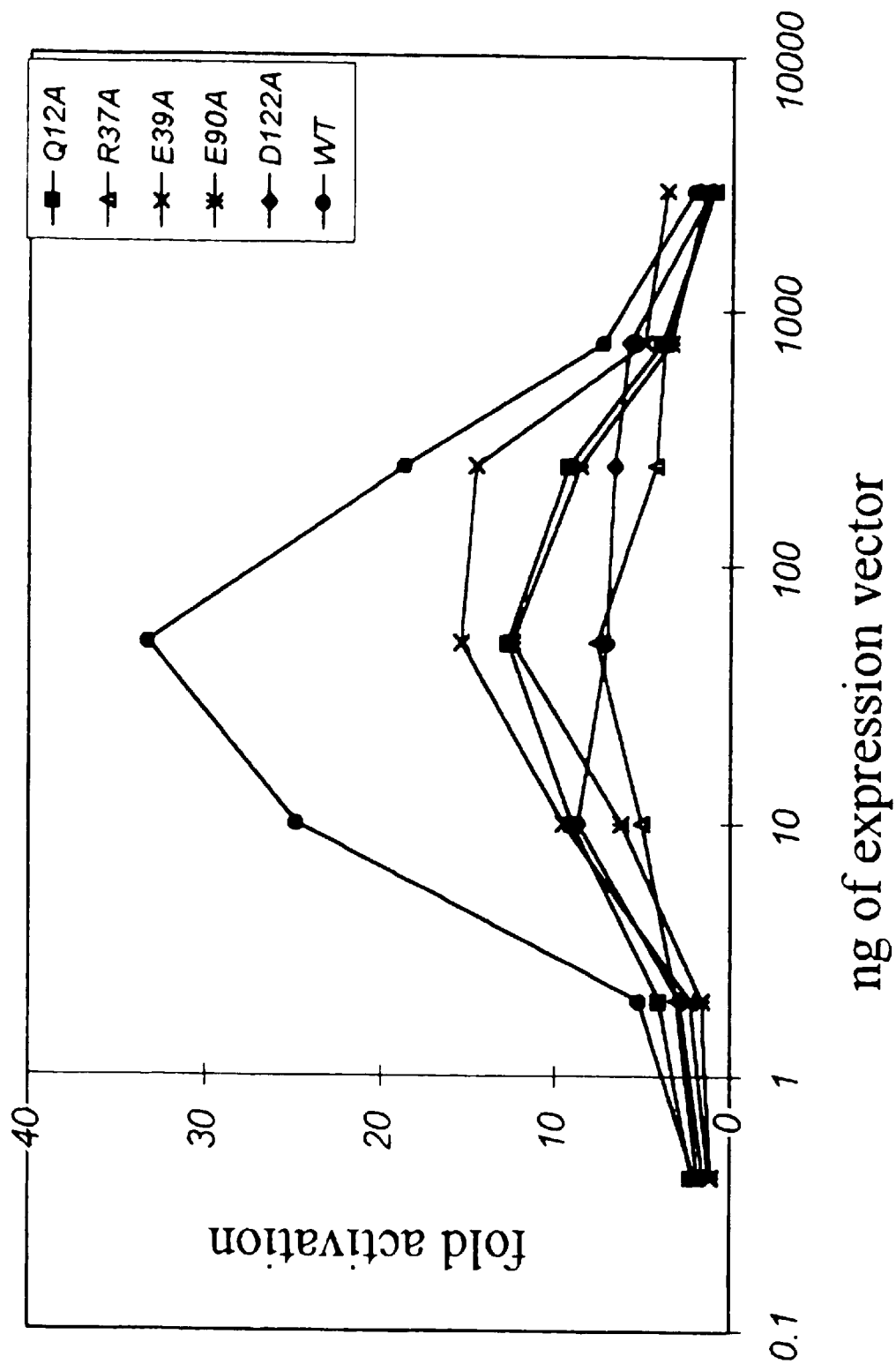
Figure 17C:
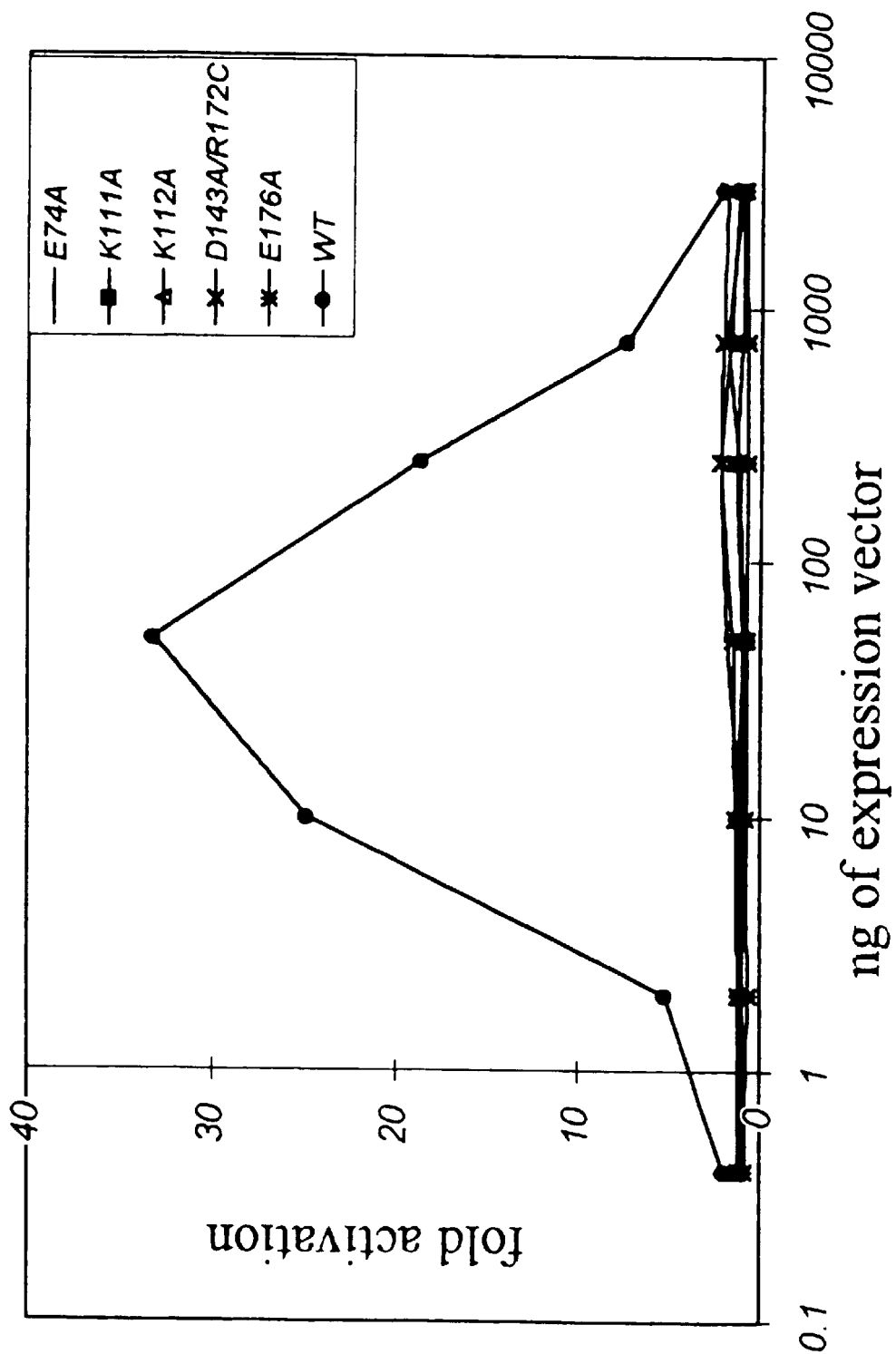
Figure 17D:
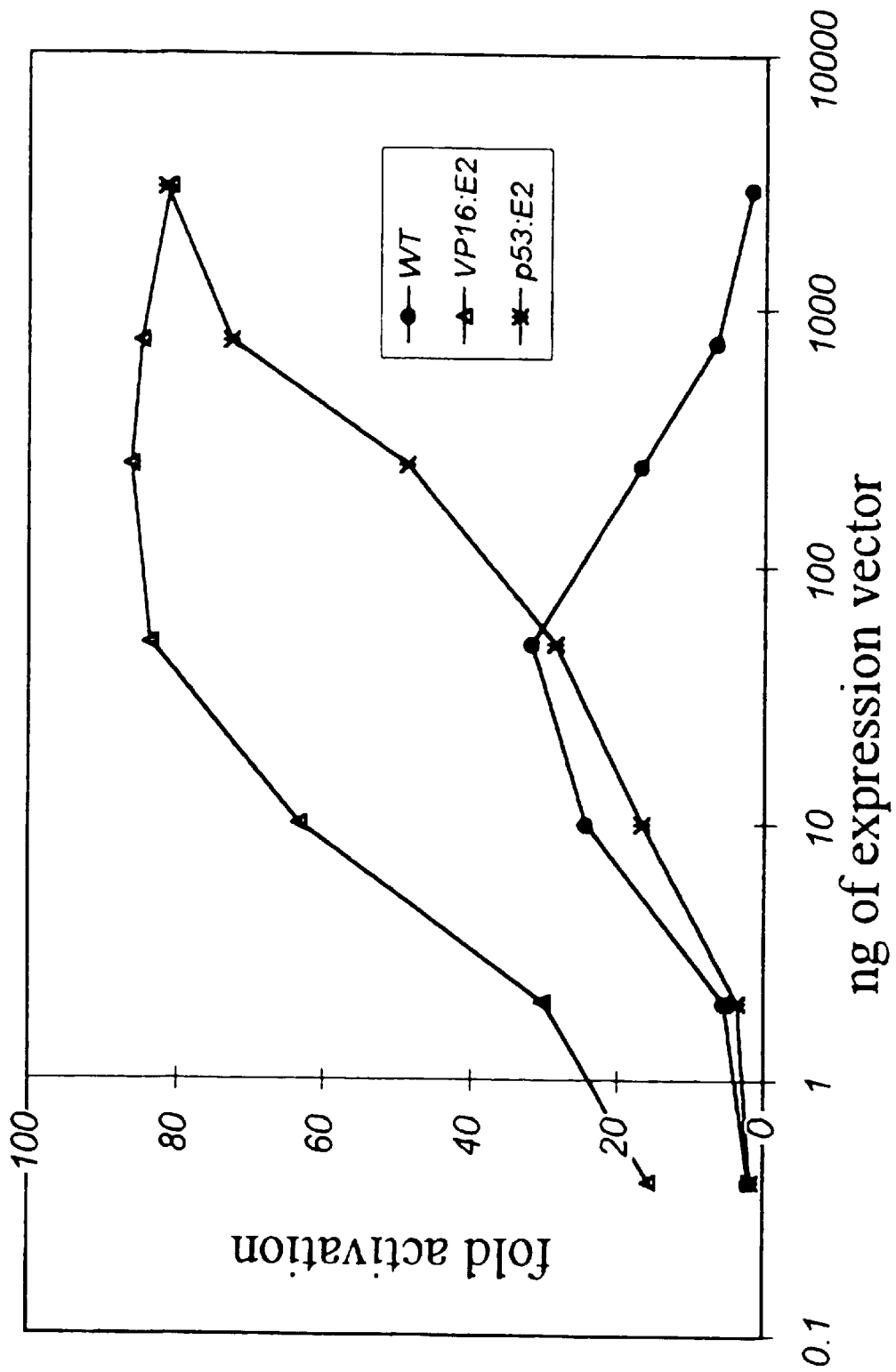
Figure 18A:
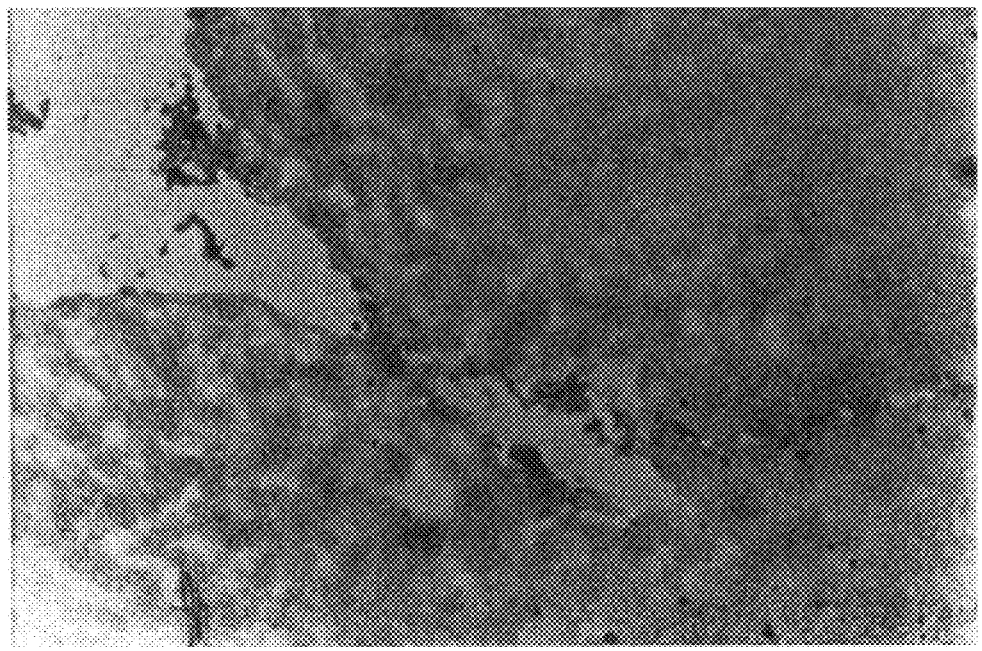
FIG. 18 (Parts A–F) shows results of staining for beta-galactosidase activity in brain striatum sections, where panels A–F represent plasmid DNA dissolved in cerebrospinal fluid (A–D) or PBS (E, F).
Figure 18B:
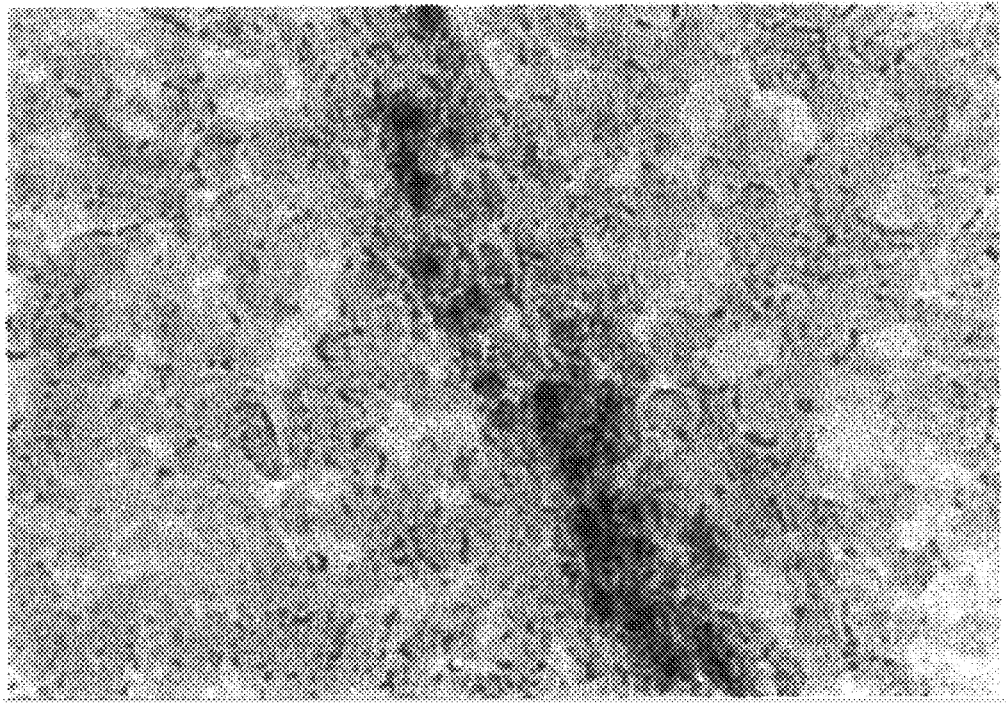
Figure 18C:
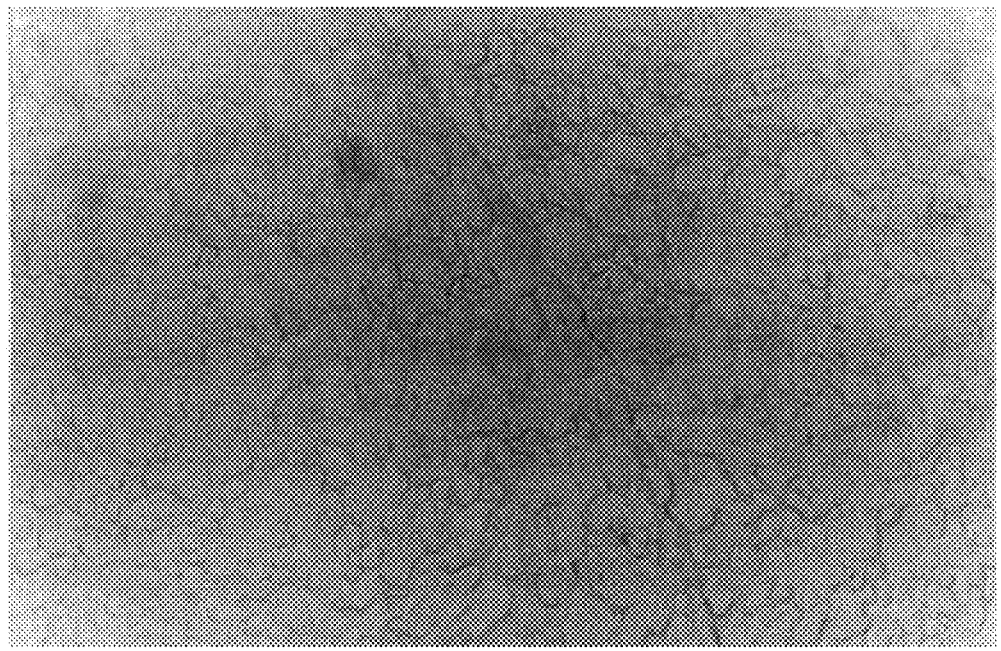
Figure 18D:
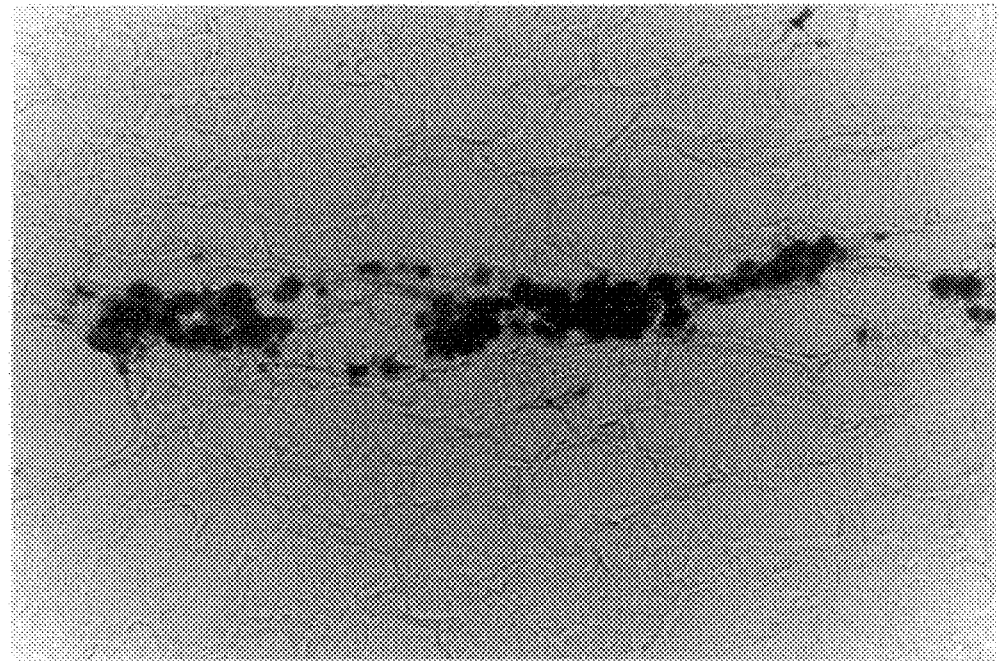
Figure 18E:
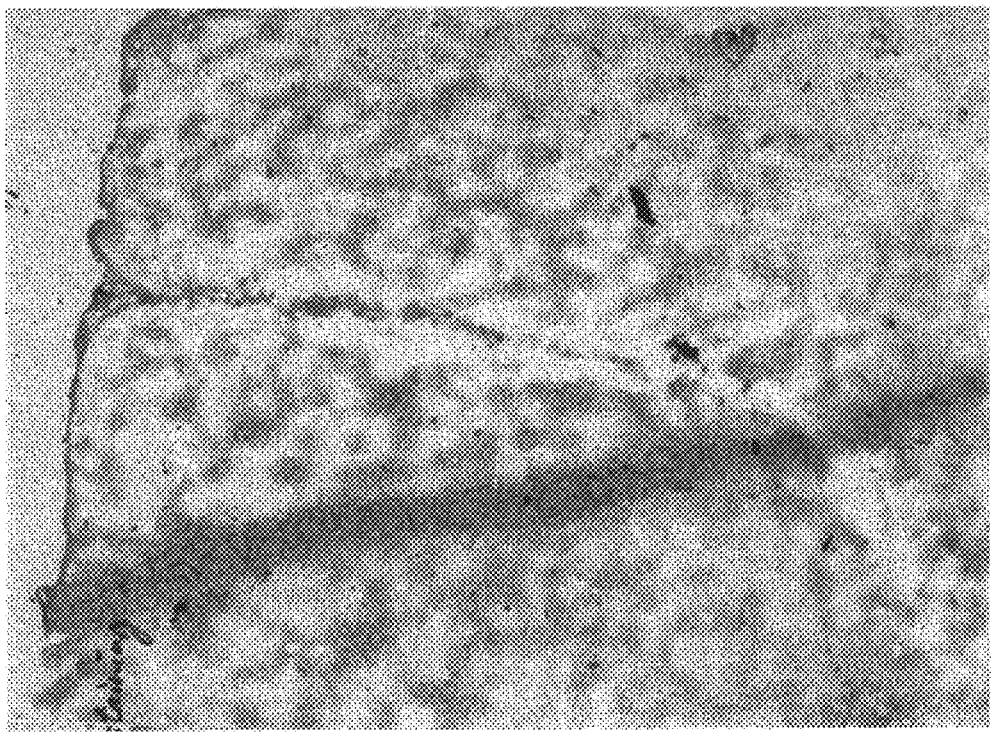
Figure 18F:
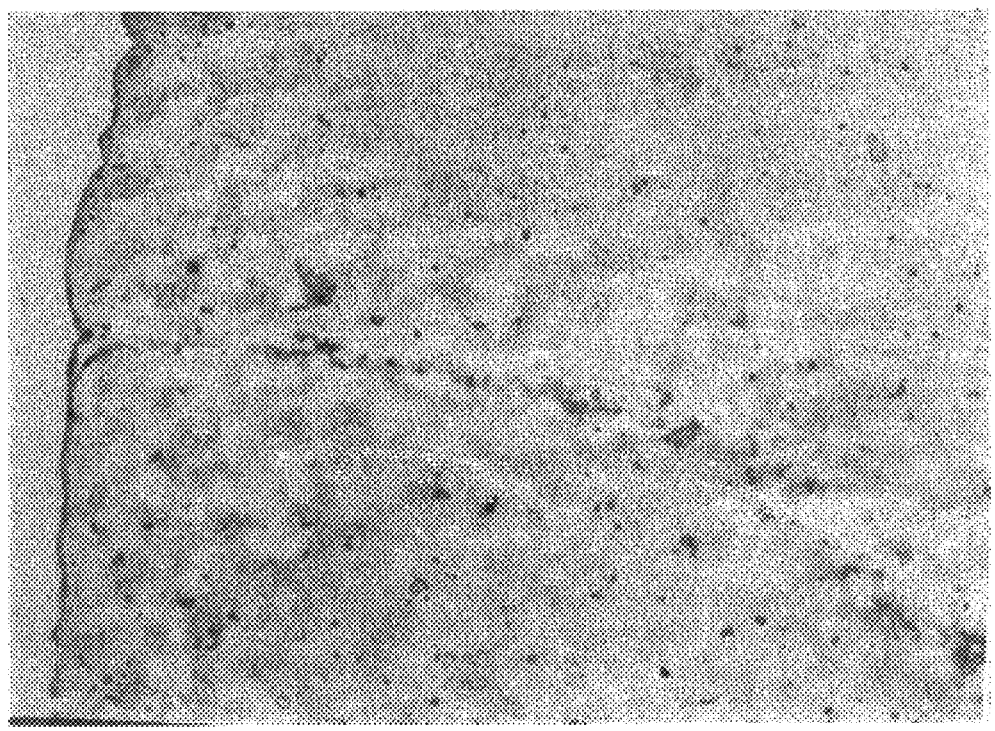

FIG. 16 shows the transcription activation activity of the mutant E2 proteins and represents comparison of transactivation and DNA binding abilities of E2 protein mutants. The radioactive signals of gel-shift assays were quantitated with the use of a PhosphorImager (data not shown). After scanning, the E2 specific signal of wtE2 protein was set as 1. For transcription assay CHO cells were electroporated with 250 ng of respective reporter and 250 ng of pCGE2 or its derivatives. Normalized CAT activities were determined 40 hours after transfection. In all cases the values shown represent the results of three independent transfection experiments.

FIG. 17 demonstrates of the self-squelching feature of some of the E2 mutants at the higher concentrations. Transient transcription assay for the E2 protein mutants were performed as described in Materials and Methods. CHO cells were transfected with increasing amounts of the expression vector for E2 mutants or chimeric E2 proteins, as indicated, and with 250 ng of reporter plasmid pSV3BS9CAT. Normalized CAT activities were determined 40 hours after transfection. Each point represents the result obtained in three independent transfection assays. FIG. A. Mutations with nearly wild-type properties in transient transcription assay. B. Mutations, which transcriptional activity has decreased to 50% of that of the wild-type protein. C. Inactive mutations for transcription. D. Transcriptional properties of chimeric proteins p53:E2 and VP16:E2.

The mutants R37A (i.e., Arg-37→Ala), E74A (Glutamic Acid-74→Ala), D122A, D143A/R172C are particularly useful according to the invention because they are defective or crippled for transcriptional activation of promoters are essentially wild type for activation of replication in the transient replication assay.

Table 1 shows codons which were mutated, giving rise to the described amino acid changes.

TABLE 1

| codon start | wt codon | mutated codon | change | name |
| --- | --- | --- | --- | --- |
| 2716 | AGA | GCA | Arg-37 Ala | R37A |
| 2827 | GAA | GCA | Glu-74 Ala | E74A |
| 3121 | CGC | TGC | Arg-172 Cys | R172C |

E2 mutants such as those described herein can be tested for their ability to replicate MO+MME containing plasmids using the MO/MME replication assays described herein. The use of such E2 mutants is advantageous in that it eliminates, or at least minimizes, the possibility of aberrant activation of cellular genes including proto-oncogenes by the E2 protein, and represents an improved safety feature of this system. The safety of the vector is increased by the inactivation of the E2 transcription activation domain. Furthermore, the specificity of the vector and also its safety is increased because the mutant form of E2 would not activate E2 responsive promoters which may be present on the vector. In addition, the mutant form of E2 described herein would not transactivate E2 enhancers. It is known that some E2 binding sites constitute an E2 enhancer. These binding sites, when present on a vector according to the invention as part of the MME, would not be transactivated by mutant E2, thus further reducing the deleterious effects of wild-type E2 in this vector system. Use of the mutant form of E2 disclosed herein also may improve the specificity of tissue-specific promoters or other promoters which drive expression of a therapeutic (or other) gene on the vector. That is, because promoters may have some leakiness, transcription from a leaky promoter driving E2 gene expression may result in E2 expression and initiation of E2 transactivation of an E2-driven promoter and gene. However, the inventive mutant form of E2 is defective in transactivation and therefore would not initiate E2-responsive transcription even in the presence of a leaky promoter driving mutant E2 gene expression. Therefore, a tissue-specific promoter which drives expression of a gene of interest on a vector of the invention may be more tightly regulated as a result of use of an E2 mutant according to the invention.

Example 3

Stable Persistence of Vector of the Invention in Muscle Cells

Figure 19:
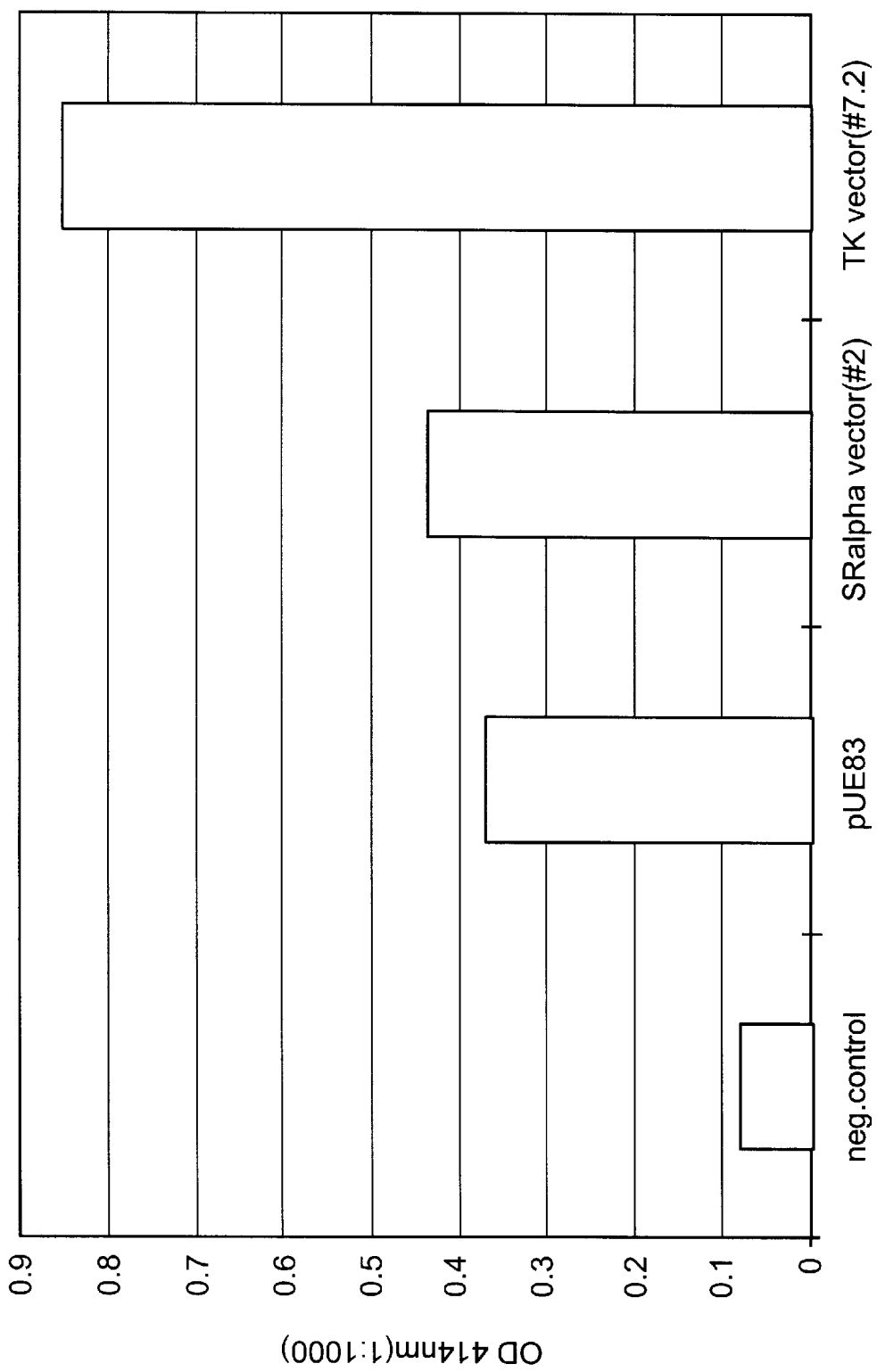
FIG. 19 is a bar graph showing results of β-galactosidase reporter gene expression in mice after injection of a vector of the invention containing a β-galactosidase gene.

The usefulness of the E1/E2/MO/MME episomal vector system for in vivo delivery to, and long term expression in, mammalian muscle is demonstrated as follows. Generation of a humoral immune response to genes expressed in these vectors has been achieved by expression in muscle by direct intramuscular injection of vector DNA, testifying to its utility as an in vivo vaccine system. Briefly, the E1/E2/MO/MME plasmid is directly injected into mice intramuscularly into each leg; 50 ul saline containing 100 ug plasmid DNA is injected into the quadraceps muscle of each leg. Injections were performed in 1, 2, or 3 sets at 3 week intervals (Ulmer, 1993, Science 259;1745). FIG. 19 shows the results of the experiment. 0.1 mg of plasmid DNA was injected into mice intramuscularly. Serum samples were collected at 90 days after injection. Antibodies were measured by ELISA using recombinant β-galactosidase as antigen. The OD at 414 was read using a 1:1000dilution of serum. "Neg. Control"refers to saline alone injection; "pUE83" refers to an RSV LTR promoter-driven β-gal expression cartridge cloned into pUC19; "SRalpha vector" refers to the E1/E2/MO/MME plasmid containing the E1 and E2 genes driven by the SRalpha promoter and the same β-gal expression cartridge; and "TK vector" refers to the E1 /E2/MO/MME plasmid containing the E1 and E2 genes driven by the TK promoter and the same β-gal expression cartridge. The MME in the SRalpha and TK vectors is the region in the BPV URR corresponding to positions 6958–1.

Example 4

Stable Persistence of Vector of the Invention in Brain Cells

The following example demonstrates persistent, long term expression of lacz reporter gene in the central nervous system using an E1/E2/MO/MME vector harboring a lacZ reporter gene (FIG. 18). Briefly, the vector SR-alpha #2 (SR promoter directing E1 and E2 expression in the E1/E2/MO/MME plasmid described in detail above) was injected into an adult rat brain striatum region (bregma +1.7 dex. +2.5). Total amount of vector DNA was 50 micrograms in 5 microliter of PBS. Plasmid DNA was dissolved in PBS (panels E and F) or artificial cerebrospinal fluid (panels A–D). The results showed that P -galactosidase activity was detected histochemically by X-GAL regular staining protocol on frozen brain tissue slices after 5 days (panels A and B), two weeks (panels C and D) and three months (panels E and F) exposure. Control animals were injected with PBS (E) or CSF (panels A and C). Therefore, the plasmid was stably maintained in brain tissue for as long as three months after introduction.

The above example demonstrates the utility of vectors of the invention in gene therapy and in providing animal models of disease and therapy.

REFERENCES

The following references are referred to hereinabove and their contents are hereby incorporated by reference.

Bebbington,C. R. and Hentschel, C. C. G (1987) In Glover, D. M. (ed.), DNA cloning—A practical Approach. IRL Press, Oxford, Vol 111, pp. 163–188.

Berg, L., Lusky, M., Stenlund, A., and Botchan, M. R. (1986) Repression of bovine papillomavirus replication is mediated by a virally encoded trans-factor. Cell,$_{13}$ 46, 753–762.

Blitz, I. L and Laimins, L. A. (1991) The 68-kilodalton E1 protein of bovine papillomavirus is a DNA binding phoshoprotein which associates with the E2 transcriptional activator in vitro. J Virol., 65, 649–656.

Bonne-Andrea, C., Santucci, S. and Clertant, P. (1 995) Bovine papillomavirus E1 protein can, by itself, efficiently drive multiple rounds of DNA synthesis in vitro. J Virol., 69, 3201–3205.

Botchan, M. R., Berg, L., Reynolds, J. and Lusky, M. (1986) The bovine papillomavirus replicon. In D. Evered and S. Clark (eds. ), Papillomaviruses. John Wiley&Sons, New York, pp. 5367.

Chiang, C.-M., Ustav, M., Stenlund, A., Ho, T. F., Broker, T. R. and Chow, L. T. (1992) Viral E1 and E2 proteins support replication of homologous and heterologous papillomaviral origins. Proc. Natl. Acad. Sci. USA, 89, 5799–5803.

DePamphilis, M. L. (1993) Eukaryotic DNA replication: anatomy of the origin. Annu. Rev. Biochem., 62, 29–63.

DeVilliers, E. M. (1989) Heterogeneity of the human papillomavirus group. J Virol., 63, 48984903.

Dostatni, N., Lainbert, P. F., Sousa, R., Ham, J., Howley, P. M. and Yaniv, M. (1991) The functional BPV-1 E2 trans-activating protein can act as a repressor by preventing formation of the initiation complex. Genes Dev., 5, 1657–1671.

Dvoretzky, l., Shober, R, Chattopadhyay, S. K. and Lowy, D. R. (1 980) A quantitative in vitro focus assay for bovine papillomavirus. Virology, 103, 369–375.

Gilbert, D. M. and Cohen, S. N. (1987) Bovine papillomavirus plasmids replicate randomly in mouse fibroblasts throughout S phase of the cell cycle. Cell, 50, 59–68.

Haugen, T. H., Cripe, T. P., Ginder, G. D., Karin, M. and Turek, L. P. (1 987) Trans-activation of an upstream early gene promoter of bovine papillomavirus-1 by a product of the viral E2 gene. EMBOJ, 6, 145–152.

Hubert, W. G. and Lambert, P. F. (1993) The 23-Kilodalton E1 phosphoprotein of bovine papillomavirus type I is nonessential for the stable plasmid replication in murine C 127 cells. J Virol., 67, 2932–2937.

Jareborg, N., Alderbom, A. and Bumett, S. (1992) Identification and genetic definition of a S bovine papillomavirus type I E7 protein and absence of a low copy-number phenotype exhibited by E5, E6 and E7 viral mutants. J Virol., 66, 4957–4965.

Jacob, F., Brenner, S., Cuzin, F. (1963) On the regulation of DNA replication in bacteria. Cold Spring Harbor Symp. Quant. Biol., 28, 329–348.

Kirchmaier, A. L. and Sugden, B. (1995) Plasmid maintenance of derivatives of oriP of Epstein-Barr virus. J Virol., 69, 1280–1283.

Krysan, P. J., Haase, S. B. and Calos, M. P. (1989) Isolation of human sequences that replicate autonomously in human cells. Mol. Cell. Biol., 9, 1026–1033.

Kuo, S. R., Liu, J. S., Broker, T. R. and Chow, L. T. (1994) Cell-free replication of the human papillomavirus DNA with homologous viral E1 and E2 proteins and human cell extracts. J Biol. Chem., 269, 24058–24065.

Law, M. F., Lowy, D. R., Dvoretzky, l. and Howley, P. M. (1 98 1) Mouse cells transformed by bovine papillomavirus contain only extrachromosomal viral DNA sequences. Proc. Natl. Acad. Sci. USA, 78, 2727–273 1.

Li, R., Knight, J. D., Bream, G., Stenlund, A. and Botchan, M. R. (1989) Specific recognition nucleotides and their DNA context determine the affinity of E2 protein for 17 binding sites in the BPV- I genome. Genes Dev., 3, 510–526.

Lu, J. Z., Sun, Y. N., Rose, R. C., Bonnez, W. and McCance, D. J. (1993) Two E2 binding sites (E2BS) alone or one E2BS plus an A/T-rich region are minimal requirements for the replication of the human papillomavirus type 11 origin. J Virol., 67, 7131–7139.

Lusky, M. and Botchan, M. R. (1984) Characterization of the bovine papillomavirus plasmid maintenance sequence. Cell, 36, 3 9140 1.

Lusky, M. and Botchan, M. R. (1985) Genetic analysis of bovine papillomavirus plasmid type1 trans-acting replication factors. J Virol., 53, 955–965.

Lusky, M. and Botchan, M. R. (1986) A bovine papillomavirus type I encoded modulator function is dispensable for transient viral replication but is required for the establishment of the stable plasmid state. J Virol., 60, 729–742.

Middleton, T. and Sugden, B. (1994) Retention of plasmid DNA in mammalian cells is enhanced by binding of the Epstein-Barr virus replication protein EBNA-1. J Virol., 68, 4067–4071.

Mohr, I. J., Clark, R., Sun, S., Androphy, E. J., MacPherson, P., and Botchan, M. R. (1990) Targeting the E1 replication protein to the papillomavirus origin of replication by complex formation with the E2 transactivator. Science, 250, 1694–1699.

Müller, F., Seo, Y. S. and Hurwitz, J. (1994) Replication of bovine papillomavirus type I origin-containing DNA in crude extracts and with purified proteins. J Biol. Chem., 269, 17086–17094.

Nallaseth, F. S. and DePainphilis, M. (1 994) Papillomavirus contains cis-acting sequences that can supress but not regulate origins of DNA replication. J ViroL, 68, 3051–3064.

Nordström, K. (1 990) Control of plasmid replication—how do DNA iterons set the replication frequency? Cell, 63, 1121–1124.

Ravnan, J. -B., Gilbert, G. M., Ten Hagen, K. G. and Cohen, S. N. (1992) Random-choice replication of extrachromosomal bovine papillomavirus (BPV) molecules in heterogeneous clonally derived BPV-infected cell lines. J ViroL, 66, 6946–6952.

Roberts, J. M. and Weintraub, H. (1986) Negative control of DNA replication in composite SV40-bovine papillomavirus plasmids. Cell, 46, 741–752.

Russell, J. and Botchan, M. R. (1 995) Cis-acting components of human papillomavirus (BPV) DNA replication: linker substitution analysis of the HPV type 11 origin. J ViroL, 69, 651–660.

Schiller, J. T., Vass, W. C. and Lowy, R. D. (1984) Identification of a second transforming region in papillomavirus DNA. Proc. Natl. Acad. Sci. USA, 81, 7880–7884.

Spalholz, B. A., Lambert, P. F., Yee, C. L. and Howley, P. M. (1987) Bovine papillomavirus transcriptional regulation: localization of the E2-responsive elements of the long control region. J Virol., 61, 2128–2137.

Stillman, B. (1 994) Initiation of chromosomal DNA replication in eukaryotes. J Biol. Chem., 269, 7047–7050.

Struhl, K., Stinchcomb, D. T., Scherer, S. and Davis, R. W. (1979) High-frequency transformation of yeast: autonomous replication of hybrid molecules. Proc. Natl. Acad. Sci USA, 76, 1035–1039.

Svedrup, F. and Khan, S. A. (1995) Two E2 binding sites alone are sufficient to function as the minimal origin of replication of human papillomavirus type 18 DNA. J Virol., 69, 1319–1323.

Szymanski, P. and Stenlund, A. (1991) Regulation of early gene expression from the bovine papillomavirus genome in transiently transfected C 127 cells. J. ViroL, 65, 57105720.

Tsurimoto, T., Melendy, T. and Stillman, B. (1 990) Sequential initiation of lagging and leading strand synthesis by two different polymerase complexes at the SV40 DNA replication origin. Nature, 346, 534–539.

Ustav, M. and Stenlund, M. (1991) Transient replication of BPV-1 requires two viral polypeptides encoded by the E1 and E2 open reading frames. EMBO J, 10, 449–457.

Ustav, M., Ustav, E., Szymanski, P. and Stenlund, A. (1991) Identification of the origin of replication of bovine papillomavirus and characterisation of the viral origin recognition factor E1. EMBO J, 10, 4321–4329.

Ustav, E., Ustav, M., Szymanski, P. and Stenlund, A. (1 993) The bovine papillomavirus origin of replication requires a binding site for the E2 transcriptional activator. Proc. Natl. Acad Sci. USA, 90, 898–902.

Vande Pol, S. B. and Howley, P. M. (1 992) A bovine papillomavirus constitutive enhancer is essential for viral transformation, DNA replication and the maintenance of latency. J Virol., 66, 2346–2358.

Wahl, G. M. (1989) The importance of circular DNA in mammalian gene amplification. Cancer Res., 49, 1333–1340.

Weinberg, D. H., Collins, K. L., Simancek, P., Russo, A., Wold, M. S., Virshup, D. M. and Kelly, T. J. (1990) Reconstitution of simian virus 40 DNA replication with purified proteins. Proc. Natl. Acad Sci. USA, 87, 8692–8696.

Windle, B., Draper, B., Yin, Y., O'Gorman, S. and Wahl, G. M. (1991) A central role for chromosome breakage in gene amplification, deletion formation and amplicon integration. Genes Dev., 5, 160–174.

Windle, B. and Wahl, G. M. (1992) Molecular dissection of mammalian gene amplification: new insights revealed by analyses of very early events. Mutat. Res., 276, 199–224.

Yang, L., Li, R., Mohr, I. J., Clarck, R. and Botchan, M. R. (1991) Activation of BPV-1 replication in vitro by the transcription factor E2. Nature, 353, 628–632.

Yates, J., Warren., N., Reisman, D. and Sugden, B. (1984) A cis-acting element from the Epstein-Barr viral genome that permits stable replication of recombinant plasmids in latently infected cells. Proc. Natl. Acad. Sci USA, 81, 3 806–3810.

Yates, J. L., Warren, N. and Sugden, B. (1985) Stable replication of plasmids derived from Epstein-Barr virus in various mammalian cells. Nature, 313, 812–815.

Yates, J. L. and Guan, N. (1 99 1) Epstein-Barr virus—derived plasmids replicate only once per cell-cycle and are not amplified after entry into cells. J Virol., 65, 483–488.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A vector comprising 6 to 50 sequential E2 binding sites, wherein said vector does not encode a papillomaviral polypeptide other than E1 or E2, or an MO, and wherein said vector comprises a non-papillomaviral gene of interest.

2. The vector of claim 1 which further comprises a papillomavirus gene encoding E2.

3. The vector of claim 1 which further comprises a bacterial host cell origin of replication.

4. The vector of claim 1 which further comprises a gene encoding a selectable marker.

5. The vector of claim 1 wherein said gene of interest is operatively associated with regulatory sequences for expression of the gene of interest in a host cell.

6. The vector of claim 2 wherein said gene encoding E2 is operatively associated with regulatory sequences for the expression of that gene in a host cell.

7. The vector of claim 2 wherein said papillomavirus gene encoding E2 encodes a mutant form of E2 which permits replication but is defective in transcriptional activation.

8. The vector of claim 6 wherein said regulatory sequences comprise a promoter.

9. The vector of claim 8 wherein said promoter is non-native to said E2 gene.

10. The vector of claim 8 wherein said promoter is functional in more than a single tissue type.

11. The vector of claim 8 said promoter is functionally restricted to a single tissue type.

12. The vector of claim 8 wherein said promoter is a strong promoter.

13. The vector of claim 8 said promoter being one of the thymidine kinase promoter and the SR alpha promoter.

14. The vector of claim 5 wherein said regulatory sequences for expression of a gene of interest comprise a promoter.

15. The vector of claim 14 wherein said promoter is non-native to said gene of interest.

16. The vector of claim 14 wherein said promoter is functional in more than one cell type.

17. The vector of claim 14 wherein said promoter is functionally restricted to a single tissue type.

18. The vector of claim 14 wherein said promoter is a strong promoter.

19. The vector of claim 7 wherein said mutant form of E2 protein differs from the wild-type E2 in a nucleotide point mutation which translates into an amino acid substitution.

20. The vector of claim 19 wherein said amino acid substitution is R37A.

21. The vector of claim 19 wherein said amino acid substitution is E74A.

22. A vector system comprising:

(A) a first vector comprising 6 to 50 sequential E2 binding sites, wherein said vector does not encode a papillomaviral polypeptide other than E1 or E2, or an MO, and wherein said vector comprises a non-papillomaviral gene of interest; and (B) a second vector comprising a papillomavirus gene encoding E2.

23. The vector system of claim 22 wherein said papillomavirus gene encoding E2 encodes a mutant form of E2 which permits replication but is defective in transcriptional activation.

24. The vector system of claim 23 wherein said mutant form of E2 protein differs from the wild-type E2 in a nucleotide point mutation which translates into an amino acid substitution.

25. The vector system of claim 24 wherein said amino acid substitution is R37A.

26. The vector system of claim 24 wherein said amino acid substitution is E74A.

* * * * *

SEQUENCE LISTING

<160> NUMBER OF SEQ ID NOS: 9

<210> SEQ ID NO 1
<211> LENGTH: 12
<212> TYPE: DNA
<213> ORGANISM: Bovine Papillomavirus
<220> FEATURE:
<221> NAME/KEY: protein_bind
<222> LOCATION: (1)..(12)
<223> OTHER INFORMATION: BPV E2 binding site
<220> FEATURE:
<221> NAME/KEY: protein_bind
<222> LOCATION: (4)..(9)
<223> OTHER INFORMATION: N at positions 4-9 in the E2 protein binding
site can be any nucleotide.

<400> SEQUENCE: 1
accnnnnnng gt                                                                12

<210> SEQ ID NO 2
<211> LENGTH: 12
<212> TYPE: DNA
<213> ORGANISM: Bovine Papillomavirus
<220> FEATURE:
<221> NAME/KEY: protein_bind
<222> LOCATION: (1)..(12)
<223> OTHER INFORMATION: BPV URR E2 binding site 9
<220> FEATURE:
<221> NAME/KEY: protein_bind
<222> LOCATION: (5)..(8)
<223> OTHER INFORMATION: N at positions 5-8 in the E2 protein binding
site can be any nucleotide.

<400> SEQUENCE: 2
accgnnnncg gt                                                                12

<210> SEQ ID NO 3
<211> LENGTH: 1260
<212> TYPE: DNA
<213> ORGANISM: Bovine Papillomavirus
<220> FEATURE:
<221> NAME/KEY: gene
<222> LOCATION: (1)..(1260)
<223> OTHER INFORMATION: Nucleotide and amino acid sequence of the BPV1
E2 sequence
<220> FEATURE:
<221> NAME/KEY: CDS
<222> LOCATION: (10)..(1242)
<223> OTHER INFORMATION: BPV1 E2 protein

<400> SEQUENCE: 3

```
gtgaagagg atg gag aca gca tgc gaa cgt tta cat gta gcg caa gaa aca      51
          Met Glu Thr Ala Cys Glu Arg Leu His Val Ala Gln Glu Thr
            1               5                  10 caa atg cag ttg att gag aaa agt agt gat aag ttg caa gat cat ata         99
Gln Met Gln Leu Ile Glu Lys Ser Ser Asp Lys Leu Gln Asp His Ile
 15                  20                  25                  30 ctg tac tgg act gct gtt aga act gag aac aca ctg ctt tat gct gca       147
Leu Tyr Trp Thr Ala Val Arg Thr Glu Asn Thr Leu Leu Tyr Ala Ala
                 35                  40                  45 agg aaa aaa ggg gtg act gtc cta gga cac tgc aga gta cca cac tct       195
Arg Lys Lys Gly Val Thr Val Leu Gly His Cys Arg Val Pro His Ser
             50                  55                  60 gta gtt tgt caa gag aga gcc aag cag gcc att gaa atg cag ttg tct       243
Val Val Cys Gln Glu Arg Ala Lys Gln Ala Ile Glu Met Gln Leu Ser
 65                  70                  75
```

-continued

| | | |
|---|---|---|
| ttg cag gag tta agc aaa act gag ttt ggg gat gaa cca tgg tct ttg<br>Leu Gln Glu Leu Ser Lys Thr Glu Phe Gly Asp Glu Pro Trp Ser Leu<br>80                         85                    90 | 291 | |
| ctt gac aca agc tgg gac cga tat atg tca gaa cct aaa cgg tgc ttt<br>Leu Asp Thr Ser Trp Asp Arg Tyr Met Ser Glu Pro Lys Arg Cys Phe<br>95                       100                 105               110 | 339 | |
| aag aaa ggc gcc agg gtg gta gag gtg gag ttt gat gga aat gca agc<br>Lys Lys Gly Ala Arg Val Val Glu Val Glu Phe Asp Gly Asn Ala Ser<br>                   115                 120                125 | 387 | |
| aat aca aac tgg tac act gtc tac agc aat ttg tac atg cgc aca gag<br>Asn Thr Asn Trp Tyr Thr Val Tyr Ser Asn Leu Tyr Met Arg Thr Glu<br>        130                     135                 140 | 435 | |
| gac ggc tgg cag ctt gcg aag gct ggg gct gac gga act ggg ctc tac<br>Asp Gly Trp Gln Leu Ala Lys Ala Gly Ala Asp Gly Thr Gly Leu Tyr<br>145                       150                 155 | 483 | |
| tac tgc acc atg gcc ggt gct gga cgc att tac tat tct cgc ttt ggt<br>Tyr Cys Thr Met Ala Gly Ala Gly Arg Ile Tyr Tyr Ser Arg Phe Gly<br>160                       165                 170 | 531 | |
| gac gag gca gcc aga ttt agt aca aca ggg cat tac tct gta aga gat<br>Asp Glu Ala Ala Arg Phe Ser Thr Thr Gly His Tyr Ser Val Arg Asp<br>175                     180                 185               190 | 579 | |
| cag gac aga gtg tat gct ggt gtc tca tcc acc tct tct gat ttt aga<br>Gln Asp Arg Val Tyr Ala Gly Val Ser Ser Thr Ser Ser Asp Phe Arg<br>                   195                 200                205 | 627 | |
| gat cgc cca gac gga gtc tgg gtc gca tcc gaa gga cct gaa gga gac<br>Asp Arg Pro Asp Gly Val Trp Val Ala Ser Glu Gly Pro Glu Gly Asp<br>        210                     215                 220 | 675 | |
| cct gca gga aaa gaa gcc gag cca gcc cag cct gtc tct tct ttg ctc<br>Pro Ala Gly Lys Glu Ala Glu Pro Ala Gln Pro Val Ser Ser Leu Leu<br>225                       230                 235 | 723 | |
| ggc tcc ccc gcc tgc ggt ccc atc aga gca ggc ctc ggt tgg gta cgg<br>Gly Ser Pro Ala Cys Gly Pro Ile Arg Ala Gly Leu Gly Trp Val Arg<br>240                       245                 250 | 771 | |
| gac ggt cct cgc tcg cac ccc tac aat ttt cct gca ggc tcg ggg ggc<br>Asp Gly Pro Arg Ser His Pro Tyr Asn Phe Pro Ala Gly Ser Gly Gly<br>255                     260                 265               270 | 819 | |
| tct att ctc cgc tct tcc tcc acc ccc gtg cag ggc acg gta ccg gtg<br>Ser Ile Leu Arg Ser Ser Ser Thr Pro Val Gln Gly Thr Val Pro Val<br>                   275                 280                285 | 867 | |
| gac ttg gca tca agg cag gaa gaa gag gag cag tcg ccc gac tcc aca<br>Asp Leu Ala Ser Arg Gln Glu Glu Glu Glu Gln Ser Pro Asp Ser Thr<br>        290                     295                 300 | 915 | |
| gag gaa gaa cca gtg act ctc cca agg cgc acc acc aat gat gga ttc<br>Glu Glu Glu Pro Val Thr Leu Pro Arg Arg Thr Thr Asn Asp Gly Phe<br>305                       310                 315 | 963 | |
| cac ctg tta aag gca gga ggg tca tgc ttt gct cta att tca gga act<br>His Leu Leu Lys Ala Gly Gly Ser Cys Phe Ala Leu Ile Ser Gly Thr<br>320                       325                 330 | 1011 | |
| gct aac cag gta aag tgc tat cgc ttt cgg gtg aaa aag aac cat aga<br>Ala Asn Gln Val Lys Cys Tyr Arg Phe Arg Val Lys Lys Asn His Arg<br>335                       340                 345               350 | 1059 | |
| cat cgc tac gag aac tgc acc acc acc tgg ttc aca gtt gct gac aac<br>His Arg Tyr Glu Asn Cys Thr Thr Thr Trp Phe Thr Val Ala Asp Asn<br>                   355                 360                365 | 1107 | |
| ggt gct gaa aga caa gga caa gca caa ata ctg atc acc ttt gga tcg<br>Gly Ala Glu Arg Gln Gly Gln Ala Gln Ile Leu Ile Thr Phe Gly Ser<br>        370                     375                 380 | 1155 | |
| cca agt caa agg caa gac ttt ctg aaa cat gta cca cta cct cct gga<br>Pro Ser Gln Arg Gln Asp Phe Leu Lys His Val Pro Leu Pro Pro Gly<br>385                       390                 395 | 1203 | |

```
atg aac att tcc ggc ttt aca gcc agc ttg gac ttc tga tcactgccat      1252
Met Asn Ile Ser Gly Phe Thr Ala Ser Leu Asp Phe
    400                 405                 410 tgccttt                                                               1260
```

<210> SEQ ID NO 4
<211> LENGTH: 410
<212> TYPE: PRT
<213> ORGANISM: Bovine Papillomavirus

<400> SEQUENCE: 4

```
Met Glu Thr Ala Cys Glu Arg Leu His Val Ala Gln Glu Thr Gln Met
 1               5                  10                  15

Gln Leu Ile Glu Lys Ser Ser Asp Lys Leu Gln Asp His Ile Leu Tyr
             20                  25                  30

Trp Thr Ala Val Arg Thr Glu Asn Thr Leu Leu Tyr Ala Ala Arg Lys
         35                  40                  45

Lys Gly Val Thr Val Leu Gly His Cys Arg Val Pro His Ser Val Val
 50                  55                  60

Cys Gln Glu Arg Ala Lys Gln Ala Ile Glu Met Gln Leu Ser Leu Gln
 65                  70                  75                  80

Glu Leu Ser Lys Thr Glu Phe Gly Asp Glu Pro Trp Ser Leu Leu Asp
                 85                  90                  95

Thr Ser Trp Asp Arg Tyr Met Ser Glu Pro Lys Arg Cys Phe Lys Lys
            100                 105                 110

Gly Ala Arg Val Val Glu Val Glu Phe Asp Gly Asn Ala Ser Asn Thr
        115                 120                 125

Asn Trp Tyr Thr Val Tyr Ser Asn Leu Tyr Met Arg Thr Glu Asp Gly
130                 135                 140

Trp Gln Leu Ala Lys Ala Gly Ala Asp Gly Thr Gly Leu Tyr Tyr Cys
145                 150                 155                 160

Thr Met Ala Gly Ala Gly Arg Ile Tyr Tyr Ser Arg Phe Gly Asp Glu
                165                 170                 175

Ala Ala Arg Phe Ser Thr Thr Gly His Tyr Ser Val Arg Asp Gln Asp
            180                 185                 190

Arg Val Tyr Ala Gly Val Ser Ser Thr Ser Ser Asp Phe Arg Asp Arg
        195                 200                 205

Pro Asp Gly Val Trp Val Ala Ser Glu Gly Pro Glu Gly Asp Pro Ala
    210                 215                 220

Gly Lys Glu Ala Glu Pro Ala Gln Pro Val Ser Ser Leu Leu Gly Ser
225                 230                 235                 240

Pro Ala Cys Gly Pro Ile Arg Ala Gly Leu Gly Trp Val Arg Asp Gly
                245                 250                 255

Pro Arg Ser His Pro Tyr Asn Phe Pro Ala Gly Ser Gly Gly Ser Ile
            260                 265                 270

Leu Arg Ser Ser Thr Pro Val Gln Gly Thr Val Pro Val Asp Leu
        275                 280                 285

Ala Ser Arg Gln Glu Glu Glu Gln Ser Pro Asp Ser Thr Glu Glu
    290                 295                 300

Glu Pro Val Thr Leu Pro Arg Arg Thr Thr Asn Asp Gly Phe His Leu
305                 310                 315                 320

Leu Lys Ala Gly Gly Ser Cys Phe Ala Leu Ile Ser Gly Thr Ala Asn
                325                 330                 335

Gln Val Lys Cys Tyr Arg Phe Arg Val Lys Lys Asn His Arg His Arg
```

|       |     |     |     |     |     |     |     |     |     |     |     |
|-------|-----|-----|-----|-----|-----|-----|-----|-----|-----|-----|-----|
|       |     | 340 |     |     |     | 345 |     |     |     | 350 |     |
| Tyr   | Glu | Asn | Cys | Thr | Thr | Thr | Trp | Phe | Thr | Val | Ala | Asp | Asn | Gly | Ala |
|       |     | 355 |     |     |     | 360 |     |     |     | 365 |     |
| Glu   | Arg | Gln | Gly | Gln | Ala | Gln | Ile | Leu | Ile | Thr | Phe | Gly | Ser | Pro | Ser |
|       | 370 |     |     |     |     | 375 |     |     |     | 380 |     |
| Gln   | Arg | Gln | Asp | Phe | Leu | Lys | His | Val | Pro | Leu | Pro | Pro | Gly | Met | Asn |
| 385   |     |     |     |     | 390 |     |     |     | 395 |     |     |     |     | 400 |     |
| Ile   | Ser | Gly | Phe | Thr | Ala | Ser | Leu | Asp | Phe |
|       |     |     |     | 405 |     |     |     | 410 |     |

<210> SEQ ID NO 5
<211> LENGTH: 676
<212> TYPE: DNA
<213> ORGANISM: Bovine Papillomavirus
<220> FEATURE:
<221> NAME/KEY: protein_bind
<222> LOCATION: (1)..(676)
<223> OTHER INFORMATION: BPV upstream regulatory region

<400> SEQUENCE: 5

| tttttcacac | atagcgggac | cgaacacgtt | ataagtatcg | attaggtcta | tttttgtctc | 60  |
| tctgtcggaa | ccagaactgg | taaaagtttc | cattgcgtct | gggcttgtct | atcattgcgt | 120 |
| ctctatggtt | tttggaggat | tagacggggc | caccagtaat | ggtgcatagc | ggatgtctgt | 180 |
| accgccatcg | gtgcaccgat | ataggtttgg | ggctccccaa | gggactgctg | ggatgacagc | 240 |
| ttcatattat | attgaatggg | cgcataatca | gcttaattgg | tgaggacaag | ctacaagttg | 300 |
| taacctgatc | tccacaaagt | acgttgccgg | tcgggtcaa  | accgtcttcg | gtgctcgaaa | 360 |
| ccgccttaaa | ctacagacag | gtcccagcca | agtaggcgga | tcaaaacctc | aaaaaggcgg | 420 |
| gagccaatca | aaatgcagca | ttatatttta | agctcaccga | aaccggtaag | taaagactat | 480 |
| gtatttttc  | ccagtgaata | attgttgtta | acaataatca | caccatcacc | gttttttcaa | 540 |
| gcgggaaaaa | atagccagct | aactataaaa | agctgctgac | agaccccggt | tttcacatgg | 600 |
| acctgaaacc | ttttgcaaga | accaatccat | tctcagggtt | ggattgtctg | tggtgcagag | 660 |
| agcctcttac | agaagt     |            |            |            |            | 676 |

<210> SEQ ID NO 6
<211> LENGTH: 12
<212> TYPE: DNA
<213> ORGANISM: Bovine Papillomavirus
<220> FEATURE:
<221> NAME/KEY: protein_bind
<222> LOCATION: (1)..(12)
<223> OTHER INFORMATION: High affinity E2 binding site 9 of the BPV-1
      URR

<400> SEQUENCE: 6

| accgttgccg | gt | 12 |

<210> SEQ ID NO 7
<211> LENGTH: 22
<212> TYPE: DNA
<213> ORGANISM: Bovine Papillomavirus
<220> FEATURE:
<221> NAME/KEY: primer_bind
<222> LOCATION: (1)..(22)
<223> OTHER INFORMATION: BPV-1 nucleotides 6959-6979

<400> SEQUENCE: 7

| aaaagctttc | tttggactta | ga | 22 |

```
<210> SEQ ID NO 8
<211> LENGTH: 22
<212> TYPE: DNA
<213> ORGANISM: Bovine Papillomavirus
<220> FEATURE:
<221> NAME/KEY: primer_bind
<222> LOCATION: (1)..(18)
<223> OTHER INFORMATION: BPV-1 nucleotides 45 to 63 flanked by BglII
      site

<400> SEQUENCE: 8
atagccagct aactatagat ct                                              22

<210> SEQ ID NO 9
<211> LENGTH: 23
<212> TYPE: PRT
<213> ORGANISM: Influenza virus
<220> FEATURE:
<221> NAME/KEY: SITE
<222> LOCATION: (1)..(23)
<223> OTHER INFORMATION: HA amino acid sequence that may be included
      in the fusogenic peptide.

<400> SEQUENCE: 9

Gly Leu Phe Gly Ala Ile Ala Gly Phe Ile Gly Ala Gly Thr Gly Gly
 1               5                  10                  15

Met Ile Ala Gly Gly Gly Cys
                20
```